(12) United States Patent
Choi et al.

(10) Patent No.: US 7,968,557 B2
(45) Date of Patent: Jun. 28, 2011

(54) SUBSTITUTED PYRROLO[2,3-2]PYRIMIDINES AS PROTEIN KINASE INHIBITORS

(75) Inventors: Ha-Soon Choi, San Diego, CA (US); Zhicheng Wang, San Diego, CA (US); Nathanael Schiander Gray, Boston, MA (US); Xiang-ju Gu, San Diego, CA (US); Xiaohui He, San Diego, CA (US); Yun He, San Diego, CA (US); Tao Jiang, San Diego, CA (US); Yi Liu, San Diego, CA (US); Wendy Richmond, San Diego, CA (US); Taebo Sim, Chestnut Hill, MA (US); Kunyong Yang, San Diego, CA (US)

(73) Assignee: Novartis AG, Basel (CH)

( * ) Notice: Subject to any disclaimer, the term of this patent is extended or adjusted under 35 U.S.C. 154(b) by 948 days.

(21) Appl. No.: 10/589,099

(22) PCT Filed: Feb. 14, 2005

(86) PCT No.: PCT/US2005/004630
§ 371 (c)(1),
(2), (4) Date: Jun. 11, 2007

(87) PCT Pub. No.: WO2005/080393
PCT Pub. Date: Sep. 1, 2005

(65) Prior Publication Data
US 2007/0225306 A1  Sep. 27, 2007

Related U.S. Application Data

(60) Provisional application No. 60/544,944, filed on Feb. 14, 2004.

(51) Int. Cl.
C07D 487/04 (2006.01)
A61K 31/519 (2006.01)
A61P 35/00 (2006.01)
A61P 37/06 (2006.01)

(52) U.S. Cl. .................. 514/265.1; 544/280; 544/279; 514/264.1

(58) Field of Classification Search .................. 544/280; 514/265.1
See application file for complete search history.

(56) References Cited

U.S. PATENT DOCUMENTS

2004/0224964 A1  11/2004  O'Yang et al.

FOREIGN PATENT DOCUMENTS

| SU | 194820 | 4/1967 |
| WO | WO03/074530 A1 | 9/2003 |
| WO | WO2005/107760 A1 | 11/2005 |
| WO | WO2006/074985 A1 | 7/2006 |

OTHER PUBLICATIONS

Wolff, Manfred E. "Burger's Medicinal Chemistry, 5ed, Part I", John Wiley & Sons, 1995, pp. 975-977.*
Banker, G.S. et al, "Modern Pharmaceutics, 3ed.", Marcel Dekker, New York, 1996, pp. 451 and 596.*
Vippagunta, S.R., "Advanced Drug Delivery Reviews," 2001, 48, pp. 3-26.*
Ha-Soon Choi et al., Design and Synthesis of 7H-Pyrrolo[2,3-d]pyrimidines as Focal Adhesion Kinase Inhibitors. Part 1, Bioorganic & Medical Chemistry Letters, Feb. 3, 2006, 2173-2176, Elsevier Ltd.
Ha-Soon Choi et al., Design and Synthesis of 7H-Pyrrolo[2,3-d]pyrimidines as Focal Adhesion Kinase Inhibitors. Part 2, Bioorganic & Medical Chemistry Letters, Mar. 9, 2006, 2689-2692, Elsevier Ltd.
Yakhontov et al; "Azaindole Derivatives XXVI. The Formation of 5,7-diazaindoline derivatives by the reaction of 4-chloro-5-(beta-chloroethyl)pyrimidines with secondary amines"; Khimiya Geterotsiklicheskikh Soedinenii 1:145-148 (1969)—English translation of abstract and partial experimentals provided.

* cited by examiner

Primary Examiner — Susanna Moore
(74) Attorney, Agent, or Firm — Scott W. Reid; Novartis AG

(57) ABSTRACT

The invention provides a novel class of compounds, pharmaceutical compositions comprising such compounds and methods of using such compounds to treat or prevent diseases or disorders associated with abnormal or deregulated kinase activity, particularly diseases or disorders that involve abnormal activation of the FAK, Abl, BCR-Abl, PDGF-R, c-Kit, NPM-ALK, Flt-3, JAK2 and c-Met kinases.

8 Claims, No Drawings

SUBSTITUTED PYRROLO[2,3-2]PYRIMIDINES AS PROTEIN KINASE INHIBITORS

CROSS-REFERENCE TO RELATED APPLICATIONS

This application is a 371 U.S. national phase application of international application number PCT/US2005/004630 filed 14 Feb. 2005, which application claims priority to U.S. Provisional patent application number 60/544,944, filed 14 Feb. 2004. The present Application claims priority to and benefit of these applications, the disclosures of which are Incorporated herein by reference for all purposes.

BACKGROUND OF THE INVENTION

1. Field of the Invention

The invention provides a novel class of compounds, pharmaceutical compositions comprising such compounds and methods of using such compounds to treat or prevent diseases or disorders associated with abnormal or deregulated kinase activity, particularly diseases or disorders that involve abnormal activation of the FAK, Abl, BCR-Abl, PDGF-R, c-Kit, NPM-ALK, Flt-3, JAK2 and c-Met kinases.

BACKGROUND

The protein kinases represent a large family of proteins, which play a central role in the regulation of a wide variety of cellular processes and maintaining control over cellular function. A partial, non-limiting, list of these kinases include: receptor tyrosine kinases such as platelet-derived growth factor receptor kinase (PDGF-R), the receptor kinase for stem cell factor, c-kit, the nerve growth factor receptor, trkB, c-Met, and the fibroblast growth factor receptor, FGFR3; non-receptor tyrosine kinases such Abl and the fusion kinase BCR-Abl, focal adhesion kinase (FAM), Fes, Lck and Syk; and serine/threonine kinases such as b-RAF, MAP kinases (e.g., MKK6) and SAPK2β. Aberrant kinase activity has been observed in many disease states including benign and malignant proliferative disorders as well as diseases resulting from inappropriate activation of the immune and nervous systems.

The novel compounds of this invention inhibit the activity of one or more protein kinases and are, therefore, expected to be useful in the treatment of kinase-associated diseases.

SUMMARY OF THE INVENTION

In one aspect, the present invention provides compounds selected from Formulae Ia, Ib, Ic, Id and Ie:

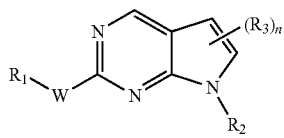

Ia

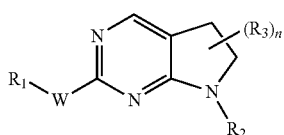

Ib

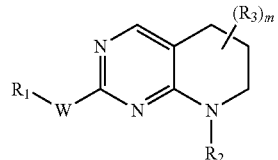

Ic

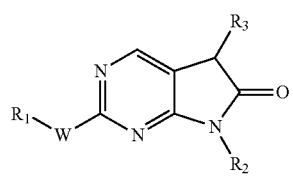

Id

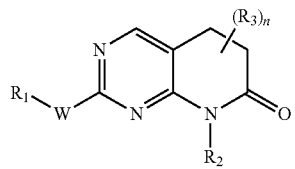

Ie in which:

n is selected from 0, 1 and 2; m is selected from 0, 1, 2 and 3;

w is selected from $-NR_4-$, $-S-$, $-O-$, $-S(O)-$ and $-S(O)_2-$; wherein $R_4$ is selected from hydrogen and $C_{1-6}$alkyl;

$R_1$ is selected from $C_{6-10}$aryl-$C_{0-4}$alkyl, $C_{5-10}$heteroaryl-$C_{0-4}$alkyl, $C_{3-12}$cycloalkyl-$C_{0-4}$alkyl and $C_{3-8}$heterocycloalkyl-$C_{0-4}$alkyl; wherein any arylalkyl, heteroarylalkyl, cycloalkylalkyl or heterocycloalkylalkyl of $R_1$ is optionally substituted by 1 to 3 radicals independently selected from halo, nitro, cyano, $C_{6-10}$aryl, $C_{5-10}$heteroaryl, $C_{3-12}$cycloalkyl, $C_{3-8}$heterocycloalkyl, $C_{1-6}$alkyl, $C_{1-6}$alkoxy, halo-substituted-$C_{1-6}$alkyl, halo-substituted-$C_{1-6}$alkoxy, $-XNR_5R_5$, $-XNR_5XNR_5R_5$, $-XNR_5XOR_5$, $-XOR_5$, $-XSR_5$, $-XS(O)R_5$, $-XS(O)_2R_5$, $-XC(O)NR_5R_5$, $-XOXR_6$ and $-XC(O)R_6$; wherein X is a bond or $C_{1-6}$alkylene; $R_5$ is selected from hydrogen, $C_{1-6}$alkyl and $C_{3-12}$cycloalkyl-$C_{0-4}$alkyl; and $R_6$ is selected from $C_{3-8}$heterocycloalkyl-$C_{0-4}$alkyl and $C_{5-10}$heteroaryl-$C_{0-4}$alkyl optionally substituted by 1 to 3 radicals selected from $C_{1-6}$alkyl and $-C(O)OH$; wherein any aryl, heteroaryl, cycloalkyl or heterocycloalkyl substituent of $R_1$ is further optionally substituted by 1 to 5 radicals independently selected from $C_{1-6}$alkyl and $C_{1-6}$alkoxy;

$R_2$ is selected from $C_{6-10}$aryl-$C_{0-4}$alkyl, $C_{5-10}$heteroaryl-$C_{0-4}$alkyl, $C_{3-12}$cycloalkyl-$C_{0-4}$alkyl and $C_{3-8}$heterocycloalkyl-$C_{0-4}$alkyl; wherein any arylalkyl, heteroarylalkyl, cycloalkylalkyl or heterocycloallkylalkyl of $R_2$ is optionally substituted by 1 to 3 radicals independently selected from halo, nitro, cyano, $C_{1-6}$alkyl, $C_{1-6}$alkenyl, $C_{1-6}$alkynyl, $C_{1-6}$alkoxy, halo-substituted-$C_{1-6}$alkyl, halo-substituted-$C_{1-6}$alkoxy, $C_{3-8}$heteroaryl$C_{0-4}$alkyl, $-XNR_5R_5$, $-XOR_5$, $-XSR_5$, $-XS(O)R_5$, $-XS(O)_2R_5$, $-XSNR_5R_5$, $-XS(O)NR_5R_5$, $-XS(O)_2NR_5R_5$, $-XC(O)OR_5$, $-XOC(O)R_5$, $-XC(O)R_5$, $-XC(O)NR_5XNR_5R_5$, $-XC(O)NR_5R_5$, $-XC(O)NR_5XC(O)OR_5$, $-XC(O)NR_5XNR_5C(O)R_5$, $-XC(O)NR_5XNR_5C(O)OR_5$, $-XC(O)NR_5XOR_5$, $-XC(O)N(XOR_5)_2$, $-XNR_5C(O)R_5$, $-XC(O)NR_5R_6$, $-XC(O)R_6$, $-XR_7$, $-XR_6$ and $-XC(O)NR_5XR_7$; wherein X is a bond or $C_{1-6}$alkylene; and $R_5$ is selected from hydrogen, $C_{1-6}$alkyl and $C_{3-12}$cycloalkyl-$C_{0-4}$alkyl; $R_6$ is selected from $C_{3-8}$heterocycloalkyl-$C_{0-4}$alkyl and $C_{5-10}$heteroaryl-$C_{0-}$ $_4$alkyl optionally substituted by 1 to 3 radicals selected from $C_{1-6}$alkyl and —C(O)OH; and $R_7$ is cyano;

$R_3$ is selected from halo, hydroxy, —XSR$_5$, —XS(O)R$_5$, —XS(O)$_2$R$_5$, —XC(O)R$_5$ and —XC(O)OR$_5$; wherein X is a bond or $C_{1-6}$alkylene; and $R_5$ is selected from hydrogen, $C_{1-6}$alkyl and $C_{3-12}$cycloalkyl-$C_{0-4}$alkyl; and the N-oxide derivatives, prodrug derivatives, protected derivatives, individual isomers and mixture of isomers thereof; and the pharmaceutically acceptable salts and solvates (e.g. hydrates) of such compounds.

In a second aspect, the present invention provides a pharmaceutical composition which contains a compound of Formula I or a N-oxide derivative, individual isomers and mixture of isomers thereof; or a pharmaceutically acceptable salt thereof, in admixture with one or more suitable excipients.

In a third aspect, the present invention provides a method of treating a disease in an animal in which inhibition of kinase activity, particularly FAK, Abl, BCR-Abl, PDGF-R, c-Kit, NPM-ALK, Flt-3, JAK2 and/or c-Met activity, can prevent, inhibit or ameliorate the pathology and/or symptomology of the diseases, which method comprises administering to the animal a therapeutically effective amount of a compound of Formula I or a N-oxide derivative, individual isomers and mixture of isomers thereof, or a pharmaceutically acceptable salt thereof.

In a fourth aspect, the present invention provides the use of a compound of Formula I in the manufacture of a medicament for treating a disease in an animal in which kinase activity, particularly FAK, Abl, BCR-Abl, PDGF-R, c-Kit, NPM-ALK, Flt-3, JAK2 and/or c-Met activity, contributes to the pathology and/or symptomology of the disease.

In a fifth aspect, the present invention provides a process for preparing compounds of Formula I and the N-oxide derivatives, prodrug derivatives, protected derivatives, individual isomers and mixture of isomers thereof, and the pharmaceutically acceptable salts thereof.

DETAILED DESCRIPTION OF THE INVENTION

Definitions

"Alkyl" as a group and as a structural element of other groups, for example halo-substituted-alkyl and alkoxy, can be either straight-chained or branched. $C_{1-4}$-alkoxy includes, methoxy, ethoxy, and the like. Halo-substituted alkyl includes trifluoromethyl, pentafluoroethyl, and the like.

"Aryl" means a monocyclic or fused bicyclic aromatic ring assembly containing six to ten ring carbon atoms. For example, aryl may be phenyl or naphthyl, preferably phenyl. "Arylene" means a divalent radical derived from an aryl group. "Heteroaryl" is as defined for aryl where one or more of the ring members are a heteroatom. For example heteroaryl includes pyridyl, indolyl, indazolyl, quinoxalinyl, quinolinyl, benzofuranyl, benzopyranyl, benzothiopyranyl, benzo[1,3]dioxole, imidazolyl, benzo-imidazolyl, pyrimidinyl, furanyl, oxazolyl, isoxazolyl, triazolyl, tetrazolyl, pyrazolyl, thienyl, etc.

"Cycloalkyl" means a saturated or partially unsaturated, monocyclic, fused bicyclic or bridged polycyclic ring assembly containing the number of ring atoms indicated. For example, $C_{3-10}$ycloalkyl includes cyclopropyl, cyclobutyl, cyclopentyl, cyclohexyl, etc. "Heterocycloalkyl" means cycloalkyl, as defined in this application, provided that one or more of the ring carbons indicated, are replaced by a moiety selected from —O—, —N═, —NR—, —C(O)—, —S—, —S(O)— or —S(O)$_2$—, wherein R is hydrogen, $C_{1-4}$alkyl or a nitrogen protecting group. For example, $C_{3-8}$heterocycloalkyl as used in this application to describe compounds of the invention includes morpholino, pyrrolidinyl, piperazinyl, piperidinyl, piperidinylone, 1,4-dioxa-8-aza-spiro[4.5]dec-8-yl, 1,1-dioxo-116-thiomorpholin-4-yl, etc.

"Halogen" (or halo) preferably represents chloro or fluoro, but may also be bromo or iodo.

"Treat", "treating" and "treatment" refer to a method of alleviating or abating a disease and/or its attendant symptoms.

Description of the Preferred Embodiments

The compounds of this invention are useful in the inhibition of kinases and are illustrated by a compound of Formula I as detailed in the Summary of the Invention. In one embodiment, with reference to compounds of Formula Ia, Ib, Ic, Id and Ie, W is selected from —NR$_4$— and —O—; wherein R$_4$ is selected from hydrogen and $C_{1-6}$alkyl.

In a further embodiment, R$_1$ is selected from $C_{6-10}$aryl-$C_{0-4}$alkyl and $C_{5-10}$heteroaryl-$C_{0-4}$alkyl; wherein any arylalkyl and heteroarylalkyl of R$_1$ is optionally substituted by 1 to 3 radicals independently selected from halo, nitro, $C_{5-10}$heteroaryl, $C_{1-6}$alkyl, $C_{1-6}$alkoxy, halo-substituted-$C_{1-6}$alkyl, —XNR$_5$R$_5$, —XOR$_5$, —XSR$_5$, —XNR$_5$XNR$_5$R$_5$, —XNR$_5$XOR$_5$, —XC(O)NR$_5$R$_5$, —XOXR$_6$ and —XC(O)R$_6$; wherein X is a bond or $C_{1-6}$alkylene; R$_5$ is selected from hydrogen, $C_{1-6}$alkyl and $C_{3-12}$cycloalkyl-$C_{0-4}$alkyl; and R$_6$ is selected from $C_{3-8}$heterocycloalkyl-$C_{0-4}$alkyl and $C_{5-10}$heteroaryl-$C_{0-4}$alkyl optionally substituted by 1 to 3 radicals selected from $C_{1-6}$alkyl and —C(O)OH; wherein any heteroaryl substituent of R$_1$ is further optionally substituted by 1 to 5 $C_{1-6}$alkyl radicals.

In a further embodiment, R$_2$ is selected from $C_{6-10}$aryl-$C_{0-4}$alkyl and $C_{5-10}$heteroaryl-$C_{0-4}$alkyl; wherein any arylalkyl or heteroarylalkyl of R$_2$ is optionally substituted by 1 to 3 radicals independently selected from halo, nitro, cyano, $C_{1-6}$alkyl, $C_{1-6}$alkenyl, $C_{1-6}$alkoxy, halo-substituted-$C_{1-6}$alkyl, $C_{3-8}$heteroaryl$C_{0-4}$alkyl, —XNR$_5$R$_5$, —XOR$_5$, —XSR$_5$, —XS(O)$_2$NR$_5$R$_5$, —XC(O)OR$_5$, —XOC(O)R$_5$, —XC(O)NR$_5$XNR$_5$R$_5$, —XC(O)NR$_5$XC(O)OR$_5$, —XC(O)NR$_5$XNR$_5$C(O)R$_5$, —XC(O)NR$_5$XNR$_5$C(O)OR$_5$, —XC(O)NR$_5$XOR$_5$, —XC(O)N(XOR$_5$)$_2$, —XNR$_5$C(O)R$_5$, —XC(O)NR$_5$R$_6$, —XC(O)R$_6$, —XR$_7$, —XR$_6$ and —XC(O)NR$_5$XR$_7$; wherein X is a bond or $C_{1-6}$alkylene; and R$_5$ is selected from hydrogen, $C_{1-6}$alkyl and $C_{3-12}$cycloalkyl-$C_{0-4}$alkyl; R$_6$ is selected from $C_{3-8}$heterocycloalkyl-$C_{0-4}$alkyl and $C_{5-10}$heteroaryl-$C_{0-4}$alkyl optionally substituted by 1 to 3 radicals selected from $C_{1-6}$alkyl and —C(O)OH; and R$_7$ is cyano.

In a further embodiment, R$_3$ is selected from halo, hydroxy, —XC(O)R$_5$ and —XC(O)OR5; wherein X is a bond or $C_{1-6}$alkylene; and R$_5$ is selected from hydrogen, $C_{1-6}$alkyl and $C_{3-12}$cycloalkyl-$C_{0-4}$alkyl.

In a further embodiment, W is selected from —NH— and —O—; and R$_1$ is selected from phenyl, benzyl, 5,6,7,8-tetrahydro-naphthalenyl, benzo[1,3]dioxolyl, 1H-indazol-7-yl, indan-4-yl and 1H-indolyl; wherein any arylalkyl and heteroarylalkyl of R$_1$ is optionally substituted by 1 to 3 radicals independently selected from methoxy, methyl, amino, halo, hydroxymethyl, hydroxy, quinoxalinyl, ethyl, pyridinyl, methoxy-phenyl, piperazinyl-carbonyl, ethyl-(2-hydroxy-ethyl)-amino 2-(4-methyl-piperazin-1-yl)-ethoxy, formamyl, isopropyl, methyl-sulfanyl, tri-fluoro-methyl, ethoxy, 3-isopropylamino-propylamino, dimethyl-amino, morpholino, cyclopropyl-methoxy, butoxy, cycloheptyl-oxy and 1,4,5,7-tetramethyl-pyrrolo[3,4-d]pyridazinyl.

In a further embodiment, R$_2$ is selected from pyridinyl, phenyl, thiazolyl, pyridinyl-methyl, pyridinyl-ethyl, thiophenyl, benzyl, quinolinyl, 7-oxo-5,6,7,8-tetrahydro-naphthalenyl, naphthyl and pyrimidinyl; wherein any arylalkyl or heteroarylalkyl of R₂ is optionally substituted by 1 to 3 radicals independently selected from halo, nitro, cyano, methyl, propyl-sulfamoyl, methyl-sulfamoyl, methoxy, methyl-carboxy, 2-dimethylamino-ethyl-formamyl, carboxy, amino, cyano-ethyl, cyano-methyl, ethenyl, tri-fluoro-methyl, hydroxy-methyl, ethyl, methyl-sulfanyl, butyl, isobutyl, carboxy-methyl-formamidyl, 1-carboxy-ethyl-formamidyl, carboxy-ethyl, amino-ethyl-formamidyl, amino-propyl-formamidyl, dimethyl-amino-ethyl-formamidyl, dimethyl-amino-propyl-formamidyl, dimethyl-amino-butyl-formamidyl-methyl-formamidyl, ethyl-formamidyl, ethyl-formamidyl-methyl, 2-(2-dimethylamino-ethylcarbamoyl)-ethyl, 2-(2-dimethylamino-formamidyl)-ethyl, 2-(amino-ethyl-formamidyl)-ethyl, 2-(amino-propyl-formamidyl)-ethyl, 2-(propyl-formamidyl)-ethyl, amino-propyl-formamidyl-methyl, 2-(methyl-amino-carbamoyl)-ethyl, 2-(ethyl-amino-carbamoyl)-ethyl, morpholino-ethyl-formamidyl, morpholino-carbonyl-methyl, ammino-ethyl-formamidyl-methyl, cyclobutyl-formamidyl, methyl-formamidyl-methyl, dimethyl-formamidyl-methyl, hydroxy-ethyl-formamidyl-methyl, hydroxy-propyl-formamidyl-methyl, N,N-bis-(3-hydroxy-propyl)-formamidyl, cyclopentyl-formamidyl, isobutyl-formamidyl, isobutyl-formamidyl-methyl, cyclopentyl-formamidyl-methyl, cyano-ethyl-formamidyl, cyano-methyl-formamidyl, pyrrolidinyl-ethyl-formamidyl, 2-(isobutyl-formamidyl)-ethyl, 1H-tetrazolyl, 2-(1H-tetrazol-5-yl)-ethyl, 2-(1H-tetrazol-5-yl)-methyl, 2-(1-methyl-1H-tetrazol-5-yl)-methyl, acetyl-amino, cyclopropyl-formamidyl-methyl, hydroxy-ethyl-formamidyl, hydroxy-propyl-formamidyl, propyl-formamidyl-methyl, ethoxy-propyl-formamidyl, acetyl-amino-ethyl-formamidyl, 1-methyl-piperidin-4-yl-formamidyl, morpholino-carbonyl-ethyl, methoxy-carbonyl-methyl, methoxy-carbonyl-ethyl-formamidyl, methoxy-carbonyl-ethyl-formamidyl-methyl, methoxy-carbonyl-methyl-formamidyl-methyl, methoxy-carbonyl-methyl-formamidyl, 4-amino-cyclohexyl-formamidyl, 4-amino-cyclohexyl-formamidyl-methyl, acetyl-amino-ethyl-formamidyl-methyl, ethoxy-propyl-formamidyl-methyl, methoxy-carbonyl-ethyl, 1-formyl-pyrrolidin-2-yl-carboxylic acid, (1-carboxy-3-methyl-butyl)-formamidyl, 2-(methoxy-carbonyl-methyl-formamidyl)-ethyl, 1-carboxy-(2,2-dimethyl-propyl)-formamidyl, 3-tert-butoxycarbonyl-amino-propyl-formamidyl, acetoxy-methyl and 1-carboxy-ethyl-formamidyl.

Preferred compounds of Formula I are detailed in the Examples and Table I, infra.

Pharmacology and Utility

Compounds of the invention modulate the activity of protein tyrosine kinases and, as such, are useful for treating diseases or disorders in which protein tyrosine kinases, particularly FAK, Abl, BCR-Abl, PDGF-R, c-Kit, NPM-ALK, Flt-3, JAK2 and c-Met kinases, contribute to the pathology and/or symptomology of the disease.

Focal adhesion kinase (FAK), a non-receptor protein-tyrosine kinase, is localized to cell substratum-extracellular matrix (ECM) contact sites that function as part of a cytoskeletal-associated network of signaling proteins (Schlaepfer, et al., Prog. Diophys., Mol., 1999, 71, 435-478. In adherent cells, FAK is often associated with integrins at focal adhesions (Schlaepfer, et al., Proc. Natl. Acad. Sci. USA, 1992, 89, 5192-5196). Phosphorylation of FAK results in activation of the mitogen-activated protein kinase pathway. Overexpression of FAK is involved in cancer progression. High levels of FAK correlate with invasiveness and metastatic potential in colon tumors (Weiner, T. M., et al., Lancet, 1993, 342, 1024-1025), breast tumors (Owens, L. V., et al., Cancer Res., 1995, 55, 2752-2755) and oral cancers (Kornberg, L. J., Head Neck, 1998, 20, 634-639). The role of FAK in cell migration has led to the speculation that it may be relevant in other diseases such as embryonic development dysfunctions and angiogenic disorders (Kornberg, L. J., Head Neck, 1998, 20, 634-639).

In a further embodiment, n is 0 or 1; m is 0 or 1; and R₃ is selected from halo, hydroxy, —C(O)OH and —C(O)OCH₃.

In another embodiment are compounds of Formula Ig:

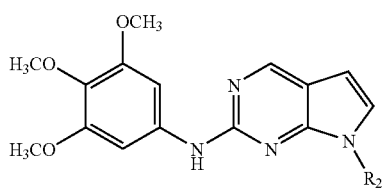

Ig in which R₂ is selected from pyridinyl, phenyl, thiazolyl, pyridinyl-methyl, pyridinyl-ethyl, thiophenyl, benzyl, quinolinyl, 7-oxo-5,6,7,8-tetrahydro-naphthalenyl, naphthyl and pyrimidinyl; wherein any arylalkyl or heteroarylalkyl of R₂ is optionally substituted by 1 to 3 radicals independently selected from halo, nitro, cyano, methyl, propyl-sulfamoyl, methyl-sulfamoyl, methoxy, methyl-carboxy, 2-dimethylamino-ethyl-formamyl, carboxy, amino, cyano-ethyl, Abelson tyrosine kinase (i.e. Abl, c-Abl) is involved in the regulation of the cell cycle, in the cellular response to genotoxic stress, and in the transmission of information about the cellular environment through integrin signaling. Overall, it appears that the Abl protein serves a complex role as a cellular module that integrates signals from various extracellular and intracellular sources and that influences decisions in regard to cell cycle and apoptosis. Abelson tyrosine kinase includes sub-types derivatives such as the chimeric fusion (oncoprotein) BCR-Abl with deregulated tyrosine kinase activity or the v-Abl. BCR-Abl is critical in the pathogenesis of 95% of chronic myelogenous leukemia (CML) and 10% of acute lymphocytic leukemia. STI-571 (Gleevec) is an inhibitor of the oncogenic BCR-Abl tyrosine kinase and is used for the treatment of chronic myeloid leukemia (CML). However, some patients in the blast crisis stage of CML are resistant to STI-571 due to mutations in the BCR-Abl kinase. Over 22 mutations have been reported to date with the most common being G250E, E255V, T315I, F317L and M351 T.

Compounds of the present invention inhibit abl kinase, especially v-abl kinase. The compounds of the present invention also inhibit wild-type BCR-Abl kinase and mutations of BCR-Abl kinase and are thus suitable for the treatment of Bcr-abl-positive cancer and tumor diseases, such as leukemias (especially chronic myeloid leukemia and acute lymphoblastic leukemia, where especially apoptotic mechanisms of action are found), and also shows effects on the subgroup of leukemic stem cells as well as potential for the purification of these cells in vitro after removal of said cells (for example, bone marrow removal) and reimplantation of the cells once they have been cleared of cancer cells (for example, reimplantation of purified bone marrow cells).

PDGF (Platelet-derived Growth Factor) is a very commonly occurring growth factor, which plays an important role both in normal growth and also in pathological cell proliferation, such as is seen in carcinogenesis and in diseases of the smooth-muscle cells of blood vessels, for example in atherosclerosis and thrombosis. Compounds of the invention can inhibit PDGF receptor (PDGFR) activity and are, therefore, suitable for the treatment of tumor diseases, such as gliomas, sarcomas, prostate tumors, and tumors of the colon, breast, and ovary.

Compounds of the present invention, can be used not only as a tumor-inhibiting substance, for example in small cell lung cancer, but also as an agent to treat non-malignant proliferative disorders, such as atherosclerosis, thrombosis, psoriasis, scleroderma and fibrosis, as well as for the protection of stem cells, for example to combat the hemotoxic effect of chemotherapeutic agents, such as 5-fluoruracil, and in asthma. Compounds of the invention can especially be used for the treatment of diseases, which respond to an inhibition of the PDGF receptor kinase.

Compounds of the present invention show useful effects in the treatment of disorders arising as a result of transplantation, for example, allogenic transplantation, especially tissue rejection, such as especially obliterative bronchiolitis (OB), i.e. a chronic rejection of allogenic lung transplants. In contrast to patients without OB, those with OB often show an elevated PDGF concentration in bronchoalveolar lavage fluids.

Compounds of the present invention are also effective in diseases associated with vascular smooth-muscle cell migration and proliferation (where PDGF and PDGF-R often also play a role), such as restenosis and atherosclerosis. These effects and the consequences thereof for the proliferation or migration of vascular smooth-muscle cells in vitro and in vivo can be demonstrated by administration of the compounds of the present invention, and also by investigating its effect on the thickening of the vascular intima following mechanical injury in vivo.

The compounds of the present invention also inhibit cellular processes involving stem-cell factor (SCF, also known as the c-kit ligand or steel factor), such as inhibiting SCF receptor (kit) autophosphorylation and SCF-stimulated activation of MAPK kinase (mitogen-activated protein kinase). MO7e cells are a human promegakaryocytic leukemia cell line, which depends on SCF for proliferation. Compounds of the invention can inhibit the autophosphorylation of SCF receptors.

The Ras-Raf-MEK-ERK signaling pathway mediates cellular response to growth signals. Ras is mutated to an oncogenic form in ~15% of human cancer. The Raf family belongs to the serine/threonine protein kinase and it includes three members, A-Raf, B-Raf and c-Raf (or Raf-1). The focus on Raf being a drug target has centered on the relationship of Raf as a downstream effector of Ras. However, recent data suggests that B-Raf may have a prominent role in the formation of certain tumors with no requirement for an activated Ras allele (Nature 417, 949-954 (01 Jul. 2002). In particular, B-Raf mutations have been detected in a large percentage of malignant melanomas.

Existing medical treatments for melanoma are limited in their effectiveness, especially for late stage melanomas. The compounds of the present invention also inhibit cellular processes involving b-Raf kinase, providing a new therapeutic opportunity for treatment of human cancers, especially for melanoma.

The compounds of the present invention also exhibit powerful inhibition of the tyrosine kinase activity of anaplastic lymphoma kinase (ALK) and the fusion protein of NPM-ALK. This protein tyrosine kinase results from a gene fusion of nucleophosmin (NPM) and the anaplastic lymphoma kinase (ALK), rendering the protein tyrosine kinase activity of ALK ligand-independent. NPM-ALK plays a key role in signal transmission in a number of hematopoietic and other human cells leading to hematological and neoplastic diseases, for example in anaplastic large-cell lymphoma (ALCL) and non-Hodgkin's lymphomas (NHL), specifically in ALK+NHL or Alkomas, in inflammatory myofibroblastic tumors (IMT) and neuroblastomas (Duyster, J. et al., 2001, Oncogene 20, 5623-5637). In addition to NPM-ALK, other gene fusions have been identified in human hematological and neoplastic diseases; mainly TPM3-ALK (a fusion of nonmuscle tropomyosin with ALK). The inhibition of ALK tyrosine kinase activity can be demonstrated using known methods, for example using the recombinant kinase domain of the ALK in analogy to the VEGF-R kinase assay described in J. Wood et al. Cancer Res. 60 2178-2189 (2000).

Flt3 is a member of the type III receptor tyrosine kinase (RTK) family. Flt3 (fms-like tyrosine kinase) is also known as FLk-2 (fetal liver kinase 2). Aberrant expression of the Flt3 gene has been documented in both adult and childhood leukemias including acute myeloid leukemia (AML), AML with trilineage myelodysplasia (AML/TMDS), acute lymphoblastic leukemia (ALL), and myelodysplastic syndrome (MDS). Activating mutations of the Flt3 receptor have been found in about 35% of patients with acute myeloblastic leukemia (AML), and are associated with a poor prognosis. The most common mutation involves in-frame duplication within the juxtamembrane domain, with an additional 5-10% of patients having a point mutation at asparagine 835. Both of these mutations are associated with constitutive activation of the tyrosine kinase activity of Flt3, and result in proliferation and viability signals in the absence of ligand. Patients expressing the mutant form of the receptor have been shown to have a decreased chance for cure. Thus, there is accumulating evidence for a role for hyper-activated (mutated) Flt3 kinase activity in human leukemias and myelodysplastic syndrome. This has prompted the applicant to search for new inhibitors of the Flt3 receptor as a possible therapeutic approach in these patients, for whom current drug therapies offer little utility, and for such patients who have previously failed current available drug therapies and/or stem cell transplantation therapies.

Leukemias generally result from an acquired (not inherited) genetic injury to the DNA of immature hematopoietic cells in the bone marrow, lymph nodes, spleen, or other organs of the blood and immune system. The effects are: the accelerated growth and blockage in the maturation of cells, resulting in the accumulation of cells called "leukemic blasts", which do not function as normal blood cells; and a failure to produce normal marrow cells, leading to a deficiency of red cells (anemia), platelets and normal white cells. Blast cells are normally produced by bone marrow and usually develop into mature blood cells, comprising about 1 percent of all marrow cells. In leukemia, the blasts do not mature properly and accumulate in the bone marrow. In acute myeloid leukemia (AML), these are called myeloblasts while in acute lymphoblastic leukemia (ALL) they are known as lymphoblasts. Another leukemia is mixed-lineage leukemia (MLL).

The term "AML with trilineage myelodysplasia (AML/TMDS)" relates to an uncommon form of leukemia characterized by a dyshematopoietic picture accompanying the acute leukemia, a poor response to induction chemotherapy, and a tendency to relapse with pure myelodysplastic syndrome.

The term "Myelodysplastic Syndrome (MDS)" relates to a group of blood disorders in which the bone marrow stops functioning normally, resulting in a deficiency in the number of healthy blood cells. Compared with leukemia, in which one type of blood cell is produced in large numbers, any and sometimes all types of blood cells are affected in MDS. At least 10,000 new cases occur annually in the United States. Up to one third of patients diagnosed with MDS go on to develop acute myeloid leukemia. For this reason the disease is sometimes referred to as preleukemia. Myelodysplastic syndrome is sometimes also called myelodysplasia dysmyelopoiesis or oligoblastic leukemia. MDS is also referred to as smoldering leukemia when high numbers of blast cells remain in the marrow.

Myelodysplastic syndrome, like leukemia, results from a genetic injury to the DNA of a single cell in the bone marrow. Certain abnormalities in chromosomes are present in MDS patients. These abnormalities are called translocations, which occur when a part of one chromosome breaks off and becomes attached to a broken part of a different chromosome. The same defects are frequently found in acute myeloid leukemia. However, MDS differs from leukemia because all of the patient's blood cells are abnormal and all are derived from the same damaged stem cell. In leukemia patients, the bone marrow contains a mixture of diseased and healthy blood cells.

AML and advanced myelodysplastic syndromes are currently treated with high doses of cytotoxic chemotherapy drugs such cytosine arabinoside and daunorubicin. This type of treatment induces about 70% of patients to enter a hematological remission. However, more than half of the patients that enter remission will later relapse despite administration of chemotherapy over long periods of time. Almost all of the patients who either fail to enter remission initially, or relapse later after obtaining remission, will ultimately die because of leukemia. Bone marrow transplantation can cure up to 50-60% of patients who undergo the procedure, but only about one third of all patients with AML or MDS are eligible to receive a transplant. New and effective drugs are urgently needed to treat the patients who fail to enter remission with standard therapies, patients who later relapse, and patients that are not eligible for stem cell transplantation. Further, an effective new drug could be added to standard therapy with the reasonable expectation that it will result in improved induction chemotherapy for all patients.

In accordance with the foregoing, the present invention further provides a method for preventing or treating any of the diseases or disorders described above in a subject in need of such treatment, which method comprises administering to said subject a therapeutically effective amount (See, "*Administration and Pharmaceutical Compositions*", infra) of a compound of Formula I or a pharmaceutically acceptable salt thereof. For any of the above uses, the required dosage will vary depending on the mode of administration, the particular condition to be treated and the effect desired.

Administration and Pharmaceutical Compositions

In general, compounds of the invention will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. In general, satisfactory results are indicated to be obtained systemically at daily dosages of from about 0.03 to 2.5 mg/kg per body weight. An indicated daily dosage in the larger mammal, e.g. humans, is in the range from about 0.5 mg to about 100 mg, conveniently administered, e.g. in divided doses up to four times a day or in retard form. Suitable unit dosage forms for oral administration comprise from ca. 1 to 50 mg active ingredient.

Compounds of the invention can be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal or suppository form. Pharmaceutical compositions comprising a compound of the present invention in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a compound of the present invention with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

Compounds of the invention can be administered in therapeutically effective amounts in combination with one or more therapeutic agents (pharmaceutical combinations). For example, synergistic effects can occur with other immunomodulatory, anti-inflammatory or any substances used in the treatment of the diseases mentioned above, for example when used in combination with cyclosporin, rapamycin, or ascomycin, or immunosuppressant analogues thereof, for example cyclosporin A (CsA), cyclosporin G, FK-506, rapamycin, or comparable compounds, corticosteroids, cyclophosphamide, azathioprine, methotrexate, brequinar, leflunomide, mizoribine, mycophenolic acid, mycophenolate mofetil, 15-deoxyspergualin, immunosuppressant antibodies, especially monoclonal antibodies for leukocyte receptors, for example MHC, CD2, CD3, CD4, CD7, CD25, CD28, B7, CD45, CD58 or their ligands, or other immunomodulatory compounds, such as CTLA4Ig. Where the compounds of the invention are administered in conjunction with other therapies, dosages of the co-administered compounds will of course vary depending on the type of co-drug employed, on the specific drug employed, on the condition being treated and so forth.

The invention also provides for a pharmaceutical combinations, e.g. a kit, comprising a) a first agent which is a compound of the invention as disclosed herein, in free form or in pharmaceutically acceptable salt form, and b) at least one co-agent. The kit can comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of Formula I and a co-agent, are both administered to a patient simultaneously in the form of a single entity or dosage. The term "non-fixed combination" means that the active ingredients, e.g. a compound of Formula I and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

Processes for Making Compounds of the Invention

The present invention also includes processes for the preparation of compounds of the invention. In the reactions described, it can be necessary to protect reactive functional groups, for example hydroxy, amino, imino, thio or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1991.

Compounds of Formula I, in which W is —$NR_4$—, can be prepared by proceeding as in the following Reaction Scheme I:

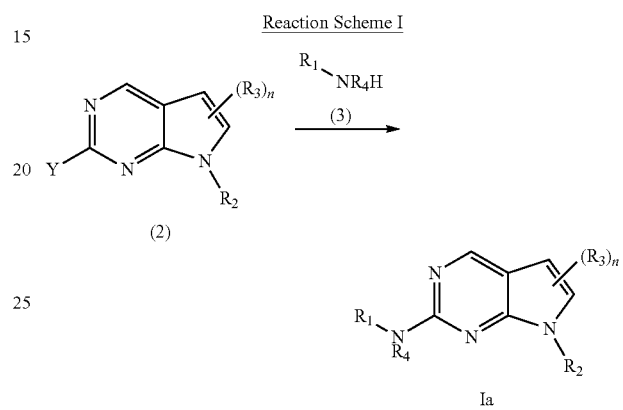

in which $R_1$, $R_2$, $R_3$, $R_4$ and n are as defined for Formula I in the Summary of the Invention and Y is a leaving group such as halogen (e.g. chloro, and the like). A compound of Formula Ia can be prepared by reacting a compound of formula 2 with a compound of formula 3 in the presence of a suitable base (e.g., potassium tertiary butoxide and diisopropylethyl amine, and the like), a suitable solvent (e.g., 1,4-dioxane and butanol, and the like). The reaction is carried out at 50 to 130° C. and can take up to 4 hours to complete. Similarly, using appropriate starting materials, reaction with a compound of formula 3 results in compounds of Formula Ib, Ic, Id and Ie.

Compounds of Formula I, in which W is —O—, can be prepared by proceeding as in the following Reaction Scheme II:

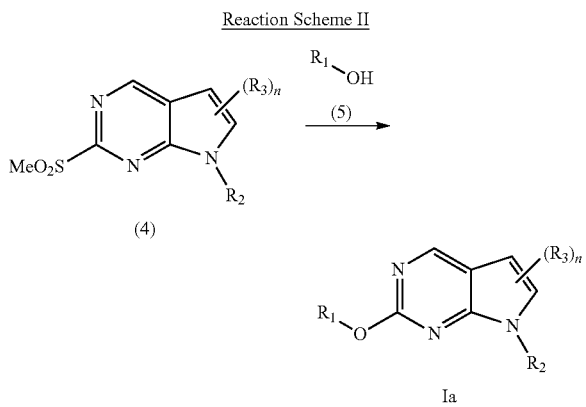

in which $R_1$, $R_2$, $R_3$, $R_4$ and n are as defined for Formula I in the Summary of the Invention. A compound of Formula Ia can be prepared by reacting a compound of formula 4 with a compound of formula 5 in the presence of a suitable solvent (e.g., DMSO, and the like) and a suitable base (e.g., potassium tertiary butoxide, and the like). The reaction is carried out at 50 to 130° C. and can take up to 4 hours to complete.

Detailed descriptions of the synthesis of a compound of Formula I can be found in the Examples, infra.

Additional Processes for Making Compounds of the Invention

A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base. Alternatively, the salt forms of the compounds of the invention can be prepared using salts of the starting materials or intermediates.

The free acid or free base forms of the compounds of the invention can be prepared from the corresponding base addition salt or acid addition salt from, respectively. For example a compound of the invention in an acid addition salt form can be converted to the corresponding free base by treating with a suitable base (e.g., ammonium hydroxide solution, sodium hydroxide, and the like). A compound of the invention in a base addition salt form can be converted to the corresponding free acid by treating with a suitable acid (e.g., hydrochloric acid, etc.)

Compounds of the invention in unoxidized form can be prepared from N-oxides of compounds of the invention by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. acetonitrile, ethanol, aqueous dioxane, or the like) at 0 to 80° C.

Prodrug derivatives of the compounds of the invention can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention can be made by means known to those of ordinary skill in the art. A detailed description of techniques applicable to the creation of protecting groups and their removal can be found in T. W. Greene, "Protecting Groups in Organic Chemistry", $3^{rd}$ edition, John Wiley and Sons, Inc., 1999.

Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxin, tetrahydrofuran or methanol.

Compounds of the invention can be prepared as their individual stereoisomers by reacting a racemic mixture of the compound with an optically active resolving agent to form a pair of diastereoisomeric compounds, separating the diastereomers and recovering the optically pure enantiomers. While resolution of enantiomers can be carried out using covalent diastereomeric derivatives of the compounds of the invention, dissociable complexes are preferred (e.g., crystalline diastereomeric salts). Diastereomers have distinct physical properties (e.g., melting points, boiling points, solubilities, reactivity, etc.) and can be readily separated by taking advantage of these dissimilarities. The diastereomers can be separated by chromatography, or preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions", John Wiley And Sons, Inc., 1981.

In summary, the compounds of Formula I can be made by a process, which involves:

(a) that of reaction schemes I or II; and (b) optionally converting a compound of the invention into a pharmaceutically acceptable salt;

(c) optionally converting a salt form of a compound of the invention to a non-salt form;

(d) optionally converting an unoxidized form of a compound of the invention into a pharmaceutically acceptable N-oxide;

(e) optionally converting an N-oxide form of a compound of the invention to its unoxidized form;

(f) optionally resolving an individual isomer of a compound of the invention from a mixture of isomers;

(g) optionally converting a non-derivatized compound of the invention into a pharmaceutically acceptable prodrug derivative; and (h) optionally converting a prodrug derivative of a compound of the invention to its non-derivatized form.

Insofar as the production of the starting materials is not particularly described, the compounds are known or can be prepared analogously to methods known in the art or as disclosed in the Examples hereinafter.

One of skill in the art will appreciate that the above transformations are only representative of methods for preparation of the compounds of the present invention, and that other well known methods can similarly be used.

EXAMPLES

The present invention is further exemplified, but not limited, by the following examples that illustrate the preparation of compounds of Formula I (Examples) and intermediates (References) according to the invention.

Example 1

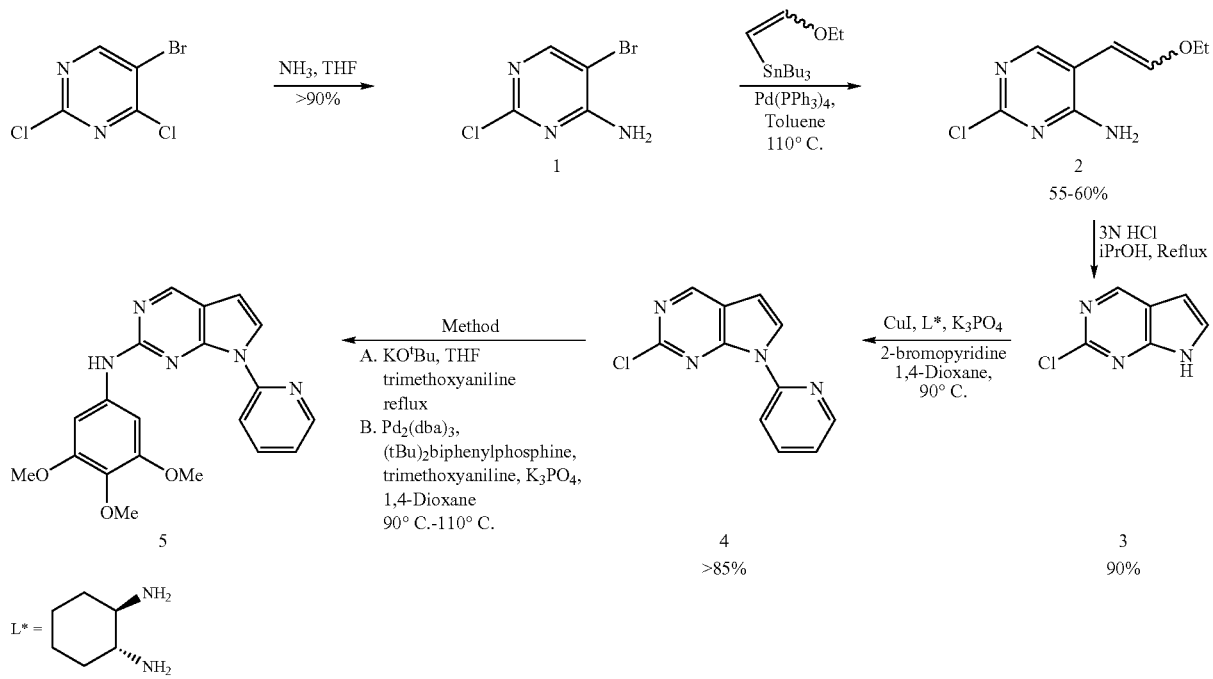

Synthesis of 5-Bromo-2-chloropyrimidin-4-ylamine (1): A solution of 5-bromo-2,4-dichloropyrimidine (25g, 110 mmol) in 200 mL THF is treated with 47 mL of ammonia (330 mmol, 7.0M solution in methanol). After stirring for 15 hours the solution is concentrated under reduced pressure and purified by short-filtration ($SiO_2$, Hexanes: Ethyl acetate/1:1) to yield 21g (92%) of 1 as a white solid.

Synthesis of 2-Chloro-5-(2-ethoxyvinyl)-pyrimidin-4-ylamine (2): A 500 mL round bottomed flask is charged with 5-bromo-2-chloropyrimidin-4-ylamine (1) (10 g, 48 mmol), tetrakis(triphenylphosphine)palladium(0) (2.8g, 2.5 mmol), and toluene (200 mL). Tributyl-(2-ethoxyvinyl)-stannane (22 g, 60 mmol) is added and the reaction heated to 110° C. with stirring for approximately 15 hours. After cooling to room temperature, the solution is diluted with 100 mL ethyl acetate and washed with water and brine. The organic extract is dried over $Na_2SO_4$, filtered, and concentrated under reduced pressure. Purification by column chromatography ($SiO_2$, Hexane: Ethyl acetate/5:1) provides 2 (4.4 g, 46%) as a yellow solid.

Synthesis of 2-Chloro-7H-pyrrolo-[2,3-d]pyrimidine 3: A 500 mL round bottomed flask was charged with 2-Chloro-5-(2-ethoxyvinyl)-pyrimidin-4-ylamine 2 (4.4 g, 20 mmol). Isopropanol (200 mL) is added followed by 25 mL of concentrated hydrochloric acid. The solution is heated to 90° C. and stirred for two hours. After cooling to room temperature, the solution is concentrated under reduced pressure then basified to pH 9 with saturated aqueous $NaHCO_3$. The aqueous layer is extracted with ethyl acetate, and the organic extracts are combined and washed with saturated aqueous $NaHCO_3$ and brine. The organic extracts are dried over $Na_2SO_4$, filtered, and concentrated under reduced pressure. Purification by short-filtration ($SiO_2$, Hexanes:Ethyl acetate/1:1) gives 3 (3.1 g, 92%) as a white solid.

Synthesis of 2-Chloro-7-pyridin-2-yl-7H-pyrrolo-[2,3-d]pyrimidine 4: A suspension of 2-chloro-7H-pyrrolo-[2,3-d]pyrimidine 3 (0.53 g, 3.5 mmol), 2-bromopyridine (0.66 mL, 1.1 g, 6.9 mmol), copper(I) iodide (0.20 g, 1.0 mmol), trans-1,2-diaminocyclohexane (0.12 mL, 0.1 1g, 1.0 mmol), and potassium phosphate (2.2 g, 10 mmol) in 10 mL 1,4-dioxane is heated to 100° C. and stirred for four hours. The reaction mixture is cooled to room temperature, diluted with ethyl acetate, and washed with water and brine. The organic extract was dried over $MgSO_4$, filtered, and concentrated under reduced pressure. Purification by column chromatography ($SiO_2$, Hexane : Ethyl acetate/5:1) provided 4 (0.69 g, 87%) as a white solid.

Synthesis of (7-Pyridin-2-yl-7H-pyrrolo[2,3-d]pyrimidin-2-yl)-(3,4,5-trimethoxy-phenyl)-amine (5):

Method 1. To a solution of 2-chloro-7-pyridin-2-yl-7H-pyrrolo[2,3-d]pyrimidine in 1,4-dioxane is added 3,4,5-trimethoxy aniline (3 equivalents) followed by adding potassium tert-butoxide solution (1.0 M in tetrahydrofuran, 3 equivalents) dropwise. After addition, the reaction mixture is heated at 80° C. for 2 hours. The solvent is removed after cooling to room temperature. Purification by reverse phase HPLC gives (7-pyridin-2-yl-7H-pyrrolo[2,3-d]pyrimidin-2-yl)-(3,4,5-trimethoxy-phenyl)-amine as a white solid.

Method 2. A round bottle flask charged with 2-chloro-7-pyridin-2-yl-7H-pyrrolo[2,3-d]pyrimidine, 0.1 equivalents of tri(dibenzylideneacetone)dipalladium(0), 0.2 equivalents of biphenyl-2-yl-di-tert-butyl-phosphane, 3 equivalents of potassium phosphate and 1.5 equivalents of 3,4,5-trimethoxy aniline is flashed with nitrogen followed by the addition of 1,4-dioxane. The suspension is heated at 110° C. for 18 hours. Filtration through a pad of Celite removed the solid. The filtrate is diluted with ethyl acetate, and washed with water and brine. After drying over magnesium sulfate, the product is concentrated and purified by chromatography (ethyl acetate:

hexanes 1:1) to give 7-pyridin-2-yl-7H-pyrrolo[2,3-d]pyrimidin-2-yl)-(3,4,5-trimethoxy-phenyl)-amine as a white solid.

Example 2

3-[2-(3,4,5-trimethoxy-phenylamino)-pyrrolo[2,3-d]pyrimidin-7-yl]-benzoic acid

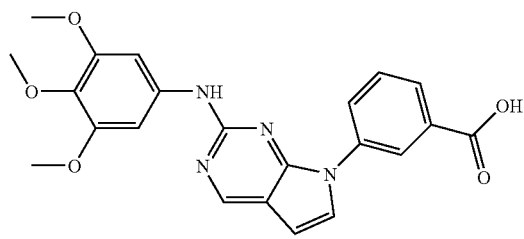

A solution of 3-[2-(3,4,5-trimethoxy-phenylamino)-pyrrolo[2,3-d]pyrimidin-7-yl]-benzoic acid methyl ester in 1N sodium hydroxide (methanol:water 1:1) is stirred at room temperature for 15 hours. Acidification with 1N hydrochloric acid to pH 6 gives a precipitate. Filtration and washing with water gives 3-[2-(3,4,5-trimethoxy-phenylamino)-pyrrolo[2,3-d]pyrimidin-7-yl]-benzoic acid as a white solid.

Example 3

3-[2-(3,4,5-Trimethoxy-phenylamino)-pyrrolo[2,3-d]pyrimidin-7-yl]-benzoyl chloride

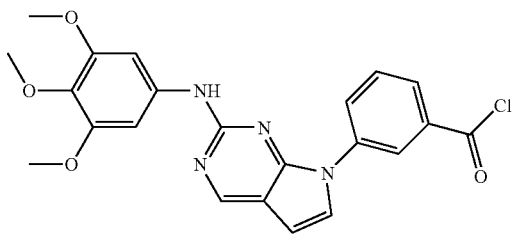

A dry round bottle flask charged with 3-[2-(3,4,5-trimethoxy-phenylamino)-pyrrolo[2,3-d]pyrimidin-7-yl]-benzoic acid is flushed with nitrogen, dichloromethane and a few drops of N,N'-dimethylformamide are added. Oxalyl chloride solution (2.0 M in dichloromethane) is added dropwise. The reaction mixture is stirred at room temperature for 30 minutes, resulting in a solution of 3-[2-(3,4,5-trimethoxy-phenolamino)-pyrrolo[2,3-d]pyrimidin-7-yl]-benzoyl chloride.

Example 4

N-Methyl-3-[2-(3,4,5-trimethoxy-phenylamino)-pyrrolo[2,3-d]pyrimidin-7-yl]-benzamide

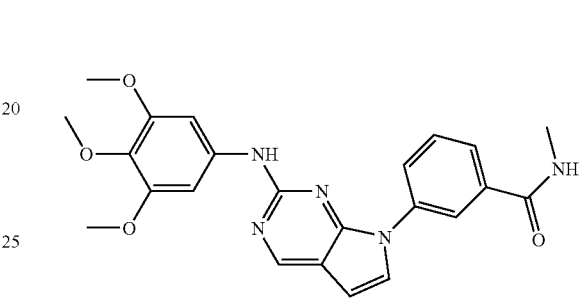

To a solution of 3-[2-(3,4,5-trimethoxy-phenylamino)-pyrrolo[2,3-d]pyrimidin-7-yl]-benzoyl chloride in dichloromethane is added 5 equivalents of methylamine solution (2.0 M in tetrahydrofuran). After stirring at room temperature for 1 hour, the reaction is quenched with water. Removal of the solvent followed by purification with reverse phase HPLC gives N-methyl-3-[2-(3,4,5-trimethoxy-phenylamino)-pyrrolo[2,3-d]pyrimidin-7-yl]-benzamide as a white solid.

By repeating the procedures described in the above examples, using appropriate starting materials, the following compounds of Formula I, as identified in Table 1, are obtained.

TABLE 1

| Compound Number | Structure | Physical Data $^1$H NMR and MS (m/z) |
|---|---|---|
| 1 | 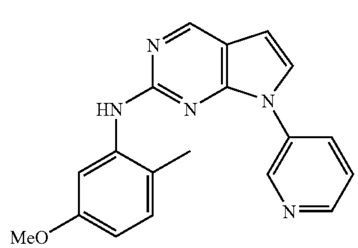 | MS (m/z) 332.3 (M + 1) |

TABLE 1-continued
| Compound Number | Structure | Physical Data $^1$H NMR and MS (m/z) |
|---|---|---|
| 2 | 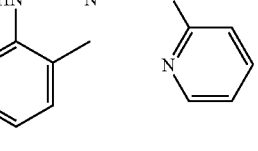 | MS (m/z) 332.2 (M + 1) |
| 3 | 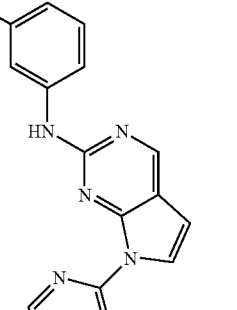 | MS (m/z) 302.2 (M + 1) |
| 4 | 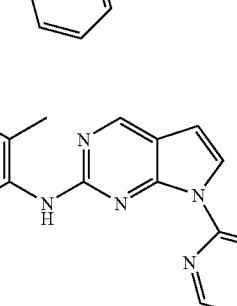 | MS (m/z) 376.3 (M + 1) |
| 5 | 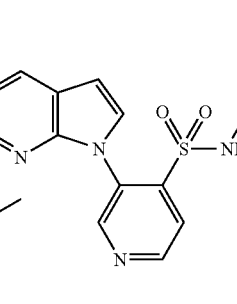 | MS (m/z) 452.2 (M + 1) |
| 6 | 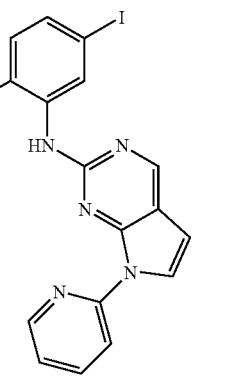 | MS (m/z) 428.1 (M + 1) |

TABLE 1-continued

| Compound Number | Structure | Physical Data $^1$H NMR and MS (m/z) |
|---|---|---|
| 7 | *[structure: 4-iodo-2-methylphenyl-amino pyrrolopyrimidine with pyridin-2-yl]* | MS (m/z) 428.1 (M + 1) |
| 8 | *[structure: hydroxymethyl-methylphenyl-amino pyrrolopyrimidine with pyridin-2-yl]* | MS (m/z) 332.2 (M + 1) |
| 9 | *[structure: hydroxy-methylphenyl-amino pyrrolopyrimidine with pyridin-2-yl]* | $^1$H NMR 400 MHz (CDCl$_3$) δ 8.68 (s, 1H), 8.32 (m, 2H), 8.05 (d, 1H), 7.73 (m, 1H), 7.14 (m, 1H), 6.80 (d, 1H), 6.62 (d, 1H), 6.36 (d, 1H), 6.23 (m, 1H); MS (m/z) 318.2 (M + 1). |
| 10 | *[structure: hydroxy-methylphenyl-amino pyrrolopyrimidine with N-propylsulfonamide phenyl]* | $^1$HNMR 400 MHz (CDCl$_3$) δ 10.35 (s, 1H), 8.52 (s, 1H), 8.07 (dd, 1H), 7.70 (m, 2H), 7.37 (dd, 1H), 7.24 (d, 1H), 7.10 (d, 1H), 6.94 (d, 1H), 6.68 (d, 1H), 6.52 (dd, 1H), 5.28 (b, 1H), 3.02 (m, 2H), 2.16 (s, 3H), 1.27 (m, 2H), 0.76 (t, 3H); MS (m/z) 438.2 (M + 1). |

TABLE 1-continued

| Compound Number | Structure | Physical Data $^1$H NMR and MS (m/z) |
|---|---|---|
| 11 | 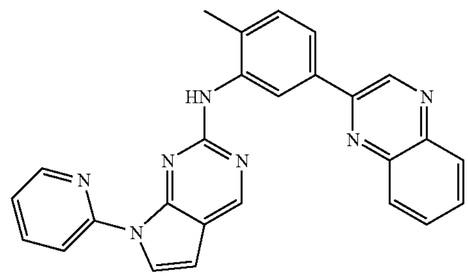 | MS (m/z) 430.2 (M + 1). |
| 12 | 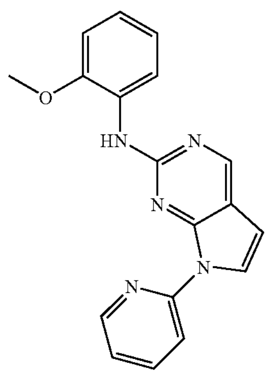 | MS (m/z) 418.2 (M + 1). |
| 13 | 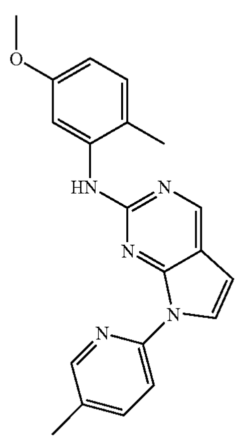 | MS (m/z) 436.2 (M + 1). |
| 14 | 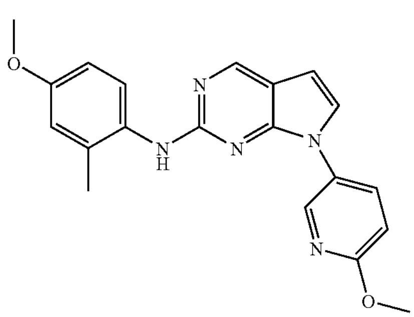 | MS (m/z) 362.3 (M + 1). |

TABLE 1-continued

| Compound Number | Structure | Physical Data ¹H NMR and MS (m/z) |
|---|---|---|
| 15 | 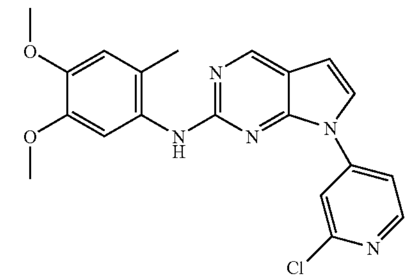 | MS (m/z) 396.2 (M + 1). |
| 16 | 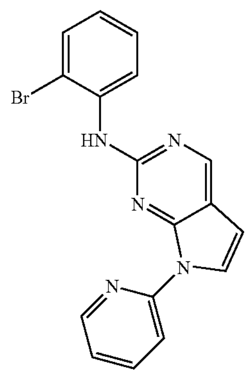 | MS (m/z) 366.1 (M + 1). |
| 17 | 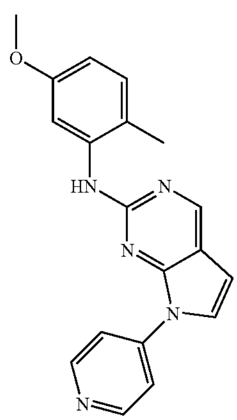 | MS (m/z) 332.3 (M + 1). |
| 18 | 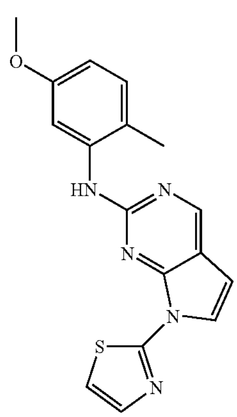 | MS (m/z) 338.3 (M + 1). |

TABLE 1-continued

| Compound Number | Structure | Physical Data ¹H NMR and MS (m/z) |
| --- | --- | --- |
| 19 | 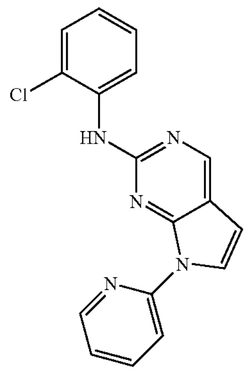 | MS (m/z) 306.2 (M + 1). |
| 20 | 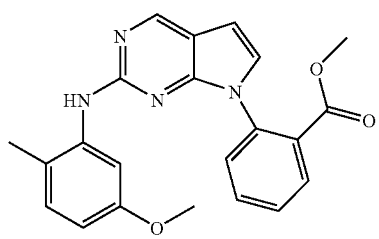 | MS (m/z) 389.2 (M + 1). |
| 21 | 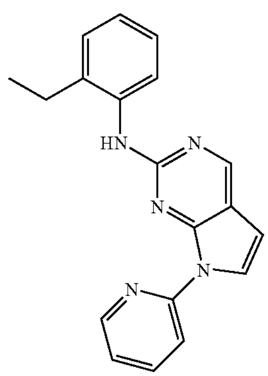 | MS (m/z) 316.2 (M + 1). |
| 22 | 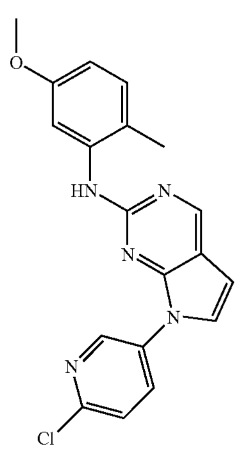 | MS (m/z) 366.1 (M + 1). |

TABLE 1-continued

| Compound Number | Structure | Physical Data<br>¹H NMR and MS (m/z) |
| --- | --- | --- |
| 23 | 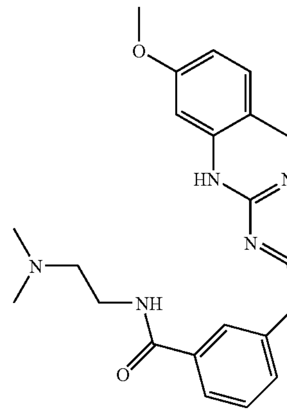 | MS (m/z) 445.2 (M + 1). |
| 24 | 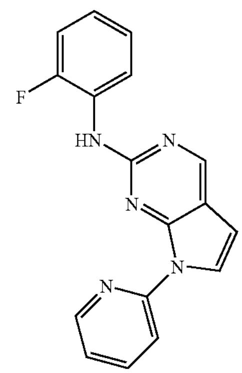 | MS (m/z) 306.1 (M + 1). |
| 25 | 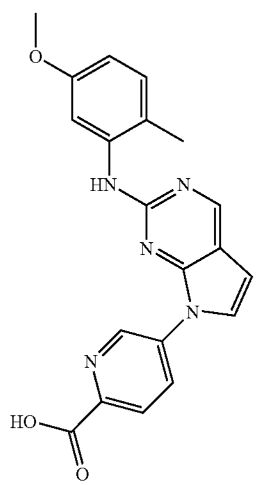 | MS (m/z) 375.2 (M + 1). |
| 26 | 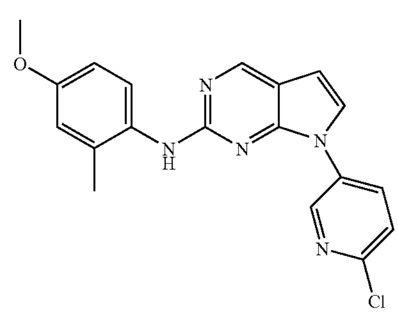 | MS (m/z) 366.1 (M + 1). |

TABLE 1-continued

| Compound Number | Structure | Physical Data $^1$H NMR and MS (m/z) |
|---|---|---|
| 27 | 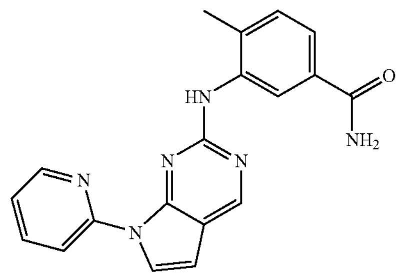 | MS (m/z) 345.2 (M + 1). |
| 28 | 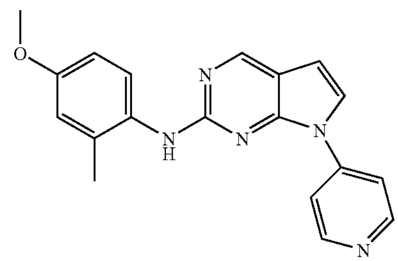 | MS (m/z) 332.1 (M + 1). |
| 29 | 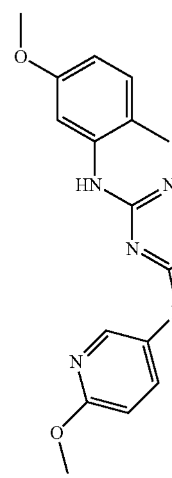 | MS (m/z) 362.2 (M + 1). |
| 30 | 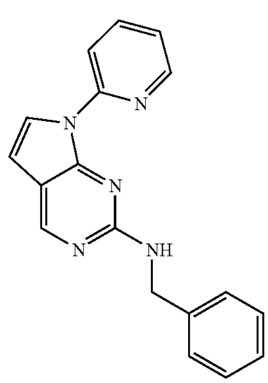 | MS (m/z) 302.1 (M + 1). |

TABLE 1-continued

| Compound Number | Structure | Physical Data<br>¹H NMR and MS (m/z) |
|---|---|---|
| 31 | 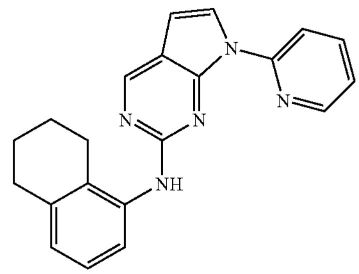 | MS (m/z) 342.2 (M + 1). |
| 32 | 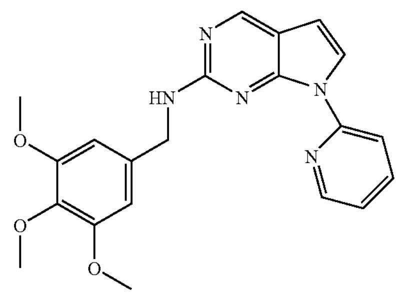 | MS (m/z) 392.2 (M + 1). |
| 33 | 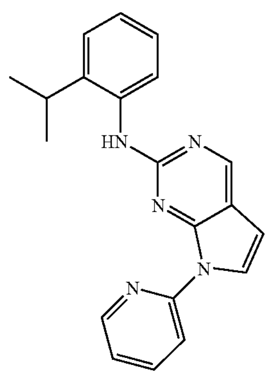 | MS (m/z) 330.2 (M + 1). |
| 34 | 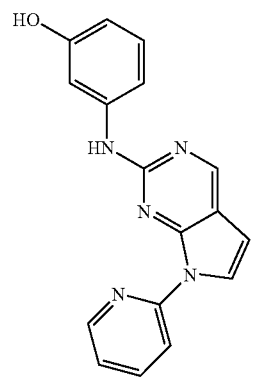 | MS (m/z) 304.1 (M + 1). |

TABLE 1-continued
| Compound Number | Structure | Physical Data <br> ¹H NMR and MS (m/z) |
|---|---|---|
| 35 | 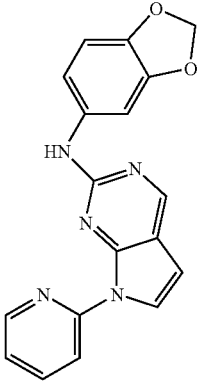 | MS (m/z) 332.1 (M + 1). |
| 36 | 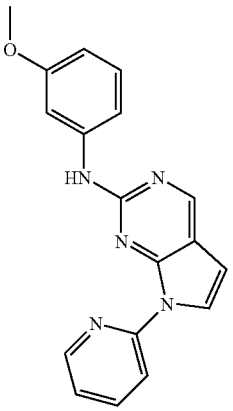 | MS (m/z) 318.1 (M + 1). |
| 37 | 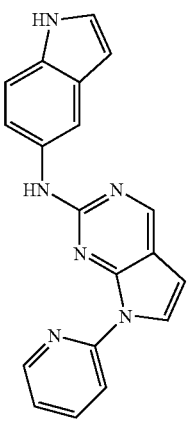 | MS (m/z) 327.1 (M + 1). |

TABLE 1-continued
| Compound Number | Structure | Physical Data $^1$H NMR and MS (m/z) |
|---|---|---|
| 38 | 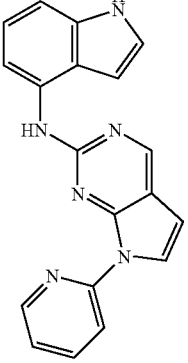 | MS (m/z) 327.1 (M + 1). |
| 39 | 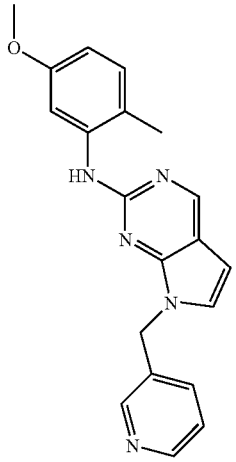 | MS (m/z) 346.2 (M + 1). |
| 40 | 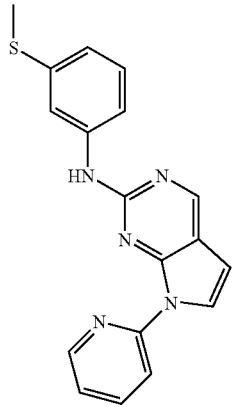 | MS (m/z) 334.1 (M + 1). |

TABLE 1-continued

| Compound Number | Structure | Physical Data<br>¹H NMR and MS (m/z) |
|---|---|---|
| 41 | 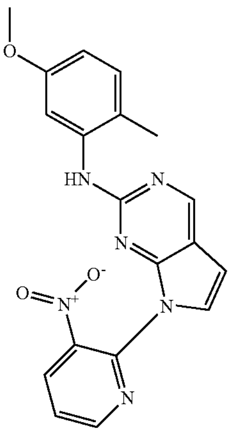 | MS (m/z) 377.1 (M + 1). |
| 42 | 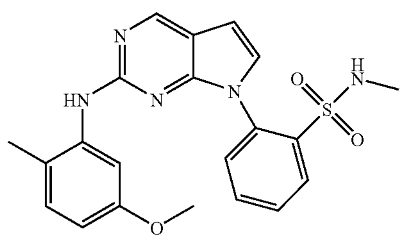 | MS (m/z) 424.2 (M + 1). |
| 43 | 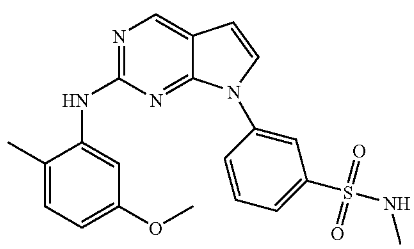 | MS (m/z) 424.2 (M + 1). |
| 44 | 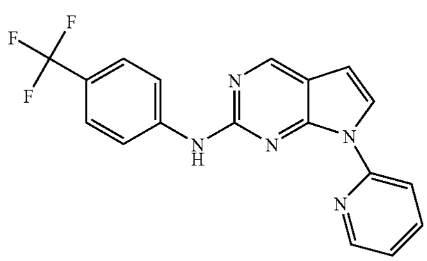 | MS (m/z) 356.1 (M + 1). |

TABLE 1-continued
| Compound Number | Structure | Physical Data $^1$H NMR and MS (m/z) |
|---|---|---|
| 45 | 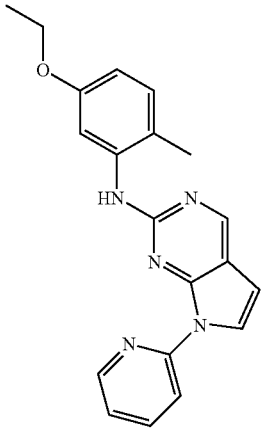 | MS (m/z) 346.2 (M + 1). |
| 46 | 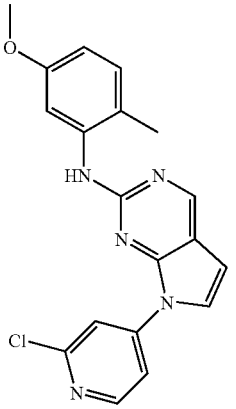 | MS (m/z) 366.1 (M + 1). |
| 47 | 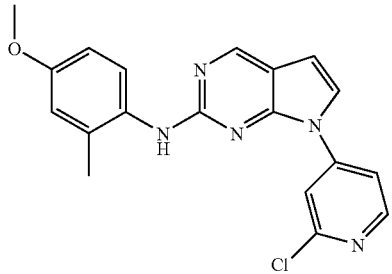 | MS (m/z) 366.1 (M + 1). |
| 48 | 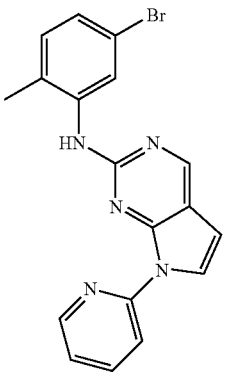 | MS (m/z) 380.1 (M + 1). |

TABLE 1-continued

| Compound Number | Structure | Physical Data<br>$^1$H NMR and MS (m/z) |
| --- | --- | --- |
| 49 | 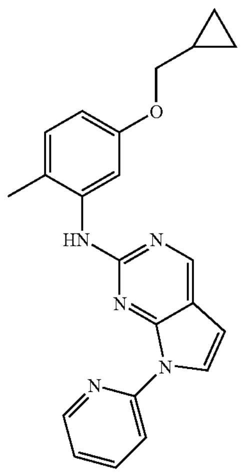 | MS (m/z) 372.2 (M + 1). |
| 50 | 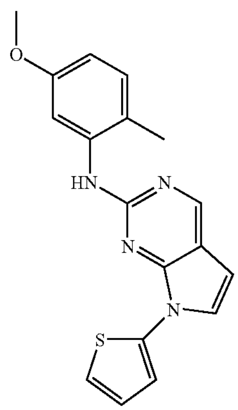 | MS (m/z) 337.1 (M + 1). |
| 51 | 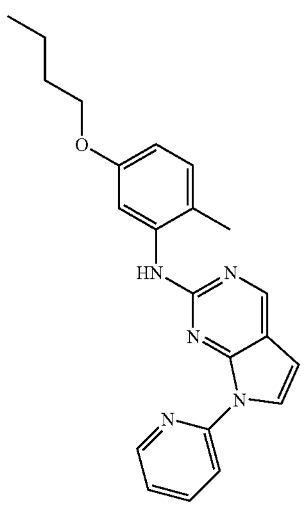 | MS (m/z) 374.2 (M + 1). |

TABLE 1-continued
| Compound Number | Structure | Physical Data $^1$H NMR and MS (m/z) |
|---|---|---|
| 52 | 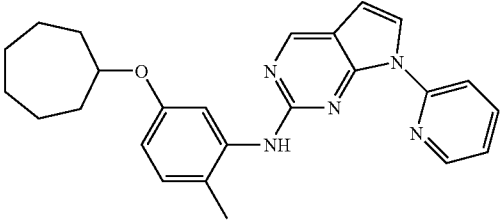 | MS (m/z) 414.2 (M + 1). |
| 53 | 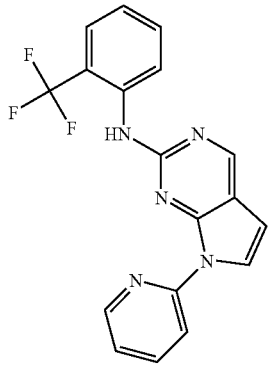 | MS (m/z) 356.1 (M + 1). |
| 54 | 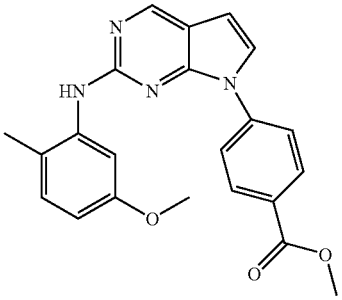 | MS (m/z) 389.2 (M + 1). |
| 55 | 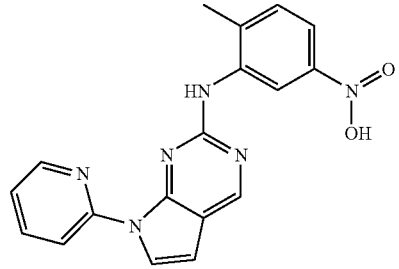 | MS (m/z) 347.2 (M + 1). |
| 56 | 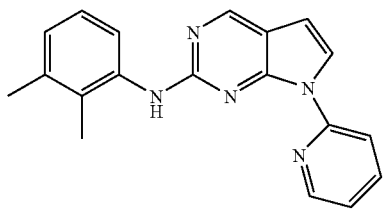 | MS (m/z) 316.2 (M + 1). |

TABLE 1-continued

| Compound Number | Structure | Physical Data <br> ¹H NMR and MS (m/z) |
| --- | --- | --- |
| 57 | 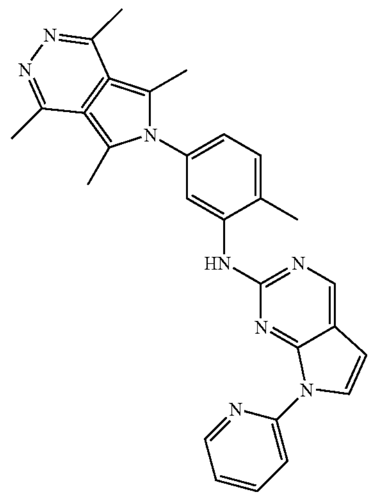 | MS (m/z) 475.2 (M + 1). |
| 58 | 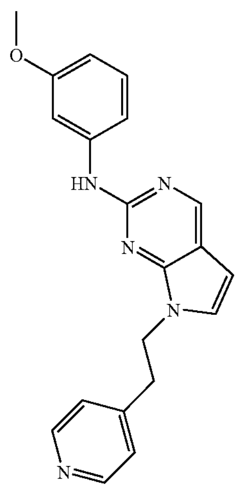 | MS (m/z) 360.2 (M + 1). |
| 59 | 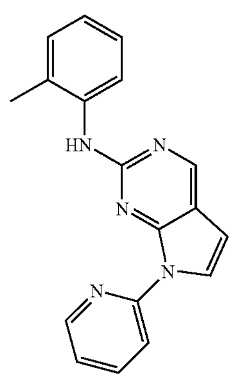 | MS (m/z) 302.2 (M + 1). |

TABLE 1-continued

| Compound Number | Structure | Physical Data $^1$H NMR and MS (m/z) |
|---|---|---|
| 60 | 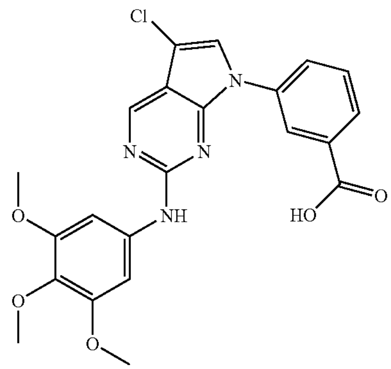 | MS (m/z) 375.2 (M + 1). |
| 61 | 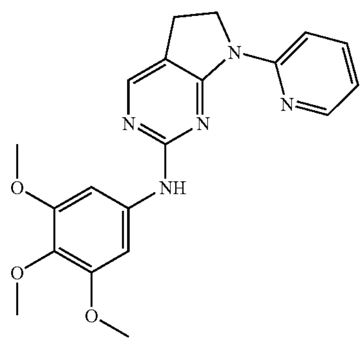 | MS (m/z) 379.9 (M + 1). |
| 62 | 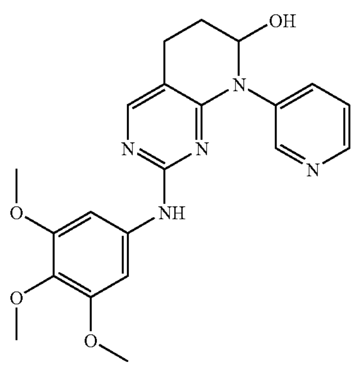 | MS (m/z) 410.5 (M + 1). |
| 63 | 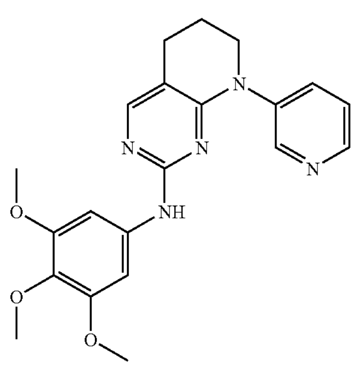 | MS (m/z) 394.4 (M + 1). |

TABLE 1-continued

| Compound Number | Structure | Physical Data<br>¹H NMR and MS (m/z) |
| --- | --- | --- |
| 64 | 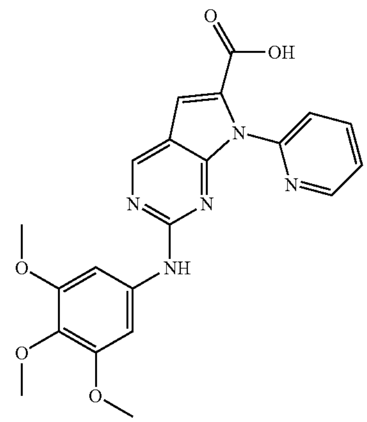 | MS (m/z) 422.1 (M + 1). |
| 65 | 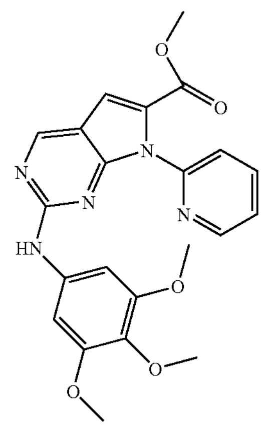 | MS (m/z) 436.2 (M + 1). |
| 66 | 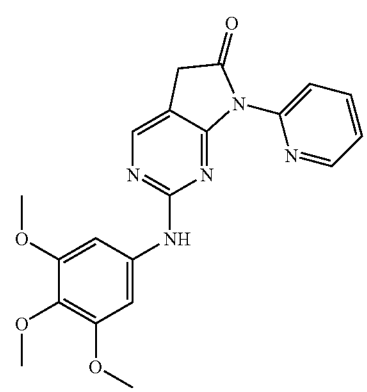 | MS (m/z) 394.4 (M + 1). |
| 67 | 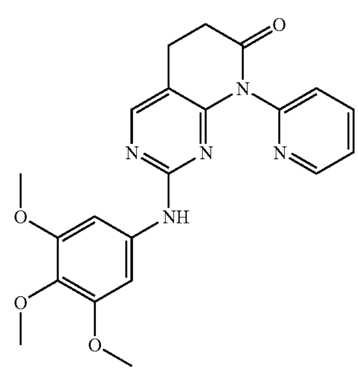 | MS (m/z) 408.4 (M + 1). |

TABLE 1-continued

| Compound Number | Structure | Physical Data <br> ¹H NMR and MS (m/z) |
|---|---|---|
| 68 | 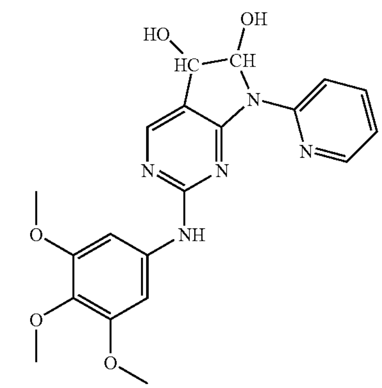 | MS (m/z) 412.2 (M + 1). |
| 69 | 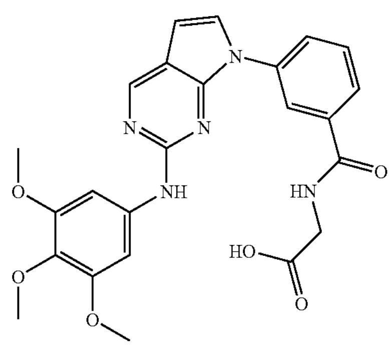 | MS (m/z) 477.8 (M + 1). |
| 70 | 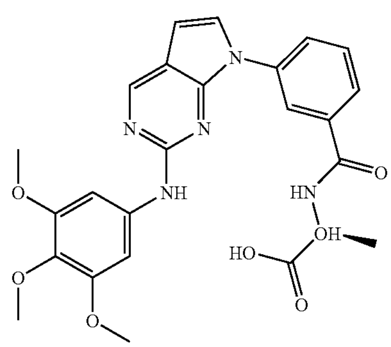 | MS (m/z) 492.2 (M + 1). |
| 71 | 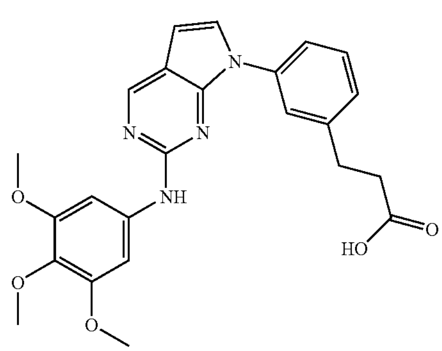 | ¹H NMR 400 MHz (DMSO-d₆) δ 9.31 (s, 1H), 8.75 (s, 1H), 7.65 (m, 1H), 7.53 (s, 1H), 7.51 (d, 1H), 7.39 (t, 1H), 7.21 (m, 1H), 7.13 (s, 2H), 6.61 (d, 1H), 5.83 (s, 1H), 3.53 (d, 9H), 2.85 (m, 2H), 2.54 (m, 2H); MS (m/z) 449.0 (M + 1). |

TABLE 1-continued

| Compound Number | Structure | Physical Data $^1$H NMR and MS (m/z) |
|---|---|---|
| 72 | 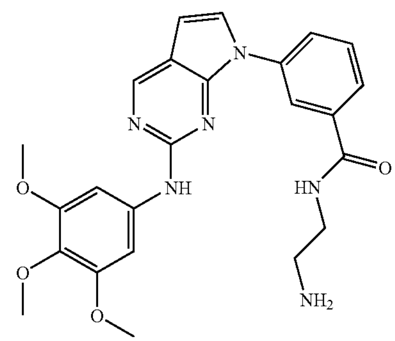 | MS (m/z) 463.2 (M + 1). |
| 73 | 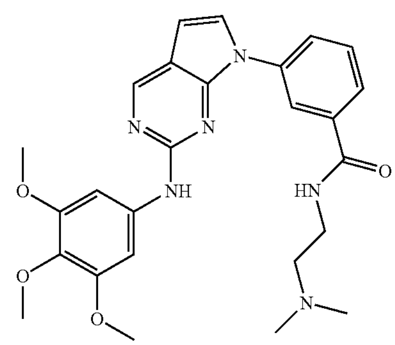 | MS (m/z) 491.2 (M + 1). |
| 74 | 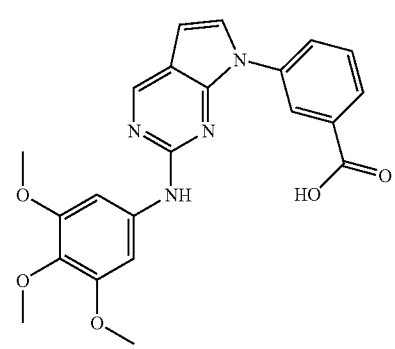 | $^1$H NMR 400 MHz (DMSO-d$_6$) δ 9.30 (s, 1H), 8.73 (s, 1H), 8.13 (m, 1H), 8.02 (m, 1H), 7.87 (m, 1H), 7.59 (t, 1H), 7.55 (d, 1H), 7.09 (s, 2H), 6.61 (d, 1H), 5.77 (s, 1H), 3.48 (d, 9H); MS (m/z) 421.1 (M + 1). |
| 75 | 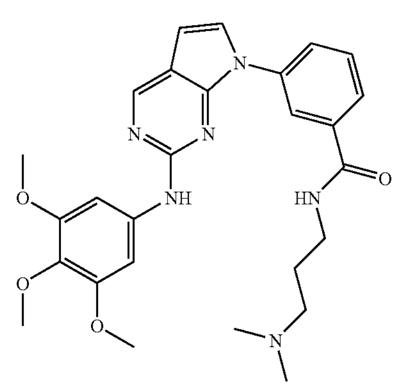 | MS (m/z) 505.3 (M + 1). |

TABLE 1-continued

| Compound Number | Structure | Physical Data $^1$H NMR and MS (m/z) |
|---|---|---|
| 76 | 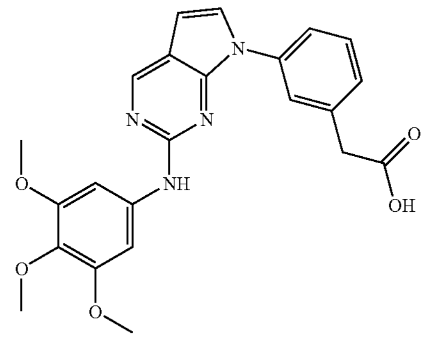 | $^1$H NMR 400 MHz (DMSO-d$_6$) δ 9.35 (s, 1H), 8.80 (s, 1H), 7.73 (d, 1H), 7.60 (s, 1H), 7.53 (d, 1H), 7.45 (t, 1H), 7.28 (d, 1H), 7.19 (s, 2H), 6.67 (d, 1H), 3.59 (m, 11H); MS (m/z) 435.2 (M + 1). |
| 77 | 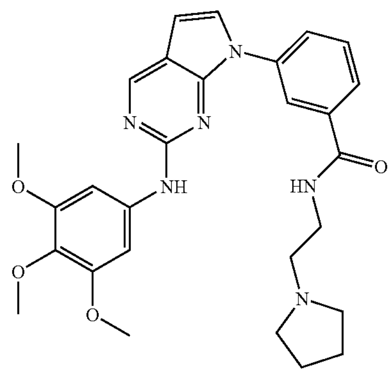 | MS (m/z) 516.3 (M + 1). |
| 78 | 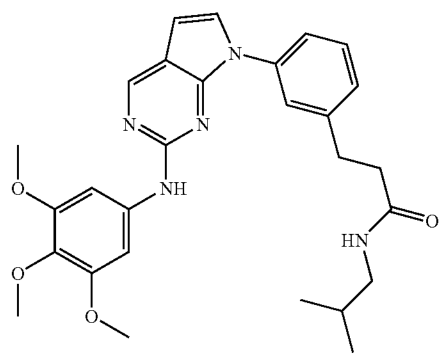 | MS (m/z) 504.3 (M + 1). |
| 79 | 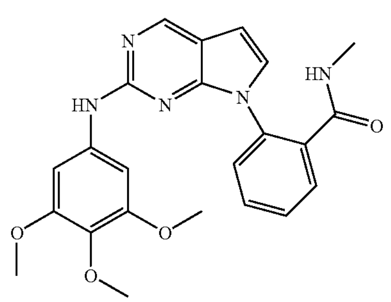 | MS (m/z) 434.2 (M + 1). |

TABLE 1-continued

| Compound Number | Structure | Physical Data<br>¹H NMR and MS (m/z) |
|---|---|---|
| 80 | 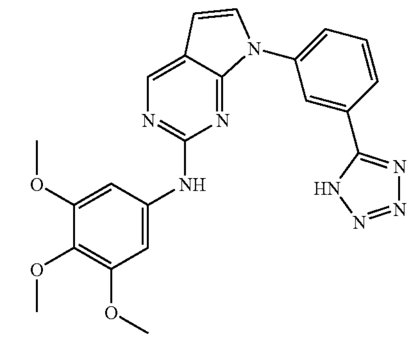 | ¹H NMR 400 MHz (MeOH-d₄) δ 8.76 (s, 1H), 8.57 (t, 1H), 8.10 (m, 1H), 8.02 (m, 1H), 7.77 (m, 2H), 6.97 (s, 2H), 6.86 (d, 1H), 3.69 (d, 9H); MS (m/z) 445.2 (M + 1). |
| 81 | 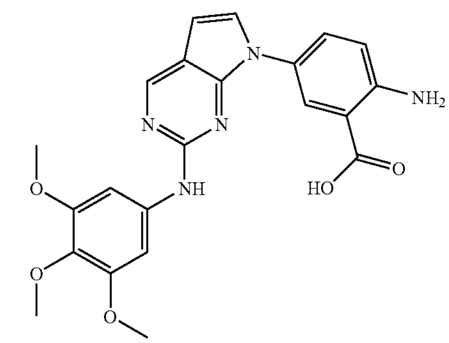 | MS (m/z) 436.2 (M + 1). |
| 82 | 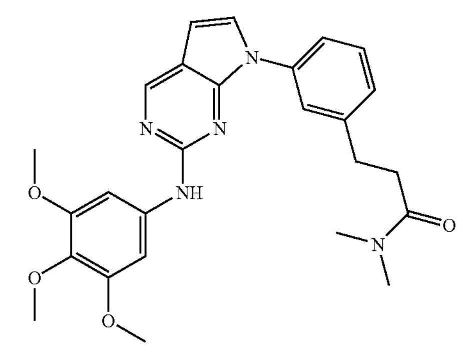 | MS (m/z) 476.2 (M + 1). |
| 83 | 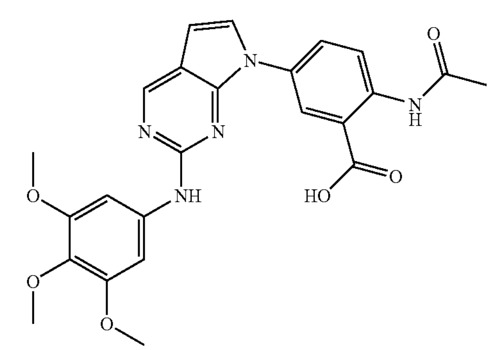 | ¹H NMR 400 MHz (DMSO-d₆) δ 11.17 (s, 1H), 9.53 (s, 1H), 8.94 (s, 1H), 8.72 (m, 1H), 8.33 (d, 1H), 8.17 (m, 1H), 7.71 (d, 1H), 7.32 (s, 2H), 6.81 (d, 1H), 3.72 (d, 9H), 2.33 (s, 3H); MS (m/z) 478.2 (M + 1). |

TABLE 1-continued

| Compound Number | Structure | Physical Data $^1$H NMR and MS (m/z) |
|---|---|---|
| 84 | 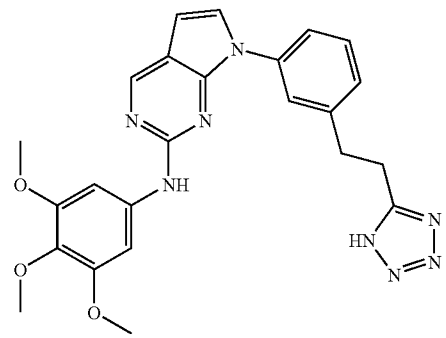 | $^1$H NMR 400 MHz (CDCl$_3$) δ 11.6 (s, 1H), 8.48 (s, 1H), 7.69 (m, 1H), 7.46 (m, 2H), 7.33 (m, 1H), 7.25 (m, 1H), 6.73 (m, 3H), 3.98 (s, 3H), 3.66 (d, 6H), 3.09 (m, 2H), 2.92 (m, 2H); MS (m/z) 473.3 (M + 1). |
| 85 | 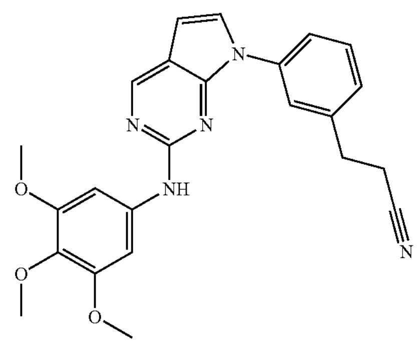 | $^1$H NMR 400 MHz (CDCl$_3$) δ 8.74 (s, 1H), 7.70 (m, 1H), 7.49 (t, 1H), 7.27 (d, 1H), 7.23 (m, 1H), 6.98 (d, 2H), 6.61 (d, 1H), 3.91 (s, 3H), 3.77 (s, 6H), 3.07 (m, 2H), 2.70 (m, 2H); MS (m/z) 430.2 (M + 1). |
| 86 | 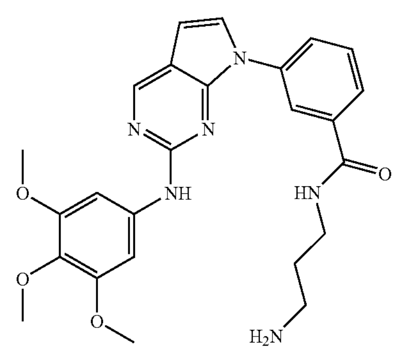 | MS (m/z) 477.2 (M + 1). |
| 87 | 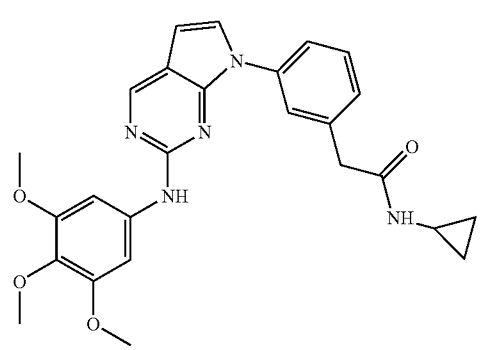 | MS (m/z) 474.2 (M + 1). |

TABLE 1-continued

| Compound Number | Structure | Physical Data<br>¹H NMR and MS (m/z) |
|---|---|---|
| 88 | 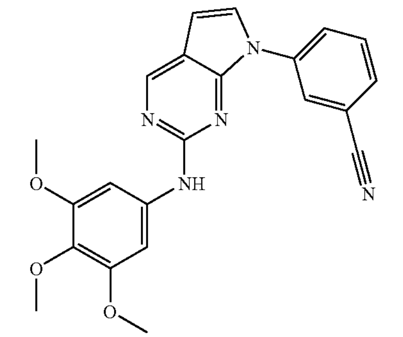 | ¹HNMR 400 MHz (CDCl₃) δ 8.67 (s, 1H), 8.02 (m, 2H), 7.55 (m, 2H), 7.16 (d. 1H), 6.86 (s, 2H), 6.56 (d, 1H), 3.85 (s, 3H), 3.72 (s, 6H); MS (m/z) 402.1 (M + 1). |
| 89 | 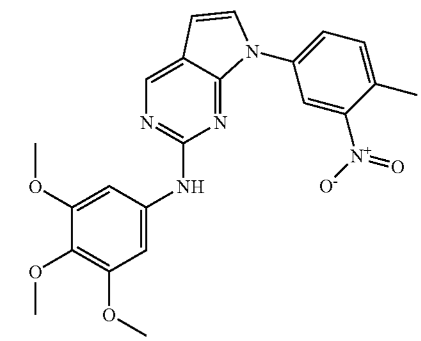 | MS (m/z) 436.1 (M + 1). |
| 90 | 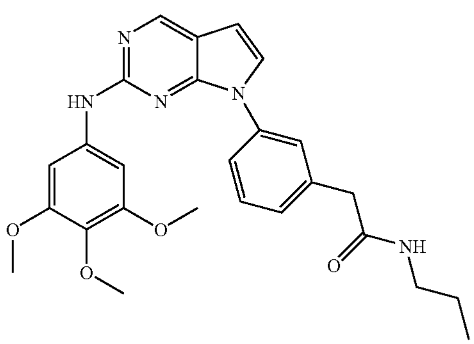 | MS (m/z) 476.2 (M + 1). |
| 91 | 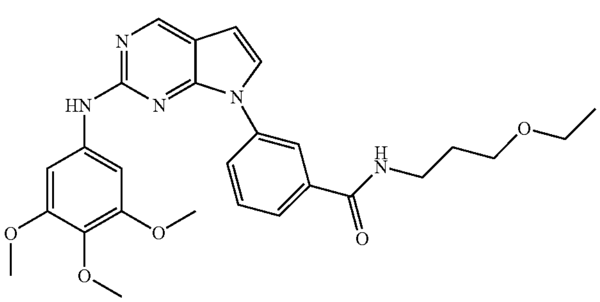 | MS (m/z) 506.3 (M + 1). |

TABLE 1-continued
| Compound Number | Structure | Physical Data $^1$H NMR and MS (m/z) |
|---|---|---|
| 92 | 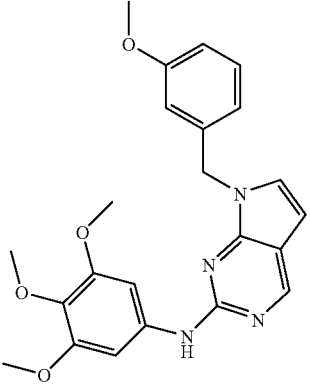 | MS (m/z) 421.2 (M + 1). |
| 93 | 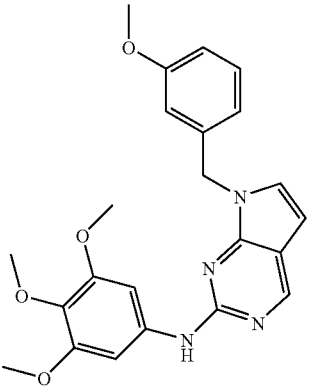 | MS (m/z) 421.2 (M + 1). |
| 94 | 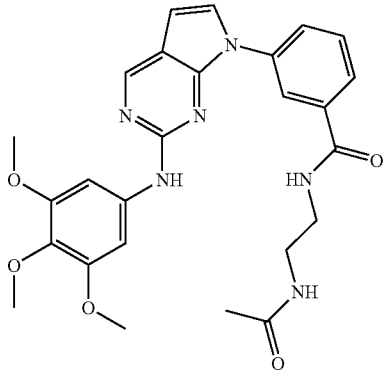 | MS (m/z) 505.3 (M + 1). |
| 95 | 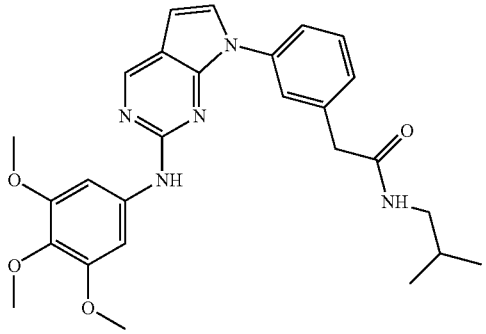 | MS (m/z) 490.2 (M + 1). |

TABLE 1-continued

| Compound Number | Structure | Physical Data ¹H NMR and MS (m/z) |
| --- | --- | --- |
| 96 | 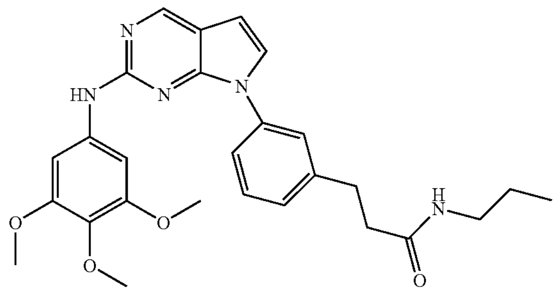 | MS (m/z) 490.2 (M + 1). |
| 97 | 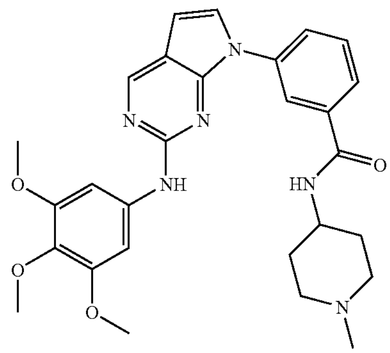 | MS (m/z) 517.3 (M + 1). |
| 98 | 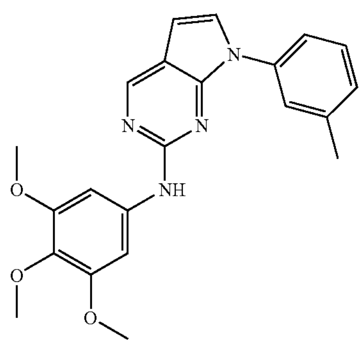 | MS (m/z) 391.2 (M + 1). |
| 99 | 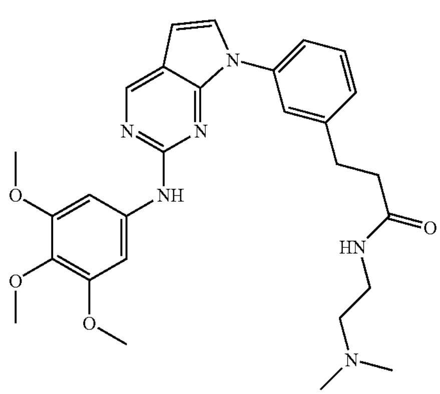 | MS (m/z) 519.3 (M + 1). |

TABLE 1-continued

| Compound Number | Structure | Physical Data ¹H NMR and MS (m/z) |
|---|---|---|
| 100 | 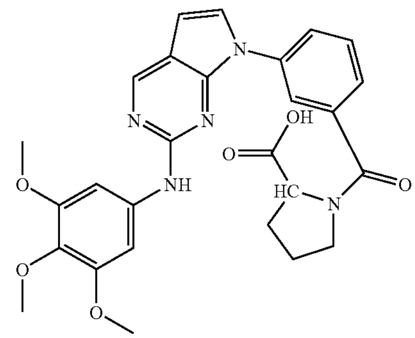 | MS (m/z) 518.2 (M + 1). |
| 101 | 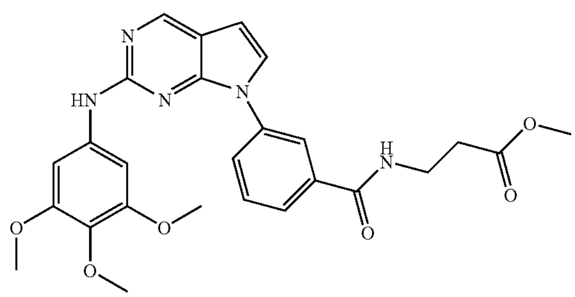 | MS (m/z) 506.2 (M + 1). |
| 102 | 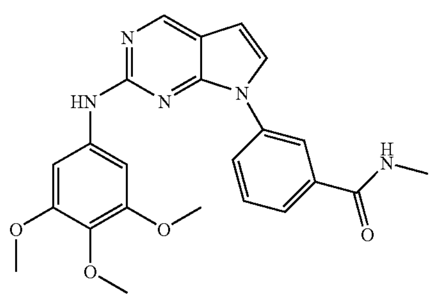 | MS (m/z) 434.2 (M + 1). |
| 103 | 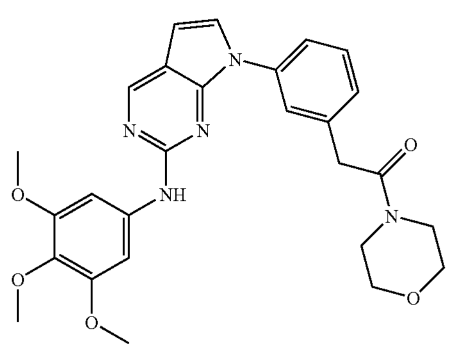 | MS (m/z) 504.2 (M + 1). |

TABLE 1-continued

| Compound Number | Structure | Physical Data <br> ¹H NMR and MS (m/z) |
|---|---|---|
| 104 | 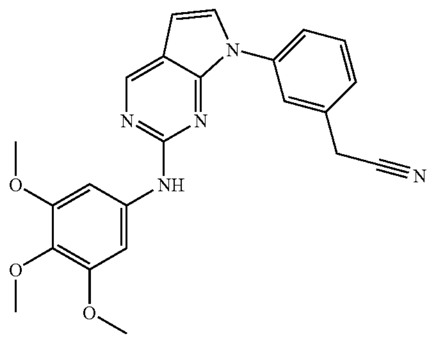 | ¹H NMR 400 MHz (CDCl₃) δ 8.87 (s, 1H), 7.92 (m, 1H), 7.86 (m, 1H), 7.66 (t, 1H), 7.48 (m, 1H), 7.39 (d, 1H), 7.22 (s, 1H), 7.09 (s, 2H), 6.75 (d, 1H), 3.96 (s, 3H), 3.88 (s, 6H), MS (m/z) 415.9 (M + 1). |
| 105 | 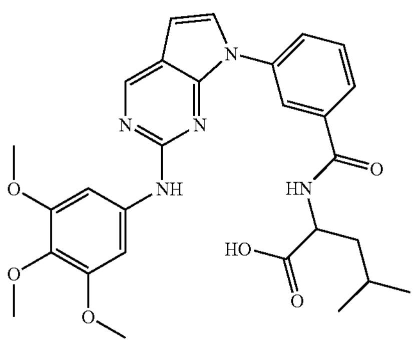 | MS (m/z) 534.2 (M + 1). |
| 106 | 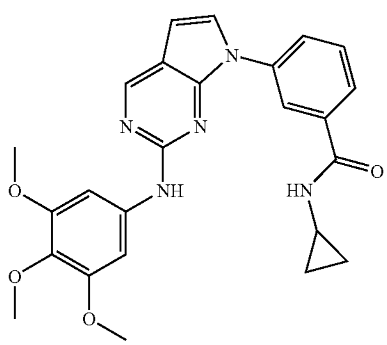 | MS (m/z) 460.2 (M + 1). |
| 107 | 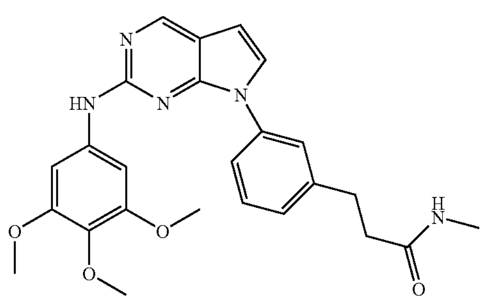 | MS (m/z) 462.2 (M + 1). |

TABLE 1-continued

| Compound Number | Structure | Physical Data <sup>1</sup>H NMR and MS (m/z) |
|---|---|---|
| 108 | 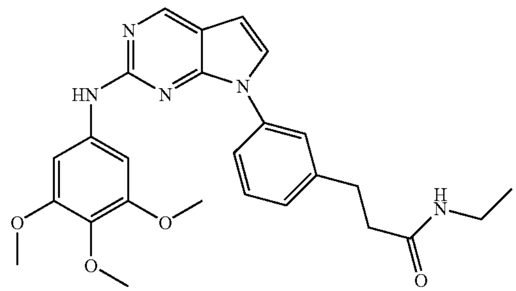 | MS (m/z) 476.2 (M + 1). |
| 109 | 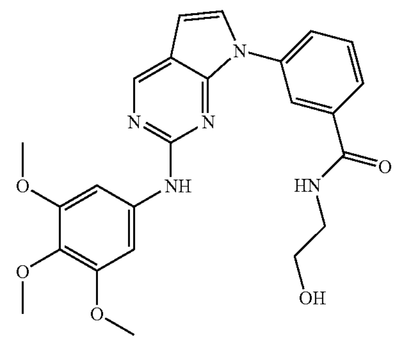 | MS (m/z) 464.2 (M + 1). |
| 110 | 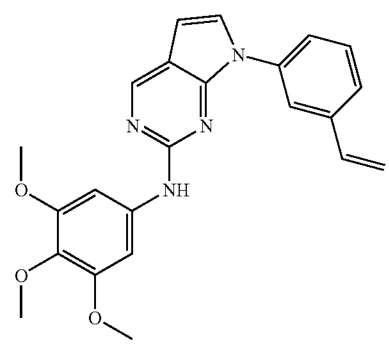 | MS (m/z) 445.1 (M + 1). |
| 111 | 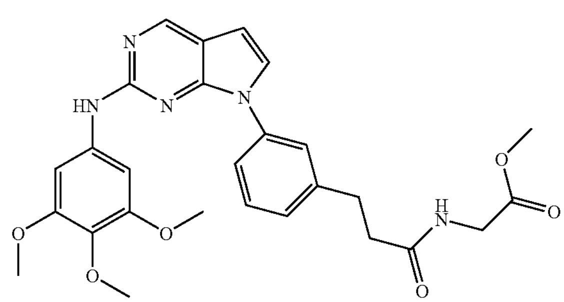 | MS (m/z) 520.2 (M + 1). |

TABLE 1-continued

| Compound Number | Structure | Physical Data <sup>1</sup>H NMR and MS (m/z) |
|---|---|---|
| 112 | 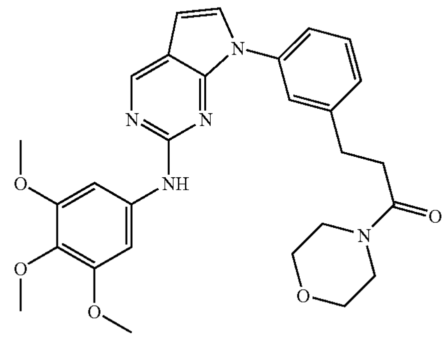 | MS (m/z) 517.2 (M + 1). |
| 113 | 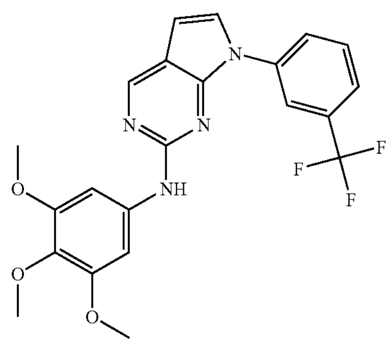 | MS (m/z) 403.2 (M + 1). |
| 114 | 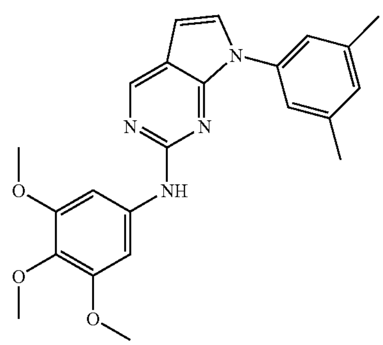 | MS (m/z) 405.2 (M + 1). |
| 115 | 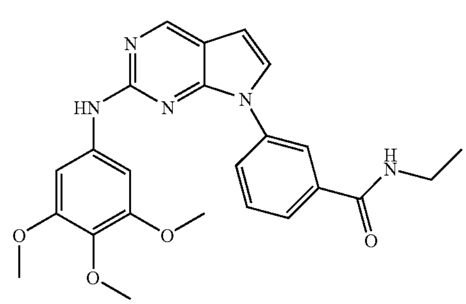 | MS (m/z) 475.2 (M + 1). |

TABLE 1-continued

| Compound Number | Structure | Physical Data $^1$H NMR and MS (m/z) |
|---|---|---|
| 116 | 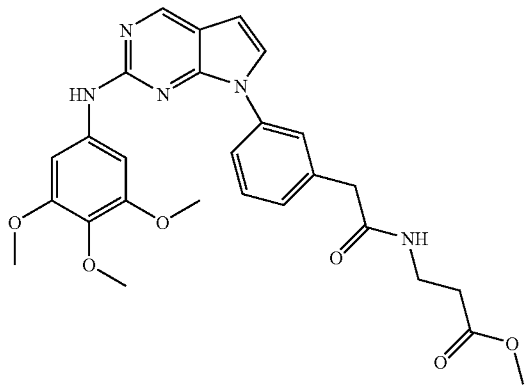 | MS (m/z) 520.2 (M + 1). |
| 117 | 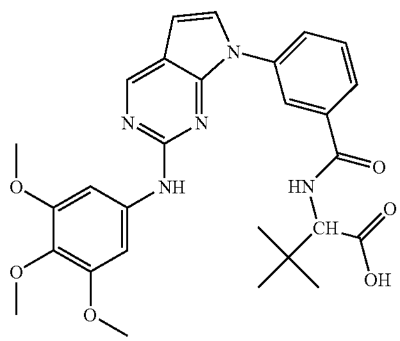 | MS (m/z) 534.2 (M + 1). |
| 118 | 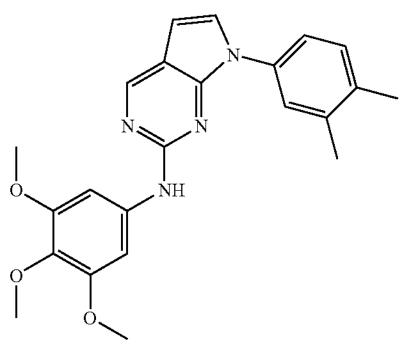 | MS (m/z) 405.2 (M + 1). |
| 119 | 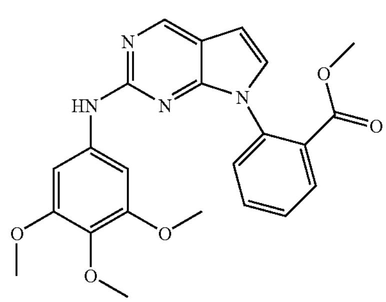 | MS (m/z) 419.2 (M + 1). |

TABLE 1-continued

| Compound Number | Structure | Physical Data <br> ¹H NMR and MS (m/z) |
| --- | --- | --- |
| 120 | 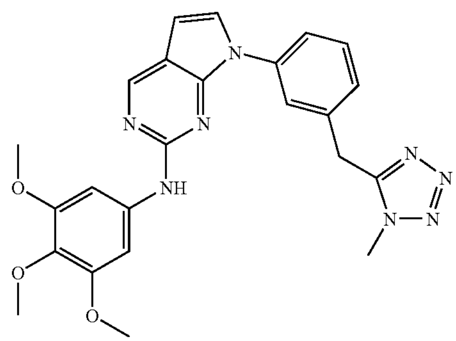 | ¹H NMR 400 MHz (MeOH-d₄) δ 8.61 (s, 1H), 7.64 (m, 2H), 7.49 (d, 1H), 7.43 (t, 1H), 7.22 (d, 1H), 6.90 (s, 2H), 6.63 (d, 1H), 4.31 (s, 2H), 3.90 (s, 3H), 3.62 (s, 3H), 3.56 (s, 6H); MS (m/z) 473.5 (M + 1). |
| 121 | 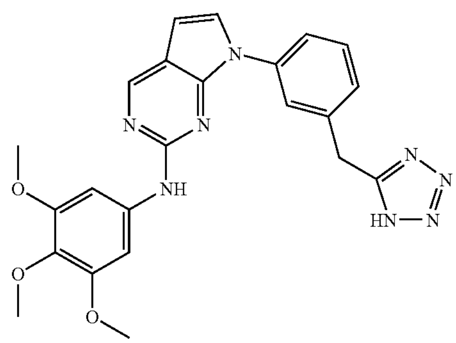 | ¹H NMR 400 MHz (MeOH-d₄) δ 8.62 (s, 1H), 7.65 (m, 1H), 7.63 (m, 1H), 7.54 (d, 1H), 7.43 (m, 1H), 7.26 (m, 1H), 6.86 (s, 2H), 6069 (d, 1H), 4.31 (s, 2H), 3.63 (s, 3H), 3.58 (s, 6H); MS (m/z) 415.9 (M+1). MS (m/z) 459.2 (M + 1). |
| 122 | 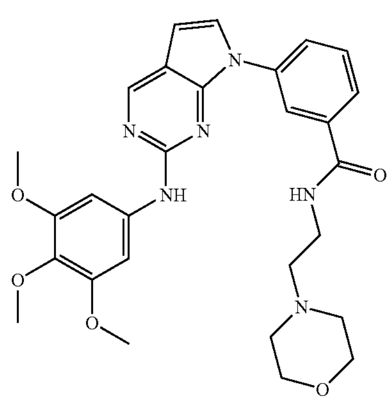 | MS (m/z) 533.2 (M + 1). |
| 123 | 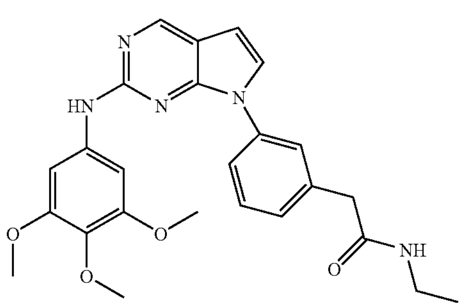 | MS (m/z) 462.2 (M + 1). |

TABLE 1-continued

| Compound Number | Structure | Physical Data <br> ¹H NMR and MS (m/z) |
| --- | --- | --- |
| 124 | 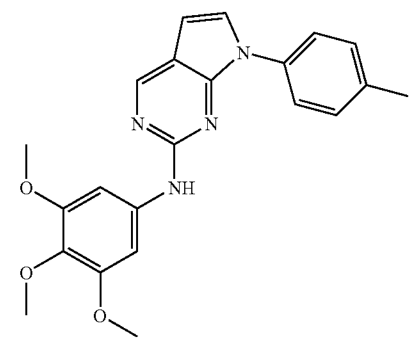 | MS (m/z) 391.2 (M + 1). |
| 125 | 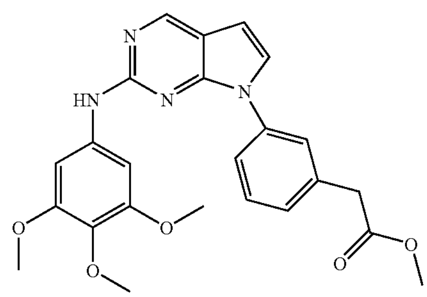 | ¹H NMR 400 MHz (CDCl₃) δ 8.78 (s, 1H), 7.71 (m, 1H), 7.56 (m, 1H), 7.44 (t, 1H), 7.27 (m, 1H), 7.21 (d, 1H), 7.13 (b, 1H), 6.95 (s, 2H), 6.57 (d, 1H), 3.80 (s, 2H), 3.79 (s, 3H), 3.70 (m, 9H); MS (m/z) 449.3 (M + 1). |
| 126 | 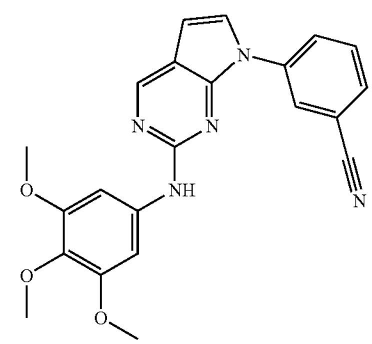 | ¹H NMR 400 MHz (CDCl₃) δ 8.67 (s, 1H), 8.04 (m, 1H), 8.01 (m, 1H), 7.55 (m, 2H), 7.16 (d, 1H), 7.07 (s, 1H), 6.87 (s, 2H), 6.57 (d, 1H), 3.76 (s, 3H), 3.71 (d, 6H); MS (m/z) 503.2 (M + 1). |
| 127 | 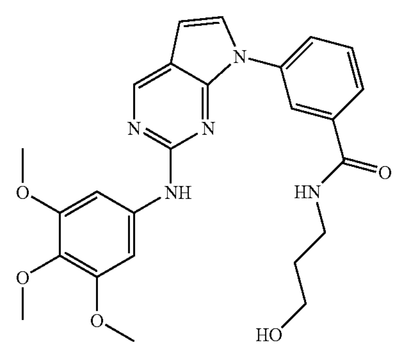 | MS (m/z) 478.2 (M + 1). |

| Compound Number | Structure | Physical Data <sup>1</sup>H NMR and MS (m/z) |
|---|---|---|
| 128 | 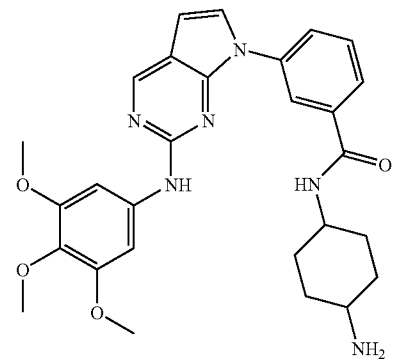 | MS (m/z) 517.3 (M + 1). |
| 129 | 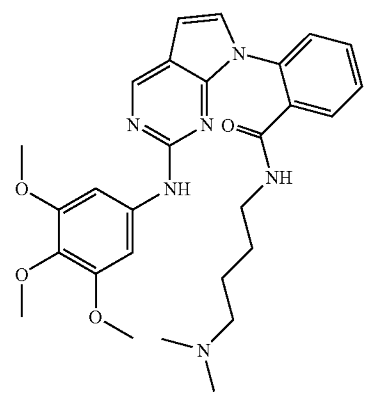 | MS (m/z) 519.2 (M + 1). |
| 130 | 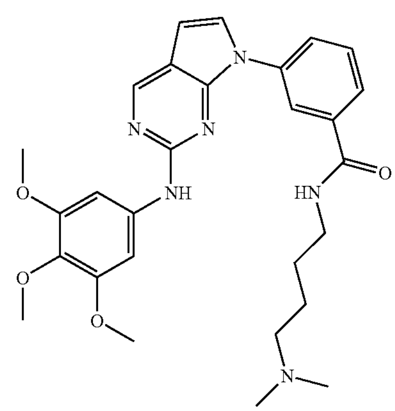 | MS (m/z) 519.3 (M + 1). |
| 131 | 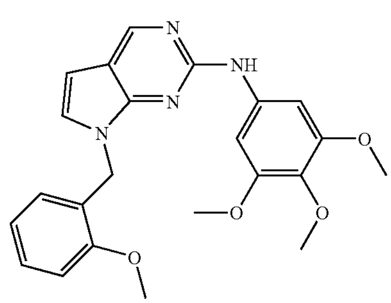 | MS (m/z) 421.2 (M + 1). |

TABLE 1-continued

| Compound Number | Structure | Physical Data ¹H NMR and MS (m/z) |
|---|---|---|
| 132 | 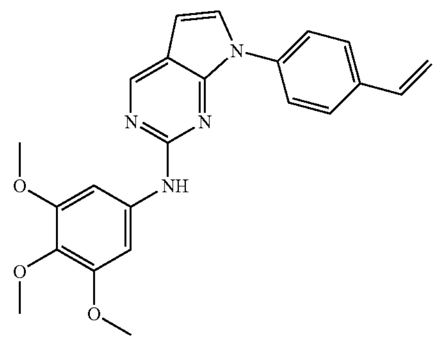 | MS (m/z) 403.2 (M + 1). |
| 133 | 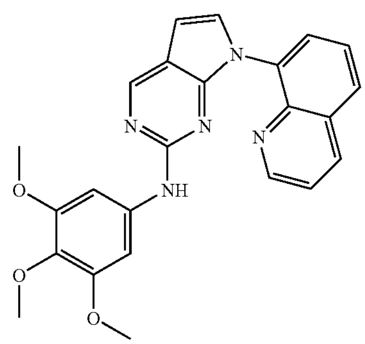 | MS (m/z) 427.9 (M + 1). |
| 134 | 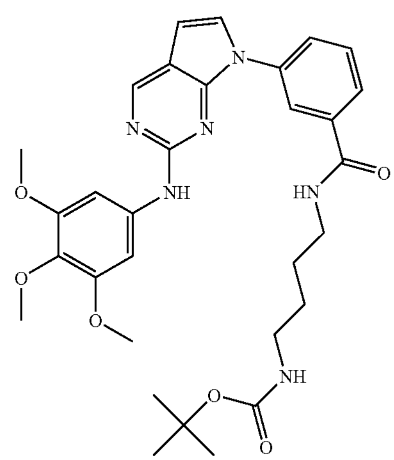 | MS (m/z) 591.3 (M + 1). |
| 135 | 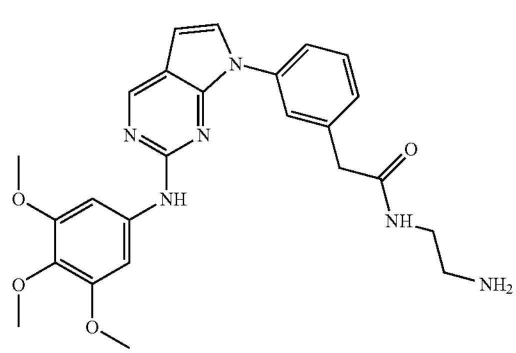 | MS (m/z) 477.2 (M + 1). |

TABLE 1-continued

| Compound Number | Structure | Physical Data $^1$H NMR and MS (m/z) |
|---|---|---|
| 136 | 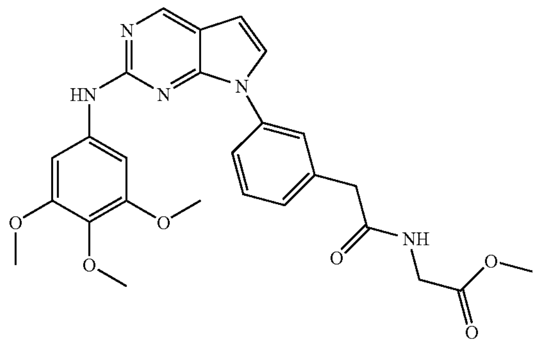 | MS (m/z) 506.2 (M + 1). |
| 137 | 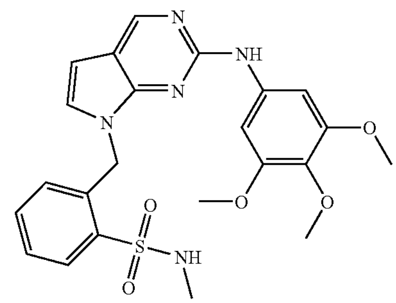 | MS (m/z) 484.2 (M + 1). |
| 138 | 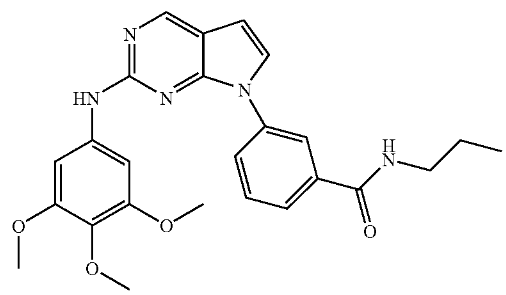 | MS (m/z) 462.2 (M + 1). |
| 139 | 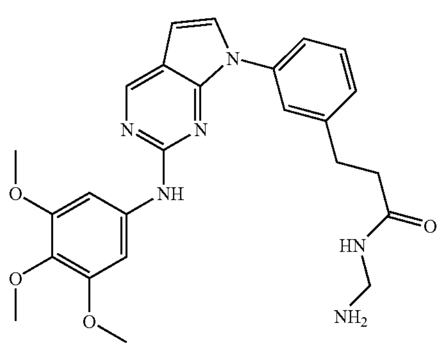 | MS (m/z) 491.2 (M + 1). |

TABLE 1-continued

| Compound Number | Structure | Physical Data ¹H NMR and MS (m/z) |
|---|---|---|
| 140 | 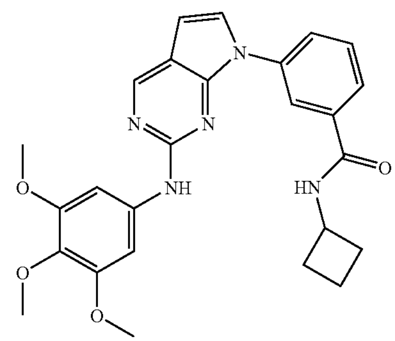 | MS (m/z) 474.2 (M + 1). |
| 141 | 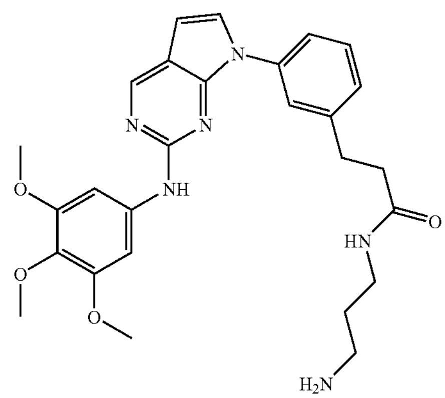 | MS (m/z) 505.3 (M + 1). |
| 142 | 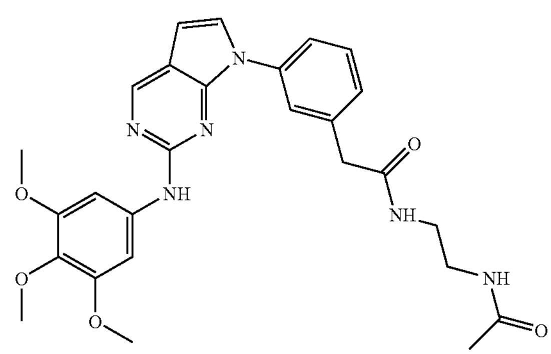 | MS (m/z) 519.2 (M + 1). |
| 143 | 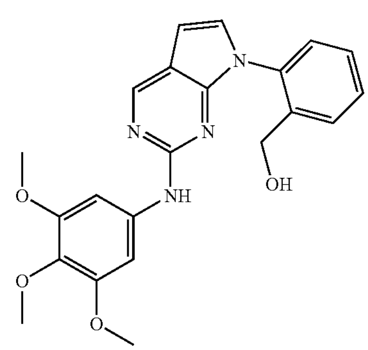 | MS (m/z) 407.3 (M + 1). |

TABLE 1-continued

| Compound Number | Structure | Physical Data<br>$^1$H NMR and MS (m/z) |
| --- | --- | --- |
| 144 | 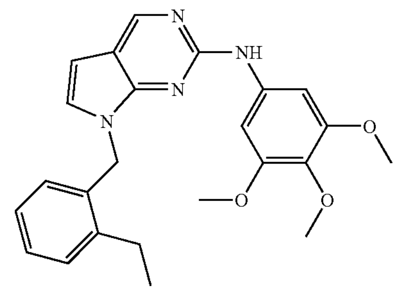 | MS (m/z) 419.2 (M + 1). |
| 145 | 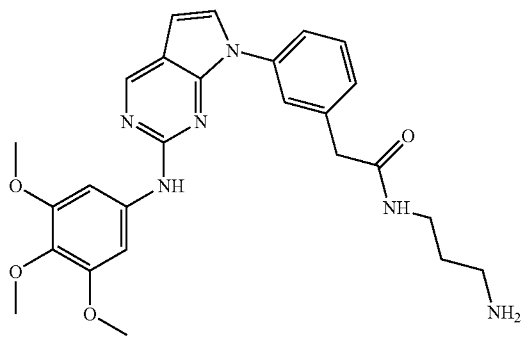 | MS (m/z) 491.2 (M + 1). |
| 146 | 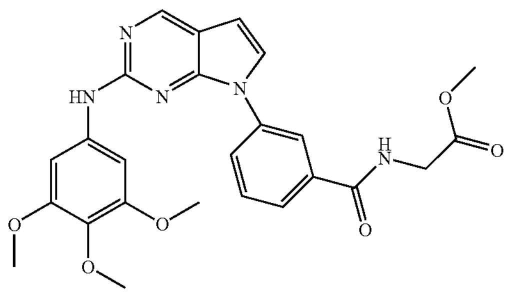 | MS (m/z) 492.2 (M + 1). |
| 147 | 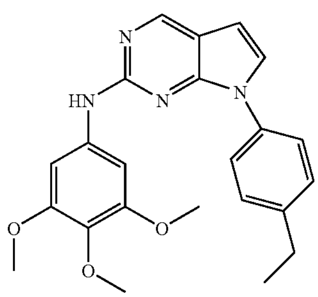 | MS (m/z) 405.2 (M + 1). |
| 148 | 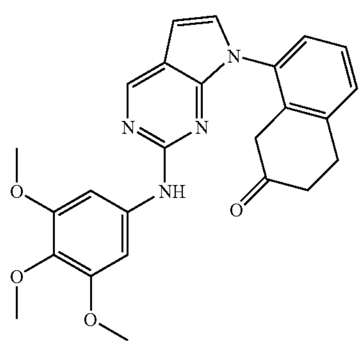 | MS (m/z) 444.9 (M + 1). |

TABLE 1-continued

| Compound Number | Structure | Physical Data ¹H NMR and MS (m/z) |
|---|---|---|
| 149 | 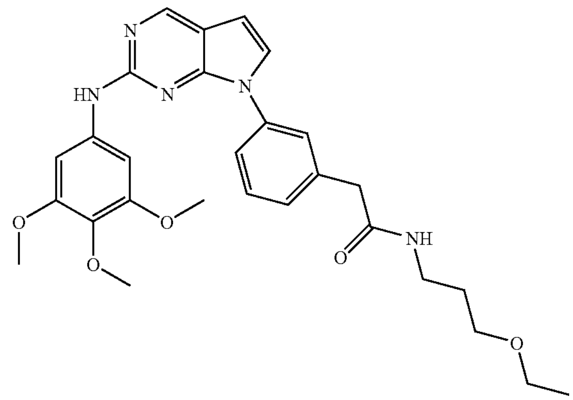 | MS (m/z) 520.3 (M + 1). |
| 150 | 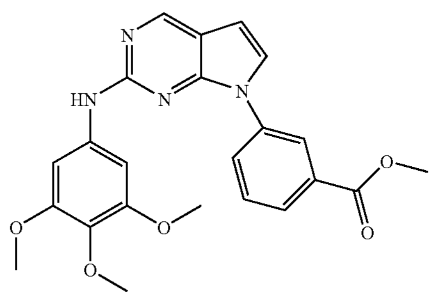 | ¹H NMR 400 MHz (CDCl$_3$) δ 8.71 (s, 1H), 8.29 (t, 1H), 8.08 (m, 1H), 8.01 (m, 1H), 7.57 (t, 1H), 7.26 (d, 1H), 7.18 (s, 1H), 6.93 (s, 2H), 6.60 (d, 1H), 3.93 (s, 3H), 3.80 (d, 9H); MS (m/z) 435.3 (M + 1). |
| 151 | 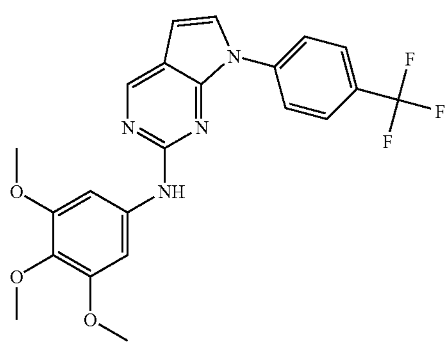 | MS (m/z) 445.1 (M + 1). |
| 152 | 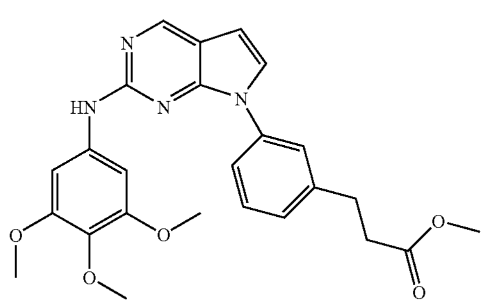 | ¹H NMR 400 MHz (CDCl$_3$) δ 8.64 (s, 1H), 7.56 (m, 1H), 7.41 (m, 1H), 7.33 (t, 1H), 7.12 (m, 2H), 6.90 (s, 2H), 6.50 (d, 1H), 3.73 (s, 3H), 3.65 (s, 6H), 3.60 (s, 3H), 2.97 (m, 2H), 2.60 (m, 2H); MS (m/z) 463.1 (M + 1). |

TABLE 1-continued

| Compound Number | Structure | Physical Data $^1$H NMR and MS (m/z) |
|---|---|---|
| 153 | 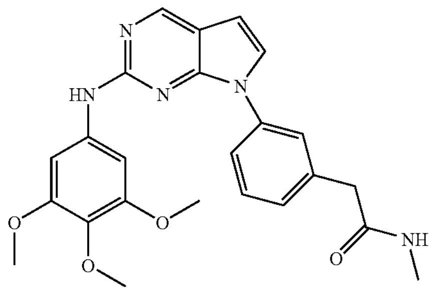 | MS (m/z) 478.2 (M + 1). |
| 154 | 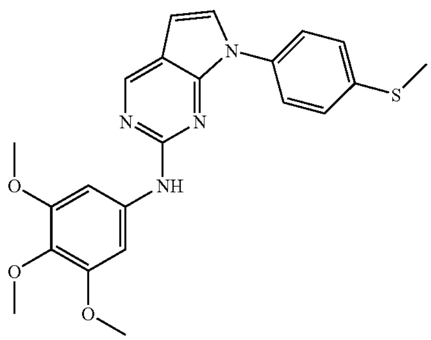 | MS (m/z) 423.1 (M + 1). |
| 155 | 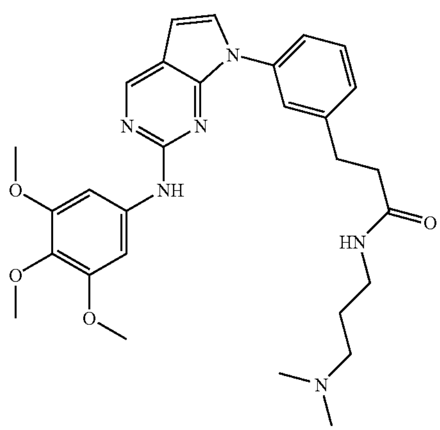 | MS (m/z) 533.3 (M + 1). |
| 156 | 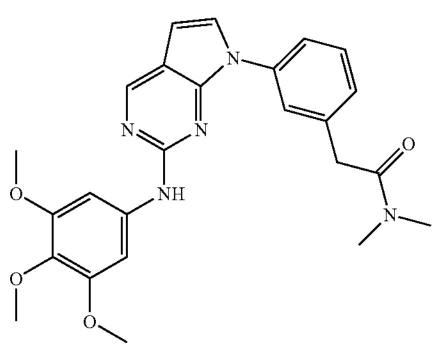 | MS (m/z) 462.2 (M + 1). |

TABLE 1-continued
| Compound Number | Structure | Physical Data $^1$H NMR and MS (m/z) |
|---|---|---|
| 157 | 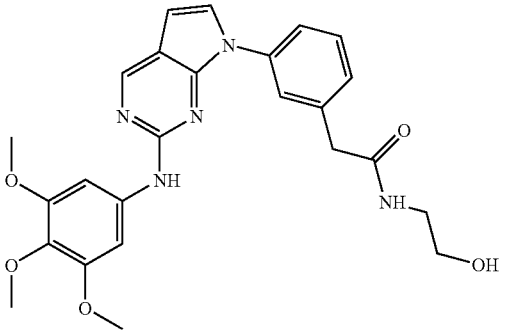 | MS (m/z) 478.2 (M + 1). |
| 158 | 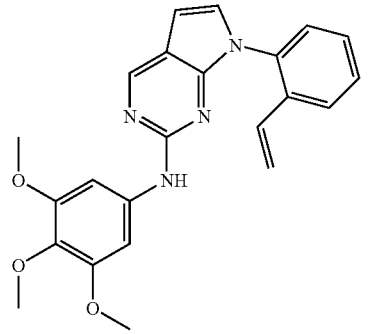 | MS (m/z) 403.2 (M + 1). |
| 159 | 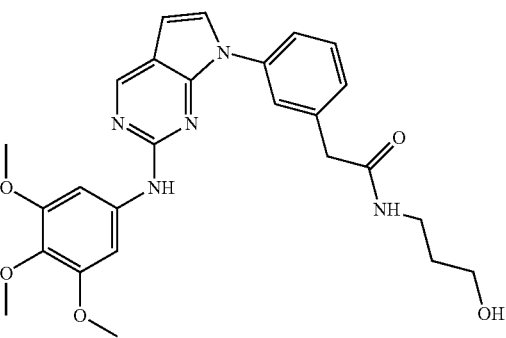 | MS (m/z) 492.2 (M + 1). |
| 160 | 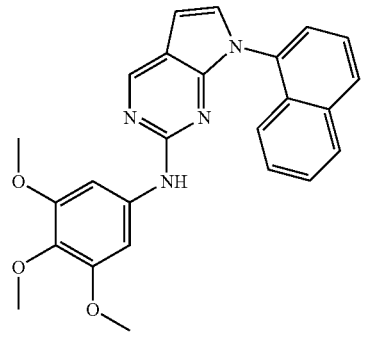 | MS (m/z) 427.2 (M + 1). |

TABLE 1-continued

| Compound Number | Structure | Physical Data ¹H NMR and MS (m/z) |
|---|---|---|
| 161 | 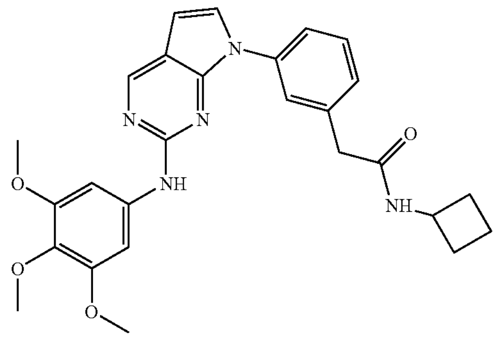 | MS (m/z) 488.2 (M + 1). |
| 162 | 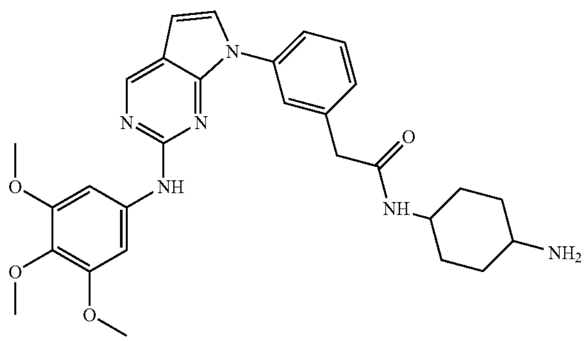 | MS (m/z) 531.3 (M + 1). |
| 163 | 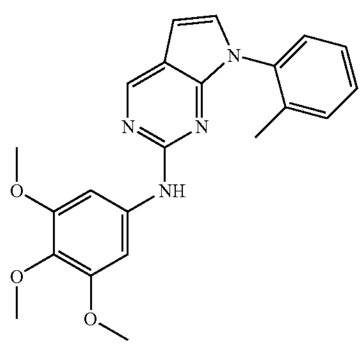 | MS (m/z) 391.2 (M + 1). |
| 164 | 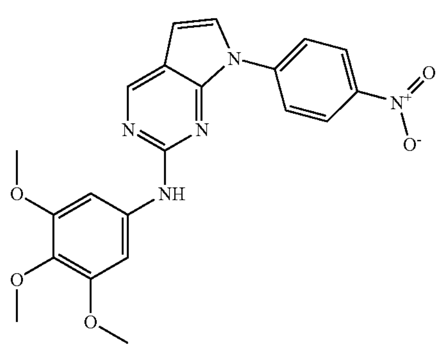 | MS (m/z) 422.1 (M + 1). |

TABLE 1-continued

| Compound Number | Structure | Physical Data $^1$H NMR and MS (m/z) |
|---|---|---|
| 165 | 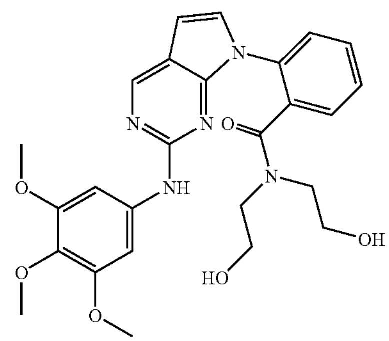 | MS (m/z) 508.2 (M + 1). |
| 166 | 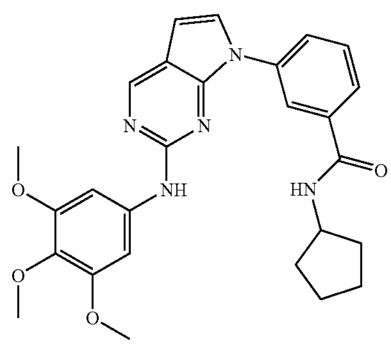 | MS (m/z) 488.2 (M + 1). |
| 167 | 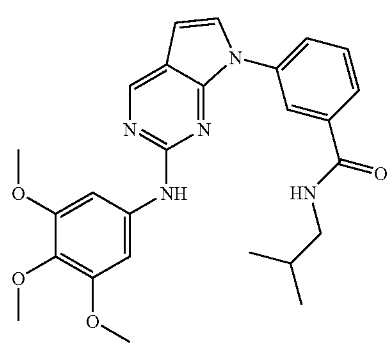 | MS (m/z) 476.2 (M + 1). |
| 168 | 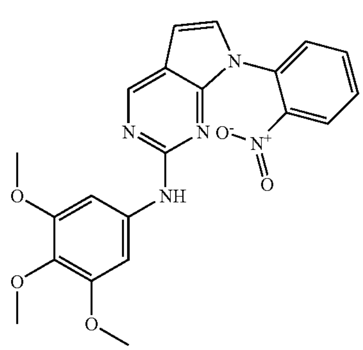 | MS (m/z) 422.1 (M + 1). |

TABLE 1-continued

| Compound Number | Structure | Physical Data <br> ¹H NMR and MS (m/z) |
| --- | --- | --- |
| 169 | 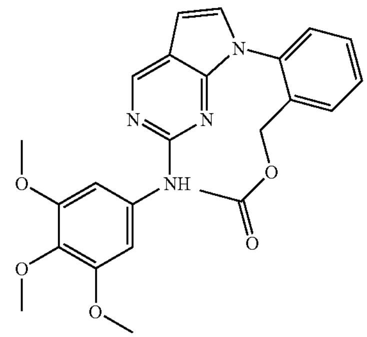 | MS (m/z) 450.3 (M + 1). |
| 170 | 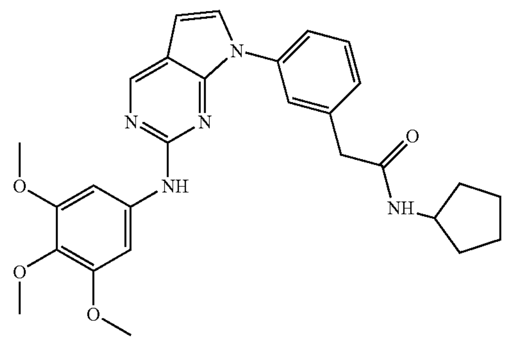 | MS (m/z) 502.2 (M + 1). |
| 171 | 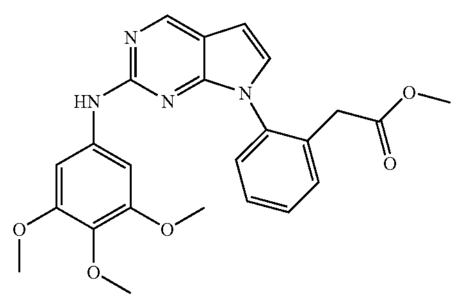 | MS (m/z) 448.9 (M + 1). |
| 172 | 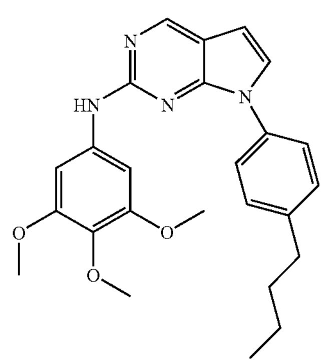 | MS (m/z) 433.2 (M + 1). |

TABLE 1-continued

| Compound Number | Structure | Physical Data $^1$H NMR and MS (m/z) |
|---|---|---|
| 173 | 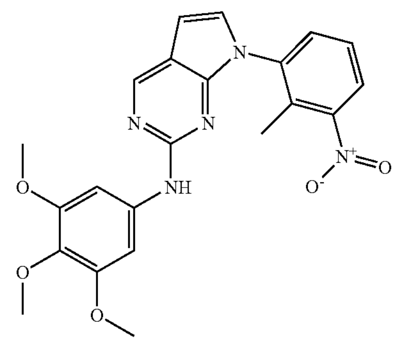 | MS (m/z) 436.1 (M + 1). |
| 174 | 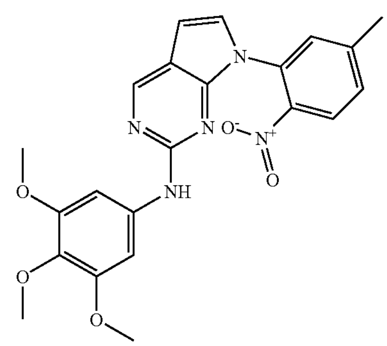 | MS (m/z) 436.1 (M + 1). |
| 175 | 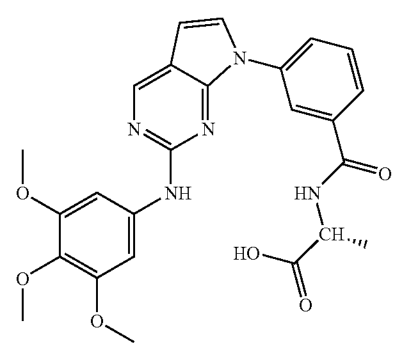 | MS (m/z) 492.2 (M + 1). |
| 176 | 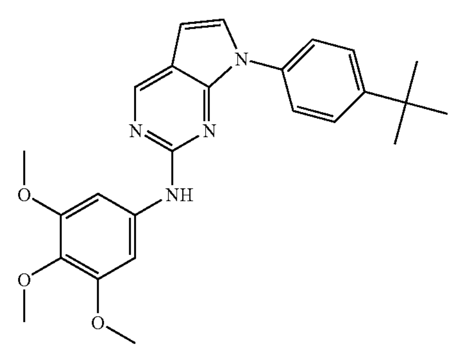 | MS (m/z) 33.2 (M + 1). |

TABLE 1-continued

| Compound Number | Structure | Physical Data <br> ¹H NMR and MS (m/z) |
| --- | --- | --- |
| 177 | 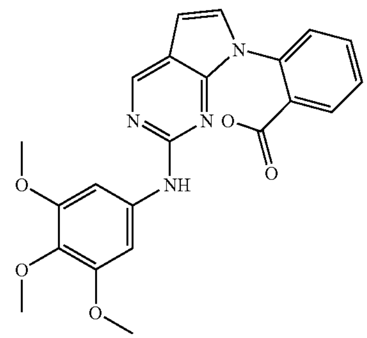 | MS (m/z) 421.2 (M + 1). |
| 178 | 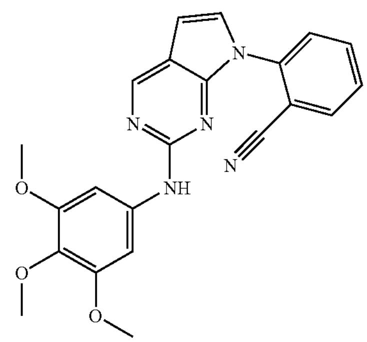 | MS (m/z) 402.2 (M + 1). |
| 179 | 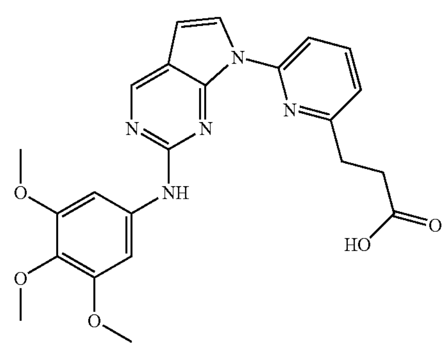 | MS (m/z) 452.2 (M + 1). |
| 180 | 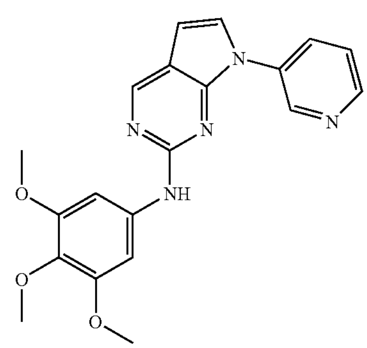 | MS (m/z) 378.2 (M + 1). |

TABLE 1-continued

| Compound Number | Structure | Physical Data <br> ¹H NMR and MS (m/z) |
|---|---|---|
| 181 | 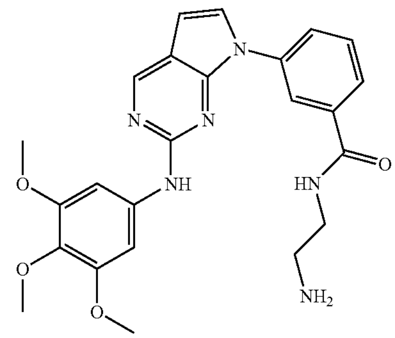 | MS (m/z) 464.1 (M + 1). |
| 182 | 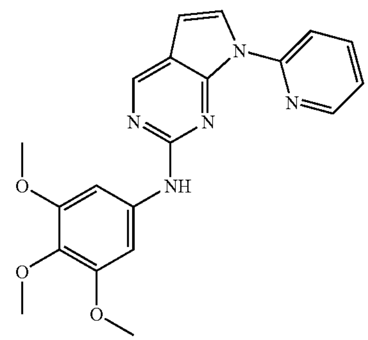 | MS (m/z) 378.2 (M + 1). |
| 183 | 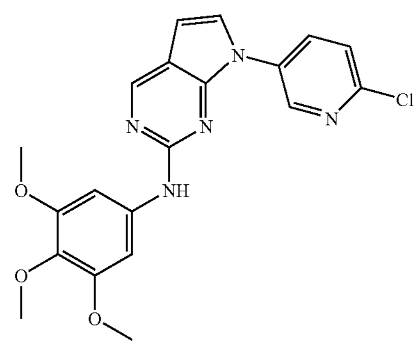 | MS (m/z) 411.11 (M + 1). |
| 184 | 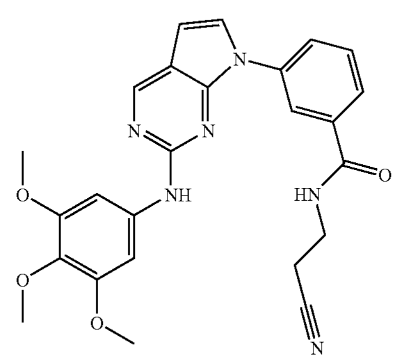 | MS (m/z) 474.1 (M + 1). |

| Compound Number | Structure | Physical Data ¹H NMR and MS (m/z) |
|---|---|---|
| 185 | 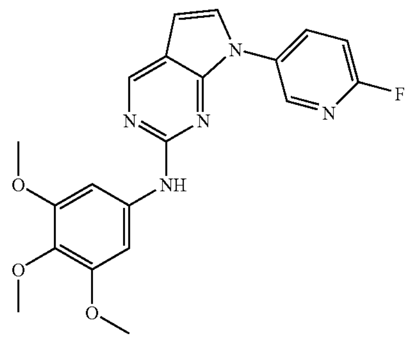 | MS (m/z) 396.1 (M + 1). |
| 186 | 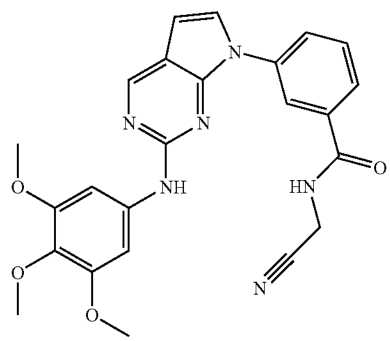 | MS (m/z) 460.1 (M + 1). |
| 187 | 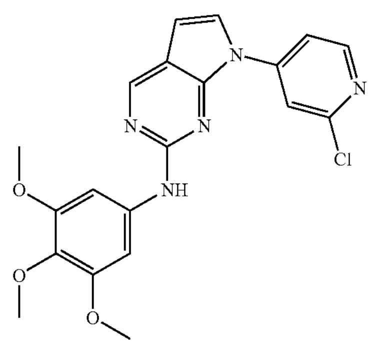 | MS (m/z) 412.1 (M + 1). |
| 188 | 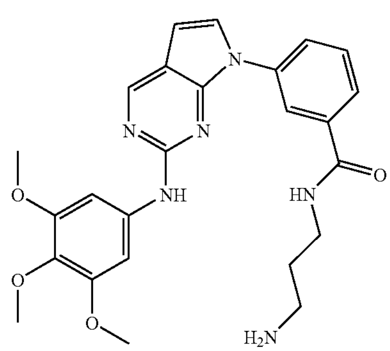 | MS (m/z) 478.2 (M + 1). |

TABLE 1-continued

| Compound Number | Structure | Physical Data $^1$H NMR and MS (m/z) |
|---|---|---|
| 189 | 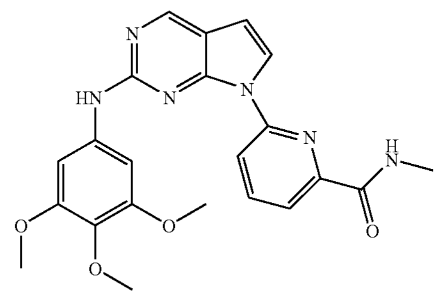 | MS (m/z) 435.1 (M + 1). |
| 190 | 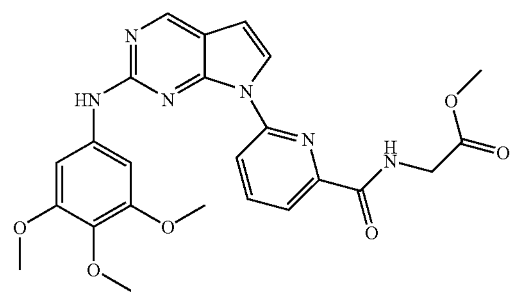 | MS (m/z) 493.10 (M + 1). |
| 191 | 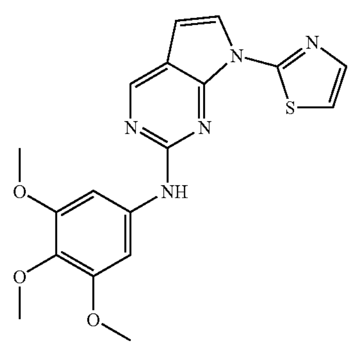 | MS (m/z) 384.1 (M + 1). |
| 192 | 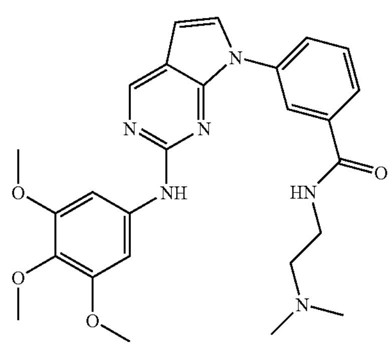 | MS (m/z) 492.2 (M + 1). |
| 193 | 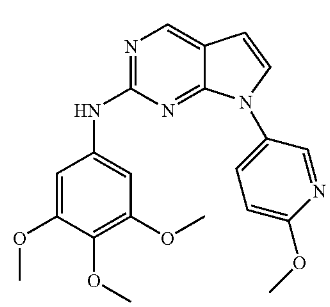 | MS (m/z) 408.2 (M + 1). |

TABLE 1-continued

| Compound Number | Structure | Physical Data<br>¹H NMR and MS (m/z) |
|---|---|---|
| 194 | 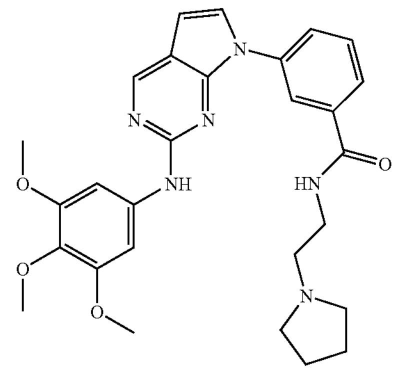 | MS (m/z) 518.20 (M + 1). |
| 195 | 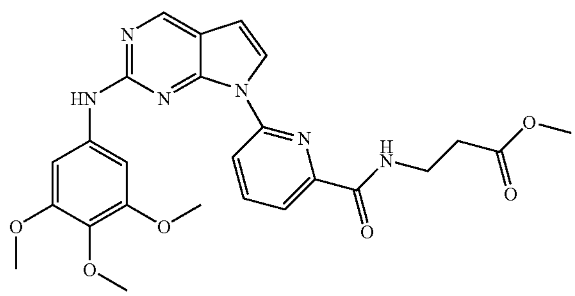 | MS (m/z) 507.15 (M + 1). |
| 196 | 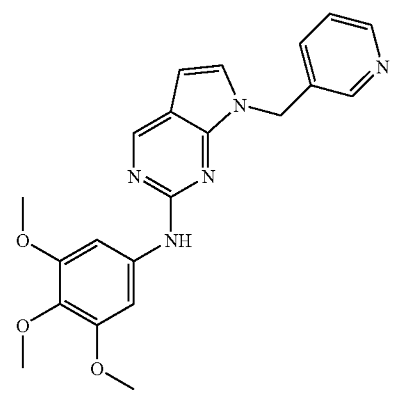 | MS (m/z) 392.20 (M + 1). |
| 197 | 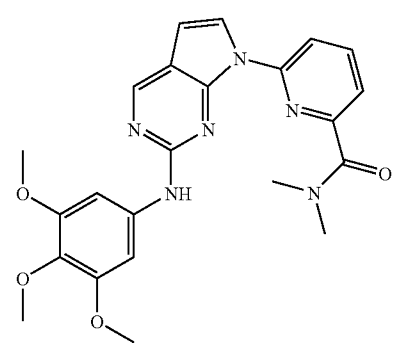 | MS (m/z) 449.10 (M + 1). |

TABLE 1-continued

| Compound Number | Structure | Physical Data ¹H NMR and MS (m/z) |
|---|---|---|
| 198 | 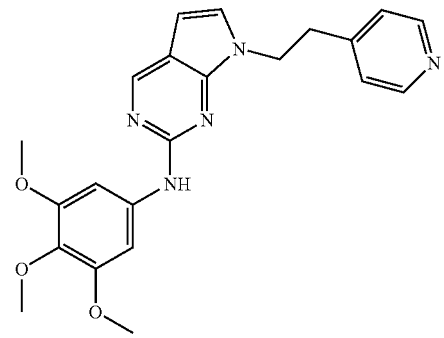 | MS (m/z) 406.2 (M + 1). |
| 199 | 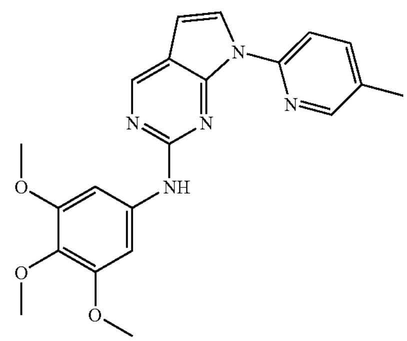 | MS (m/z) 392.2 (M + 1). |
| 200 | 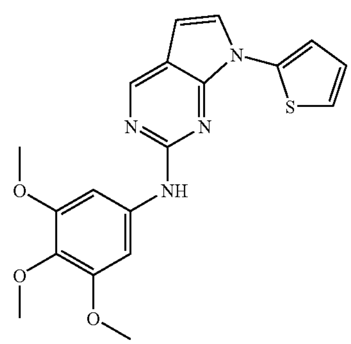 | MS (m/z) 383.1 (M + 1). |
| 201 | 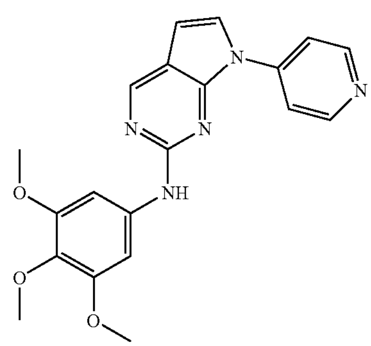 | MS (m/z) 378.2 (M + 1). |

TABLE 1-continued

| Compound Number | Structure | Physical Data<br>¹H NMR and MS (m/z) |
|---|---|---|
| 202 | 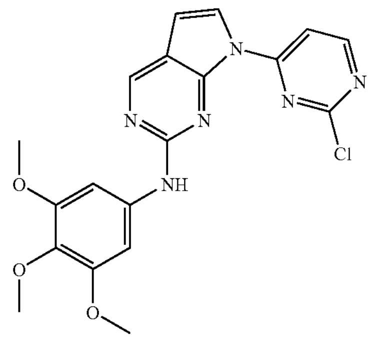 | ¹H NMR 400 MHz (CDCl₃) δ 8.72 (d, 1H), 8.48 (s, 1H), 8.16 (d, 1H), 7.30 (d, 1H), 7.16 (s, 2H), 6.72 (d, 1H), 3.89 (s, 6H), 3.85 (s, 3H); MS (m/z) 413.1 (M + 1). |
| 203 | 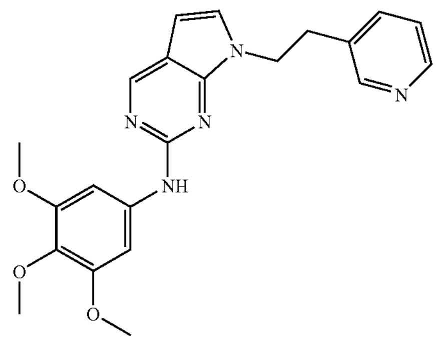 | MS (m/z) 406.3 (M + 1). |
| 204 | 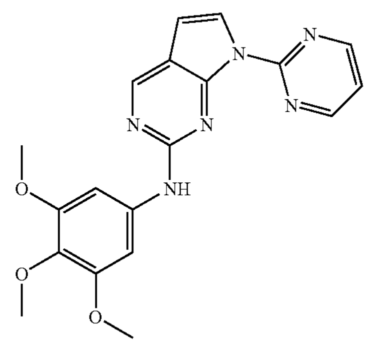 | ¹H NMR 400 MHz (CDCl₃) δ 8.85 (d, 2H), 8.74 (s, 1H), 8.03 (d, 1H), 7.32 (s, 1H), 7.25 (t, 1H), 7.13 (s, 2H), 6.63 (d, 1H), 3.93 (s, 6H), 3.86 (s, 3H); MS (m/z) 379.4 (M + 1). |
| 205 | 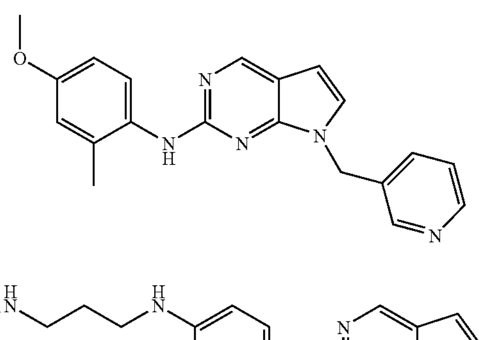 | MS (m/z) 346.2 (M + 1). |
| 206 | 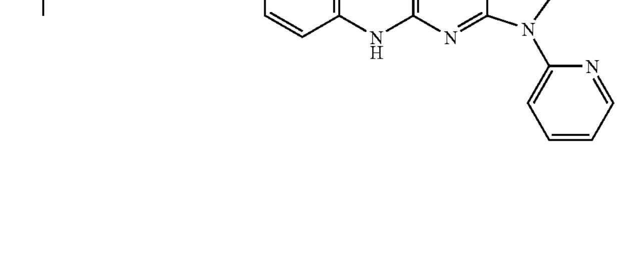 | |

TABLE 1-continued

| Compound Number | Structure | Physical Data ¹H NMR and MS (m/z) |
|---|---|---|
| 208 | 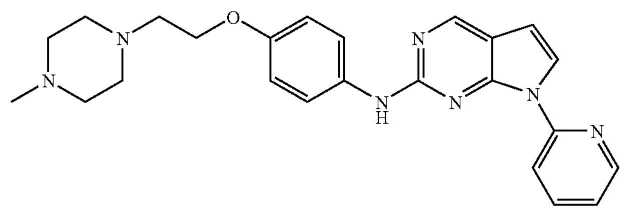 | |
| 209 | 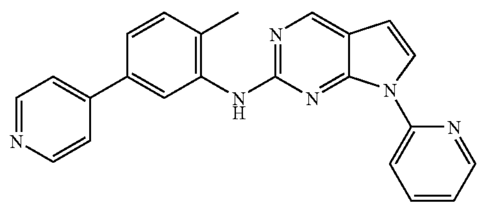 | |
| 210 | 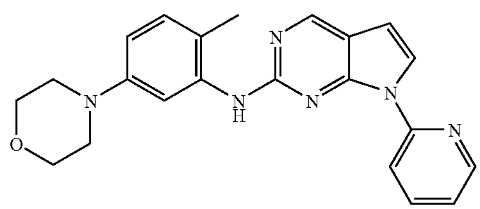 | |
| 211 | 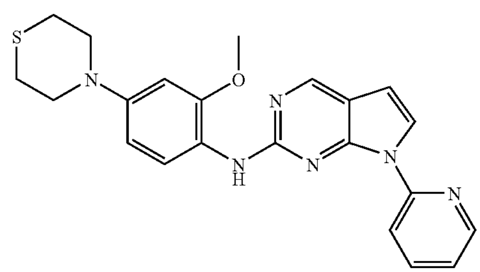 | |
| 212 | 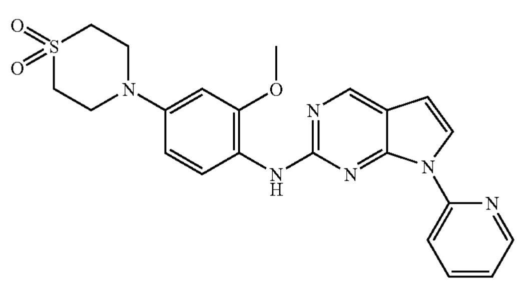 | |
| 213 | 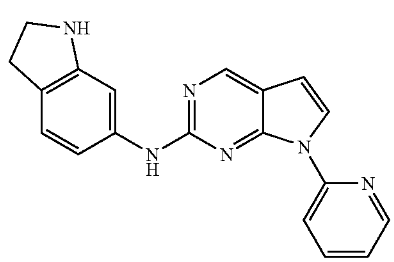 | |

TABLE 1-continued

| Compound Number | Structure | Physical Data ¹H NMR and MS (m/z) |
|---|---|---|
| 214 | 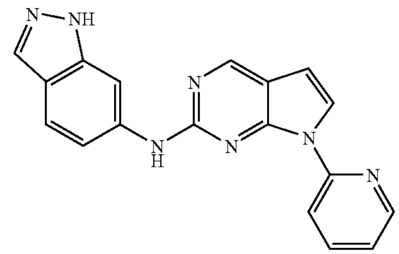 | |
| 215 | 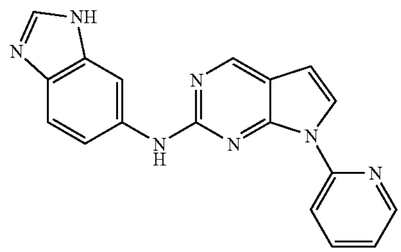 | |
| 216 | 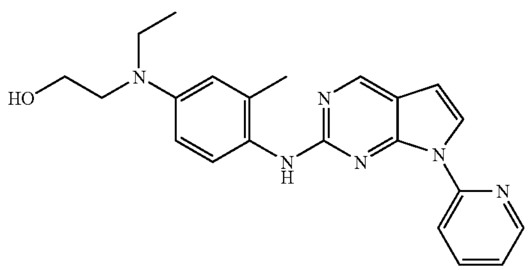 | |
| 217 | 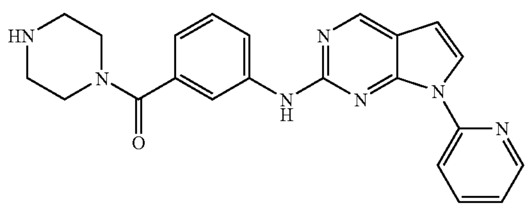 | |

Assays

Compounds of the present invention are assayed to measure their capacity to selectively inhibit cell proliferation of 32D cells expressing BCR-Abl (32D-p210) compared with parental 32D cells. Compounds selectively inhibiting the proliferation of these BCR-Abl transformed cells are tested for anti-proliferative activity on Ba/F3 cells expressing either wild type or the mutant forms of Bcr-abl. In addition, compounds are assayed to measure their capacity to inhibit FAK, Flt-3, ALK and b-Raf.

Inhibition of Cellular BCR-Abl Dependent Proliferation (High Throughput Method)

The murine cell line used is the 32D hemopoietic progenitor cell line transformed with BCR-Abl cDNA (32D-p210). These cells are maintained in RPMI/10% fetal calf serum (RPMI/FCS) supplemented with penicillin 50 µg/mL, streptomycin 50 µg/mL and L-glutamine 200 mM. Untransformed 32D cells are similarly maintained with the addition of 15% WEHI conditioned medium as a source of IL3.

50 µl of a 32D or 32D-p210 cells suspension are plated in Greiner 384 well microplates (black) at a density of 5000 cells per well. 50 nl of test compound (1 mM in DMSO stock solution) is added to each well (ST1571 is included as a positive control). The cells are incubated for 72 hours at 37° C., 5% $CO_2$. 10 µl of a 60% Alamar Blue solution (Tek diagnostics) is added to each well and the cells are incubated for an additional 24 hours. The fluorescence intensity (Excitation at 530 nm, Emission at 580 nm) is quantified using the Acquest™ system (Molecular Devices).

Inhibition of Cellular BCR-Abl Dependent Proliferation 32D-p210 cells are plated into 96 well TC plates at a density of 15,000 cells per well. 50 µL of two fold serial dilutions of the test compound ($C_{max}$ is 40 µM) are added to each well (ST1571 is included as a positive control). After incubating the cells for 48 hours at 37° C., 5% $CO_2$, 15 µL of MTT (Promega) is added to each well and the cells are incubated for an additional 5 hours. The optical density at 570 nm is quantified spectrophotometrically and $IC_{50}$ values, the concentration of compound required for 50% inhibition, determined from a dose response curve.

Effect on Cell Cycle Distribution 32D and 32D-p210 cells are plated into 6 well TC plates at $2.5 \times 10^6$ cells per well in 5 ml of medium and test compound at 1 or 10 µM is added (ST1571 is included as a control). The cells are then incubated for 24 or 48 hours at 37° C., 5% $CO_2$. 2 ml of cell suspension is washed with PBS, fixed in 70% EtOH for 1 hour and treated with PBS/EDTA/RNase A for 30 minutes. Propidium iodide (Cf=10 µg/ml) is added and the fluorescence intensity is quantified by flow cytometry on the FACScalibur™ system (BD Biosciences). Test compounds of the present invention demonstrate an apoptotic effect on the 32D-p210 cells but do not induce apoptosis in the 32D parental cells.

Effect on Cellular BCR-Abl Autophosphorylation

BCR-Abl autophosphorylation is quantified with capture Elisa using a c-abl specific capture antibody and an antiphosphotyrosine antibody. 32D-p210 cells are plated in 96 well TC plates at $2\times10^5$ cells per well in 50 µL of medium. 50 µL of two fold serial dilutions of test compounds ($C_{max}$ is 10 µM) are added to each well (ST1571 is included as a positive control). The cells are incubated for 90 minutes at 37° C., 5% $CO_2$. The cells are then treated for 1 hour on ice with 150 µL of lysis buffer (50 mM Tris-HCl, pH 7.4, 150 mM NaCl, 5 mM EDTA, 1 mM EGTA and 1% NP-40) containing protease and phosphatase inhibitors. 50 µL of cell lysate is added to 96 well optiplates previously coated with anti-abl specific antibody and blocked. The plates are incubated for 4 hours at 4° C. After washing with TBS-Tween 20 buffer, 50 µL of alkaline-phosphatase conjugated anti-phosphotyrosine antibody is added and the plate is further incubated overnight at 4° C. After washing with TBS-Tween 20 buffer, 90 µL of a luminescent substrate are added and the luminescence is quantified using the Acquest™ system (Molecular Devices). Test compounds of the invention that inhibit the proliferation of the BCR-Abl expressing cells, inhibit the cellular BCR-Abl autophosphorylation in a dose-dependent manner.

Effect on Cellular BCR-Abl Autophosphorylation

Effect on Proliferation of Cells Expressing Mutant Forms of Bcr-abl

Compounds of the invention are tested for their antiproliferative effect on Ba/F3 cells expressing either wild type or the mutant forms of BCR-Abl (G250E, E255V, T315I, F317L, M351T) that confers resistance or diminished sensitivity to STI571. The antiproliferative effect of these compounds on the mutant-BCR-Abl expressing cells and on the non transformed cells were tested at 10, 3.3, 1.1 and 0.37 µM as described above (in media lacking IL3). The $IC_{50}$ values of the compounds lacking toxicity on the untransformed cells were determined from the dose response curves obtained as describe above.

Flt-3 Inhibition

The general technique involves comparing the effects of possible inhibitors on cell lines that depend on mutant Flt3 for proliferation vs. cell lines that do not depend on mutant Flt3 for proliferation. Compounds that have differential activity (more than or equal to 10 fold difference in sensitivity between Flt3+cell lines and Flt3− cell lines are selected for further study.

The cell lines used for the initial screening are sub-lines of Ba/F3 cells that are engineered to over-express mutant or wild-type (non-mutated) Flt3 following infection with a retrovirus expressing appropriate Flt3 cDNAs. The parent cell line, Ba/F3 is dependent on interleukin-3 for proliferation, and when deprived of IL-3, the cells rapidly cease proliferation and die. The retrovirus expresses Flt3 from the retroviral LTR and the neo gene from an IRES site. Ba/F3 cells are selected in G418 and analyzed for expression of Flt3 by fluorescence activated cell sorting (FACS). Cell lines with two different Flt3 mutations are used. One mutant expresses a Flt-3 that has a 14 amino acid duplication in the juxtamembrane domain encoded by exon 11, the specific duplication being . . . VDFREYEYDLKWEF . . . (termed, Ba/F3-Flt3-ITD). The second mutation has a point mutation that converts asparagines at position 835 to tyrosine (termed Ba/F3-Flt3-D835Y). Both mutations lead to Flt-3 kinase activation and make it independent of IL-3 and the expressing cells grow in the absence of IL-3. Ba/F3 cells expressing wild type Flt3 are similarly generated and used as the "control" cell line. The parental (uninfected) cell line, and the wild-type "control" cell line remain dependent on IL-3 for proliferation.

Ba/F3 cells (-control, -Flt3-ITD, or -Flt3-D835Y) are cultured up to 500,000 cells/mL in 30 mL cultures, with RPMI 1640 with 10% fetal calf serum as the culture medium. The medium for the control cells, (but not the mutant-Flt3 cells) contains 10% conditioned medium from the WEHI-3B cell line as a source of IL-3. A 10 mM "stock" solution of each compound is made in dimethylsufoxide (DMSO). Dilutions are then made into RPMI 1640 with 10% fetal calf serum to create final drug concentrations ranging typically from 1 nM to 10 µM. Similar dilutions are made of DMSO to serve as vehicle controls. 48 hours after addition of compounds, cells are assayed for proliferation rate and cytotoxicity.

Yo-Pro-1 iodide (Molecular Probes) is added to the cells at a final concentration of 2.5 µM in NaCl/Na-citrate buffer. The cells are incubated with Yo-Pro for 10 minutes at room temperature and then read on a fluorimeter for determination of cytotoxicity. Next, the cells are lysed with NP40/EDTA/EGTA buffer, incubated at room temperature for 90 minutes and read for the determination of proliferation.

Compounds that are selectively more toxic to Ba/F3-Flt3-ITD cells than to wild type control Ba/F3 cells are further tested on the Flt3-D835Y expressing cells.

Additionally, α-Flt3 antibodies are used to immunoprecipitate Flt3 proteins before, and after, exposure to various concentrations of active compounds. The immuno-precipitated proteins are separated by sodium dodecyl sulfate polyacrylamide gels, transferred electrophoretically to PVDF membrane, and immunoblotted with an α-phospho-$^{591}$Y-Flt3 antibody. This assay determines if compounds reduce the "autophosphorylation" levels of Flt3 characteristic of the mutated forms of the receptor.

Compounds of the invention typically show antiproliferative activity against Flt3-ITD in the nanomolar range while being non-toxic against control-Flt3 up to 10 µM. Compounds of the invention also reduce the autophosphorylation activity of cellular Flt-3 in the nanomolar range.

Focal Adhesion Kinase (FAK) Inhibition

Compounds of the invention are tested for their ability to inhibit the activity of FAK. The FAK kinase activities are measured in 384-well plates using a time-resolved fluorescence resonance energy transfer (TR-FRET)-based assay method. Full length human FAK is expressed in *E. Coli* as a GST-tagged protein and purified by an immobilized glutathione column. A biotinylated peptide, biotin-SETD-DYAEIID (Synthesized by SynPep Corp.), corresponding to the autophosphorylation site sequence of human FAK, is used as the substrate in the assay. *E. Coli*-expressed FAK kinase (2.4 µg/ml) is mixed together with FAK peptide (133 nM) in 15 µl of assay buffer (20 mM Hepes, pH7.4, 5mM $MgCl_2$, 2 mM $MnCl_2$, 0.5 mM $Na_3VO_4$, 0.1% BSA, 0.1% TritonX-100). A compound of the invention (0.5 µl—dissolved in DMSO) is then added to the enzyme/peptide solution. After incubation at room temperature for 10 minutes, 5 µl of 40 µM ATP in assay buffer is added to initiate the reaction. The reaction mixture is incubated at room temperature for 2 hours. 50 µl of detection reagents containing 0.1 5 nM of Eu-labeled antiphosphotyrosine antibodies (PT66-Eu, PerkinElmer) and 1.5 µg/ml of SA-APC (PerkinElmer) in detection buffer (10 mM Tris-HCl, pH7.4, 6 mM EDTA, 0.1% BSA, 0.1% TritonX-100) is then added. The mixture is incubated at room temperature for 30 minutes and the TR-FRET signals are measured using an Acquest plate reader (Molecular Device).

ALK Inhibition

The inhibition of ALK tyrosine kinase activity can be demonstrated using known methods, for example using the recombinant kinase domain of the ALK in analogy to the VEGF-R kinase assay described in J. Wood et al. Cancer Res. 60, 2178-2189 (2000). In vitro enzyme assays using GST-ALK protein tyrosine kinase are performed in 96-well plates as a filter binding assay in 20 mM Tris-HCl, pH=7.5, 3 mM MgCl$_2$, 10 mM MnCl$_2$, 1 mM DTT, 0.1 µCi/assay (=30 µl) [$\gamma$-$^{33}$P]-ATP, 2 µM ATP, 3 µg/ml poly (Glu, Tyr 4:1) Poly-EY (Sigma P-0275), 1% DMSO, 25 ng ALK enzyme. Assays are incubated for 10 min at ambient temperature. Reactions are terminated by adding 50 µl of 125 mM EDTA, and the reaction mixture is transferred onto a MAIP Multiscreen plate (Millipore, Bedford, Mass., USA), previously wet with methanol, and rehydrated for 5 minutes with H$_2$O. Following washing (0.5% H$_3$PO$_4$), plates are counted in a liquid scintillation counter. IC$_{50}$ values are calculated by linear regression analysis of the percentage inhibition. Compared with the control without inhibitor, the compounds of formula I inhibit the enzyme activity by 50% (IC$_{50}$), for example in a concentration of from 0.001 to 0.5 µM, especially from 0.01 to 0.1 µM.

The compounds of formula I potently inhibit the growth of human NPM-ALK overexpressing murine BaF3 cells (DSMZ Deutsche Sammlung von Mikroorganismen und Zellkulturen GmbH, Braunschweig, Germany). The expression of NPM-ALK is achieved by transfecting the BaF3 cell line with an expression vector pCIneo™ (Promega Corp., Madison Wis., USA) coding for NPM-ALK and subsequent selection of G418 resistant cells. Non-transfected BaF3 cells depend on IL-3 for cell survival. In contrast NPM-ALK expressing BaF3 cells (named BaF3-NPM-ALK hereinafter) can proliferate in the absence of IL-3 because they obtain proliferative signal through NPM-ALK kinase. Putative inhibitors of the NPM-ALK kinase therefore abolish the growth signal and result in antiproliferative activity. The antiproliferative activity of putative inhibitors of the NPM-ALK kinase can however be overcome by addition of IL-3 which provides growth signals through an NPM-ALK independent mechanism. [For an analogous cell system using FLT3 kinase see E Weisberg et al. Cancer Cell; 1, 433-443 (2002)]. The inhibitory activity of the compounds of formula I is determined, briefly, as follows: BaF3-NPM-ALK cells (15,000/microtitre plate well) are transferred to 96-well microtitre plates. The test compounds [dissolved in dimethyl sulfoxide (DMSO)] are added in a series of concentrations (dilution series) in such a manner that the final concentration of DMSO is not greater than 1% (v/v). After the addition, the plates are incubated for two days during which the control cultures without test compound are able to undergo two cell-division cycles. The growth of the BaF3-NPM-ALK cells is measured by means of Yopro™ staining [T Idziorek et al. J. Immunol. Methods; 185: 249-258 (1995)]: 25 µl of lysis buffer consisting of 20 mM sodium citrate, pH 4.0, 26.8 mM sodium chloride, 0.4% NP40, 20 mM EDTA and 20 mM is added to each well. Cell lysis is completed within 60 min at room temperature and total amount of Yopro bound to DNA is determined by measurement using the Cytofluor II 96-well reader (PerSeptive Biosystems) with the following settings: Excitation (nm) 485/20 and Emission (nm) 530/25.

IC$_{50}$ values are determined by a computer-aided system using the formula:

$$IC_{50}=[(ABS_{test}-ABS_{start})/(ABS_{control}-ABS_{start})]\times 100.$$
(ABS=absorption)

The IC$_{50}$ value in those experiments is given as that concentration of the test compound in question that results in a cell count that is 50% lower than that obtained using the control without inhibitor. The compounds of formula I exhibit inhibitory activity with an IC$_{50}$ in the range from approximately 0.01 to 1 µM.

The antiproliferative action of the compounds of formula I can also be determined in the human KARPAS-299 lymphoma cell line (DSMZ Deutsche Sammlung von Mikroorganismen und Zellkulturen GmbH, Braunschweig, Germany) [described in WG Dirks et al. Int. J. Cancer 100, 49-56 (2002)] using the same methodology described above for the BaF3-NPM-ALK cell line. The compounds of Formula I exhibit inhibitory activity with an IC$_{50}$ in the range from approximately 0.01 to 1 µM.

The action of the compounds of Formula I on autophosphorylation of the ALK can be determined in the human KARPAS-299 lymphoma cell line by means of an immunoblot as described in WG Dirks et al. Int. J. Cancer 100, 49-56 (2002). In that test the compounds of Formula I exhibit an IC$_{50}$ of approximately from 0.001 to 1 µM.

Upstate KinaseProfiler™—Radio-Enzymatic Filter Binding Assay

Compounds of the invention are assessed for their ability to inhibit individual members of a panel of kinases (a partial, non-limiting list of kinases includes: FAK, Abl, BCR-Abl, PDGF-R, c-Kit, NPM-ALK, Flt-3, JAK2 and c-Met. The compounds are tested in duplicates at a final concentration of 10 µM following this generic protocol. Note that the kinase buffer composition and the substrates vary for the different kinases included in the "Upstate KinaseProfiler™" panel. The compounds are tested in duplicates at a final concentration of 10 µM following this generic protocol. Note that the kinase buffer composition and the substrates vary for the different kinases included in the "Upstate KinaseProfiler™" panel. Kinase buffer (2.5 µL, 10×—containing MnCl$_2$ when required), active kinase (0.001-0.01 Units; 2.5 µL), specific or Poly(Glu4-Tyr) peptide (5-500 µM or 0.01 mg/ml) in kinase buffer and kinase buffer (50 µM; 5 µL) are mixed in an eppendorf on ice. A Mg/ATP mix (10 µL; 67.5 (or 33.75) mM MgCl$_2$, 450 (or 225) µM ATP and 1 µCi/µl [$\gamma$—$^{32}$P]-ATP (3000 Ci/mmol)) is added and the reaction is incubated at about 30° C. for about 10 minutes. The reaction mixture is spotted (20 µL) onto a 2 cm×2 cm P81 (phosphocellulose, for positively charged peptide substrates) or Whatman No. 1 (for Poly (Glu4-Tyr) peptide substrate) paper square. The assay squares are washed 4 times, for 5 minutes each, with 0.75% phosphoric acid and washed once with acetone for 5 minutes. The assay squares are transferred to a scintillation vial, 5 ml scintillation cocktail are added and $^{32}$P incorporation (cpm) to the peptide substrate is quantified with a Beckman scintillation counter. Percentage inhibition is calculated for each reaction. Compounds of Formula I, at a concentration of 10 µM, preferably show a percentage inhibition of greater than 50%, preferably greater than 60%, more preferably greater than 70%, against FAK, Abl, BCR-Abl, PDGF-R, c-Kit, NPM-ALK, Flt-3, JAK2 and/or c-Met kinases.

Compounds of Formula I, in free form or in pharmaceutically acceptable salt form, exhibit valuable pharmacological properties, for example, as indicated by the in vitro tests described in this application. For example, compounds of Formula I preferably show an IC$_{50}$ in the range of 1×10$^{-10}$ to $1\times10^{-5}$ M, more preferably less than 500 nM for at least one of the following kinases: FAK, Abl, BCR-Abl, PDGF-R, c-Kit, NPM-ALK, Flt-3, JAK2 and c-Met kinases. For example:

(i) N-(2-Dimethylamino-ethyl)-3-[2-(3,4,5-trimethoxy-phenylamino)-pyrrolo[2,3-d]pyrimidin-7-yl]-benzamide (example 73) has an $IC_{50}$ of 38 nM for FAK.

(ii) {3-[2-(3,4,5-Trimethoxy-phenylamino)-pyrrolo[2,3-d]pyrimidin-7-yl]-phenyl}-acetonitrile (example 104) has an $IC_{50}$ of 29 nM, 282 nM, 342 nM, 33 nM, and 479 nM for FLT3-ITD, FGFR3, JAK2, PDGFR-beta, and Tel-TRKC respectively.

(iii) {7-[3-(1-Methyl-1H-tetrazol-5-ylmethyl)-phenyl]-7H-pyrrolo[2,3-d]pyrimidin-2-yl}-(3,4,5-trimethoxy-phenyl)-amine (example 120) has an $IC_{50}$ of 29 nM for BaF3/PDGFR-beta.

(iv) 3-{3-[2-(3,4,5-Trimethoxy-phenylamino)-pyrrolo[2,3-d]pyrimidin-7-yl]-phenyl}-propionitrile (example 85) has an $IC_{50}$ of 16 nM for FLT3-ITD.

(v) (7-Pyridin-2-yl-6,7-dihydro-5H-pyrrolo[2,3-d]pyrimidin-2-yl)-(3,4,5-trimethoxy-phenyl)-amine (example 61) has an $IC_{50}$ of 284 nM for FGFR3.

(vi) [7-(2-Chloro-pyridin-4-yl)-7H-pyrrolo[2,3-d]pyrimidin-2-yl]-(4-methoxy-2-methyl-phenyl)-amine (example 47) has an $IC_{50}$ of 408 nM for BCR-Abl.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

We claim:

1. A compound selected from Formula Ia and Id:

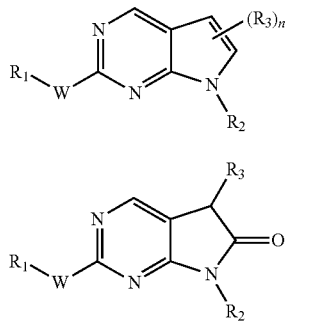

in which:

n is selected from 0, 1 and 2;

W is selected from —$NR_4$—, —S—, —O—, —S(O)— and —$S(O)_2$—; wherein $R_4$ is selected from hydrogen and $C_{1-6}$alkyl;

$R_1$ is selected from $C_{6-10}$aryl-$C_{0-4}$alkyl, $C_{5-10}$heteroaryl-$C_{0-4}$alkyl, $C_{3-12}$cycloalkyl-$C_{0-4}$alkyl and $C_{3-8}$heterocycloalkyl-$C_{0-4}$alkyl; wherein any aryl, heteroaryl, cycloalkyl or heterocycloalkyl of $R_1$ is optionally substituted by 1 to 3 groups independently selected from halo, nitro, cyano, $C_{6-10}$aryl, $C_{5-10}$heteroaryl, $C_{3-12}$cycloalkyl, $C_{3-8}$heterocycloalkyl, $C_{1-6}$alkyl, $C_{1-6}$alkoxy, halo-substituted-$C_{1-6}$alkyl, halo-substituted-$C_{1-6}$alkoxy, —$XNR_5R_5$, —$XNR_5XNR_5R_5$, —$XNR_5XOR_5$, —$XOR_5$, —$XSR_5$, —$XS(O)R_5$, —$XS(O)_2R_5$, —$XC(O)NR_5R_5$, —$XOXR_6$ and —$XC(O)R_6$; wherein X is a bond or $C_{1-6}$alkylene; $R_5$ is selected from hydrogen, $C_{1-6}$alkyl and $C_{3-12}$cycloalkyl-$C_{0-4}$alkyl; and $R_6$ is selected from $C_{3-8}$heterocycloalkyl-$C_{0-4}$alkyl and $C_{5-10}$heteroaryl-$C_{0-4}$alkyl optionally substituted by 1 to 3 groups selected from $C_{1-6}$alkyl and —C(O)OH; wherein any aryl, heteroaryl, cycloalkyl or heterocycloalkyl substituent of $R_1$ is further optionally substituted by 1 to 5 groups independently selected from $C_{1-6}$alkyl and $C_{1-6}$alkoxy;

$R_2$ is selected from $C_{6-10}$aryl-$C_{0-4}$alkyl, $C_{5-10}$heteroaryl-$C_{0-4}$alkyl, $C_{3-12}$cycloalkyl-$C_{0-4}$alkyl; wherein any arylalkyl, heteroarylalkyl, cycloalkylalkyl of $R_2$ is optionally substituted by 1 to 3 groups independently selected from halo, nitro, cyano, $C_{1-6}$alkyl, $C_{2-6}$alkenyl, $C_{2-6}$alkynyl, $C_{1-6}$alkoxy, halo-substituted-$C_{1-6}$alkyl, halo-substituted-$C_{1-6}$alkoxy, $C_{3-8}$heteroaryl $C_{0-4}$alkyl, —$XNR_5R_5$, —$XOR_5$, —$XSR_5$, —$XS(O)R_5$, —$XS(O)_2R_5$, —$XSNR_5R_5$, —$XS(O)NR_5R_5$, —$XS(O)_2NR_5R_5$, —$XC(O)OR_5$, —$XOC(O)R_5$, —$XC(O)R_5$, —$XC(O)NR_5XNR_5R_5$, —$XC(O)NR_5R_5$, —$XC(O)NR_5XC(O)OR_5$, —$XC(O)NR_5XNR_5C(O)R_5$, —$XC(O)NR_5C(O)OR_5$, —$XC(O)NR_5XOR_5$, —$XC(O)N(XOR_5)_2$, —$XNR_5C(O)R_5$, —$XC(O)NR_5R_6$, —$XC(O)R_6$, —$XC(O)R_7$, —$XR_6$ and —$XC(O)NR_5XR_7$; wherein X is a bond or $C_{1-6}$alkylene; and $R_5$ is selected from hydrogen, $C_{1-6}$alkyl and $C_{3-12}$cycloalkyl-$C_{0-4}$alkyl; $R_6$ is selected from $C_{3-8}$heterocycloalkyl-$C_{0-4}$alkyl and $C_{5-10}$heteroaryl-$C_{0-4}$alkyl optionally substituted by 1 to 3 groups selected from $C_{1-6}$alkyl and —C(O)OH; and $R_7$ is selected from halo and cyano;

$R_3$ is selected from halo, hydroxy, —$XSR_5$, —$XS(O)R_5$, —$XS(O)_2R_5$, —$XC(O)R_5$ and —$XC(O)OR_5$; wherein X is a bond or $C_{1-6}$alkylene; and $R_5$ is selected from hydrogen, $C_{1-6}$alkyl and $C_{3-12}$cycloalkyl-$C_{0-4}$alkyl; or a pharmaceutically acceptable salt thereof.

2. The compound of claim 1 in which:

W is selected from —$NR_4$— and —O—; wherein $R_4$ is selected from hydrogen and $C_{1-6}$alkyl;

$R_1$ is selected from $C_{6-10}$aryl-$C_{0-4}$alkyl and $C_{5-10}$heteroaryl-$C_{0-4}$alkyl; wherein any aryl and heteroaryl of $R_1$ is optionally substituted by 1 to 3 groups independently selected from halo, nitro, $C_{5-10}$heteroaryl, $C_{1-6}$alkyl, $C_{1-6}$alkoxy, halo-substituted-$C_{1-6}$alkyl, —$XNR_5R_5$, —$XOR_5$, —$XSR_5$, —$XNR_5XNR_5R_5$, —$XNR_5XOR_5$, —$XC(O)NR_5R_5$, —$XOXR_6$ and —$XC(O)R_6$; wherein X is a bond or $C_{1-6}$alkylene; $R_5$ is selected from hydrogen, $C_{1-6}$alkyl and $C_{3-12}$cycloalkyl-$C_{0-4}$alkyl; and $R_6$ is selected from $C_{3-8}$heterocycloalkyl-$C_{0-4}$alkyl and $C_{5-10}$heteroaryl-$C_{0-4}$alkyl optionally substituted by 1 to 3 groups selected from $C_{1-6}$alkyl and —C(O)OH; wherein any heteroaryl substituent of $R_1$ is further optionally substituted by 1 to 5 $C_{1-6}$alkyl groups;

$R_2$ is selected from $C_{6-10}$aryl-$C_{0-4}$alkyl and $C_{5-10}$heteroaryl-$C_{0-4}$alkyl; wherein any arylalkyl or heteroarylalkyl of $R_2$ is optionally substituted by 1 to 3 groups independently selected from halo, nitro, cyano, $C_{1-6}$alkyl, $C_{2-6}$alkenyl, $C_{1-6}$alkoxy, halo-substituted-$C_{1-6}$alkyl, $C_{3-8}$heteroaryl$C_{0-4}$alkyl, —$XNR_5R_5$, —$XOR_5$, —$XSR_5$, —$XS(O)_2NR_5R_5$, —$XC(O)OR_5$, —$XOC(O)R_5$, —$XC(O)NR_5XNR_5R_5$, —$XC(O)NR_5XC(O)OR_5$, —$XC(O)NR_5XNR_5C(O)R_5$, —$XC(O)NR_5XNR_5C(O)OR_5$, —$XC(O)NR_5XOR_5$, —$XC(O)N(XOR_5)_2$, —$XNR_5C(O)R_5$, —$XC(O)NR_5R_6$, —$XC(O)R_6$, —$XR_7$, —$XR_6$ and —$XC(O)NR_5XR_7$; wherein X is a bond or $C_{1-6}$alkylene; and $R_5$ is selected from hydrogen, $C_{1-6}$alkyl and $C_{3-12}$cycloalkyl-$C_{0-4}$alkyl; $R_6$ is selected from C$_{3-8}$heterocycloalkyl-C$_{0-4}$alkyl and C$_{5-10}$heteroaryl-C$_{0-4}$alkyl optionally substituted by 1 to 3 groups selected from C$_{1-6}$alkyl and —C(O)OH; and R$_7$ is cyano; and R$_3$ is selected from halo, hydroxy, —XC(O)R$_5$ and —XC(O)OR$_5$; wherein X is a bond or C$_{1-6}$alkylene; and R$_5$ is selected from hydrogen, C$_{1-6}$alkyl and C$_{3-12}$cycloalkyl-C$_{0-4}$alkyl; or a pharmaceutically acceptable sale thereof.

3. The compound of claim 1 in which W is selected from —NH— and —O—; and R$_1$ is selected from phenyl, benzyl, 5,6,7,8-tetrahydro-naphthalenyl, benzo[1,3]dioxolyl, 1H-indazol-7-yl, indan-4-yl and 1H-indolyl; wherein any R$_1$ is optionally substituted by 1 to 3 groups independently selected from methoxy, methyl, amino, halo, hydroxymethyl, hydroxy, quinoxalinyl, ethyl, pyridinyl, methoxy-phenyl, piperazinyl-carbonyl, 2-(4-methyl-piperazin-1-yl)-ethoxy, isopropyl, methyl-sulfanyl, tri-fluoro-methyl, ethoxy, 3-isopropylamino-propylamino, dimethyl-amino, morpholino, cyclopropyl-methoxy, butoxy, cycloheptyl-oxy and 1,4,5,7-tetramethyl-pyrrolo[3,4-d]pyridazinyl; or a pharmaceutically acceptable salt thereof.

4. The compound of claim 1 in which R$_2$ is selected from pyridinyl, phenyl, thiazolyl, pyridinyl-methyl, pyridinyl-ethyl, thiophenyl, benzyl, quinolinyl, 7-oxo-5,6,7,8-tetrahydro-naphthalenyl, naphthyl and pyrimidinyl; wherein any arylalkyl or heteroarylalkyl of R$_2$ is optionally substituted by 1 to 3 groups independently selected from halo, nitro, cyano, methyl, propyl-sulfamoyl, methyl-sulfamoyl, methoxy, methyl-carboxy, carboxy, amino, cyano-ethyl, cyano-methyl, ethenyl, tri-fluoro-methyl, hydroxy-methyl, ethyl, methyl-sulfanyl, butyl, isobutyl, carboxy-methyl-formamidyl, 1-carboxy-ethyl-formamidyl, carboxy-ethyl, amino-ethyl-formamidyl, amino-propyl-formamidyl, dimethyl-amino-ethyl-formamidyl, dimethyl-amino-propyl-formamidyl, dimethyl-amino-butyl-formamidyl, methyl-formamidyl, ethyl-formamidyl, ethyl-formamidyl-methyl, N-(2-(dimethylamino)ethyl)-3-phenylpropanamide, 2-(2-dimethylamino-formamidyl)-ethyl, 2-(amino-ethyl-formamidyl)-ethyl, 2-(amino-propyl-formamidyl) -ethyl, 2-(propyl-formamidyl)-ethyl, amino-propyl-formamidyl-methyl, morpholino-ethyl-formamidyl, morpholino-carbonyl-methyl, amino-ethyl-formamidyl-methyl, cyclobutyl-formamidyl, methyl -formamidyl-methyl, dimethyl-formamidyl-methyl, hydroxy-ethyl-formamidyl-methyl, hydroxy-propyl -formamidyl-methyl, N,N-bis-(3-hydroxy-propyl)-formamidyl, cyclopentyl-formamidyl, isobutyl-formamidyl, isobutyl-formamidyl-methyl, cyclopentyl-formamidyl-methyl, cyano-ethyl-formamidyl, cyano-methyl-formamidyl, pyrrolidinyl-ethyl-formamidyl, 2-(isobutyl-formamidyl)-ethyl, 1H-tetrazolyl, 2-(1H-tetrazol-5-yl)-ethyl, 2-(1H-tetrazol-5-yl)-methyl, 2-(1-methyl-1H-tetrazol-5-yl) -methyl, acetyl-amino, cyclopropyl-formamidyl-methyl, hydroxy-ethyl-formamidyl, hydroxy-propyl-formamidyl, propyl-formamidyl-methyl, ethoxy-propyl-formamidyl, acetyl-amino-ethyl-formamidyl, 1-methyl-piperidin-4-yl-formamidyl, morpholino-carbonyl-ethyl, methoxy-carbonyl-methyl, methoxy-carbonyl-ethyl-formamidyl, methoxy-carbonyl-ethyl-formamidyl-methyl, methoxy-carbonyl-methyl-formamidyl-methyl, methoxy-carbonyl-methyl-formamidyl, acetyl-amino-ethyl-formamidyl-methyl, ethoxy-propyl-formamidyl-methyl, methoxy-carbonyl-ethyl, 1-formyl -pyrrolidin-2-yl-carboxylic acid, (1-carboxy-3-methyl-butyl)-formamidyl, 2-(methoxy-carbonyl-methyl-formamidyl)-ethyl, 1-carboxy-(2,2-dimethyl-propyl)-formamidyl, 3-tert-butoxycarbonyl-amino-propyl-formamidyl, acetoxy-formamidyl, acetoxy-methyl and 1-carboxy-ethyl-formamidyl; or a pharmaceutically acceptable salt thereof.

5. The compound of claim 1 in which n is 0 or 1; and R$_3$ is selected from halo, hydroxy, —C(O)OH and —C(O)OCH$_3$; or a pharmaceutically acceptable salt thereof.

6. The compound of claim 1 of Formula Ig:

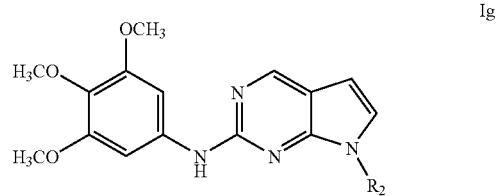

Ig in which R$_2$ is selected from pyridinyl, phenyl, thiazolyl, pyridinyl-methyl, pyridinyl-ethyl, thiophenyl, benzyl, quinolinyl, 7-oxo-5,6,7,8-tetrahydro-naphthalenyl, naphthyl and pyrimidinyl;

wherein any arylalkyl or heteroarylalkyl of R$_2$ is optionally substituted by 1 to 3 groups independently selected from halo, nitro, cyano, methyl, propyl-sulfamoyl, methyl-sulfamoyl, methoxy, methyl-carboxy, 2-dimethylamino-ethyl-formamyl, carboxy, amino, cyano-ethyl, cyano-methyl, ethenyl, tri-fluoro-methyl, hydroxy-methyl, ethyl, methyl-sulfanyl, butyl, isobutyl, carboxy-methyl-formamidyl, 1-carboxy-ethyl-formamidyl, carboxy-ethyl, amino-ethyl-formamidyl, amino-propyl-formamidyl, dimethyl-amino-ethyl-fornnamidyl, dimethyl-amino-propyl-formamidyl, dimethyl-amino-butyl-formamidyl, methyl-formamidyl, ethyl-formamidyl, ethyl-formamidyl-methyl, N-(2-(dimethylamino)ethyl)-3-phenylpropanaide, 2-(2-dimethylamino-formamidyl)-ethyl, 2-(amino -ethyl-formamidyl)-ethyl, 2-(amino-propyl-formamidyl)-ethyl, 2-(propyl-formamidyl)-ethyl, amino- propyl-formamidyl-methyl, morpholino-ethyl-formamidyl, morpholino-carbonyl-methyl, amino-ethyl-formamidyl-methyl, cyclobutyl-formamidyl, methyl-formamidyl-methyl, dimethyl-formamidyl-methyl, hydroxy-ethyl -formamidyl-methyl, hydroxy-propyl-formamidyl-methyl, N,N-bis-(3-hydroxy-propyl)-formamidyl, cyclopentyl-formamidyl, isobutyl-formamidyl, isobutyl-formamidyl-methyl, cyclopentyl-formamidyl-methyl, cyano-ethyl-formamidyl, cyano-methyl-formamidyl, pyrrolidinyl-ethyl -formamidyl, 2-(isobutyl-formamidyl)-ethyl, 1H-tetrazolyl, 2-(1H-tetrazol-5-yl)-ethyl, 2-(1H-tetrazol -5-yl)-methyl, 2-(1-methyl-1H-tetrazol-5-yl)-methyl, acetyl-amino, cyclopropyl-formamidyl-methyl, hydroxy-ethyl-fornnannidyl, hydroxy-propyl-formamidyl, propyl-formamidyl-methyl, ethoxy-propyl -formamidyl, acetyl-amino-ethyl-formamidyl, 1-methyl-piperidin-4-yl-formamidyl, morpholino -carbonyl-ethyl, methoxy-carbonyl-methyl, methoxy-carbonyl-ethyl-formamidyl, methoxy -carbonyl-ethyl-formamidyl-methyl, methoxy-carbonyl-methyl-formamidyl-methyl, methoxy -carbonyl-methyl-formamidyl, acetyl-amino-ethyl-formamidyl-methyl, ethoxy-propyl-formamidyl-methyl, methoxy -carbonyl-ethyl, 1-formyl-pyrrolidin-2-yl-carboxylic acid, (1-carboxy-3-methyl-butyl)-formamidyl, 2-(methoxy-carbonyl-methyl-formamidyl)-ethyl, 1-carboxy-(2,2-dimethyl-propyl)-formamidyl, 3-tert -butoxycarbonyl-amino-propyl-formamidyl, acetoxy-methyl and 1-carboxy-ethyl-formamidyl; or a pharmaceutically acceptable salt thereof.

7. A pharmaceutical composition comprising a therapeutically effective amount of a compound of claim 1, or a pharmaceutically acceptable salt thereof, in combination with a pharmaceutically acceptable excipient.
8. A compound selected from:
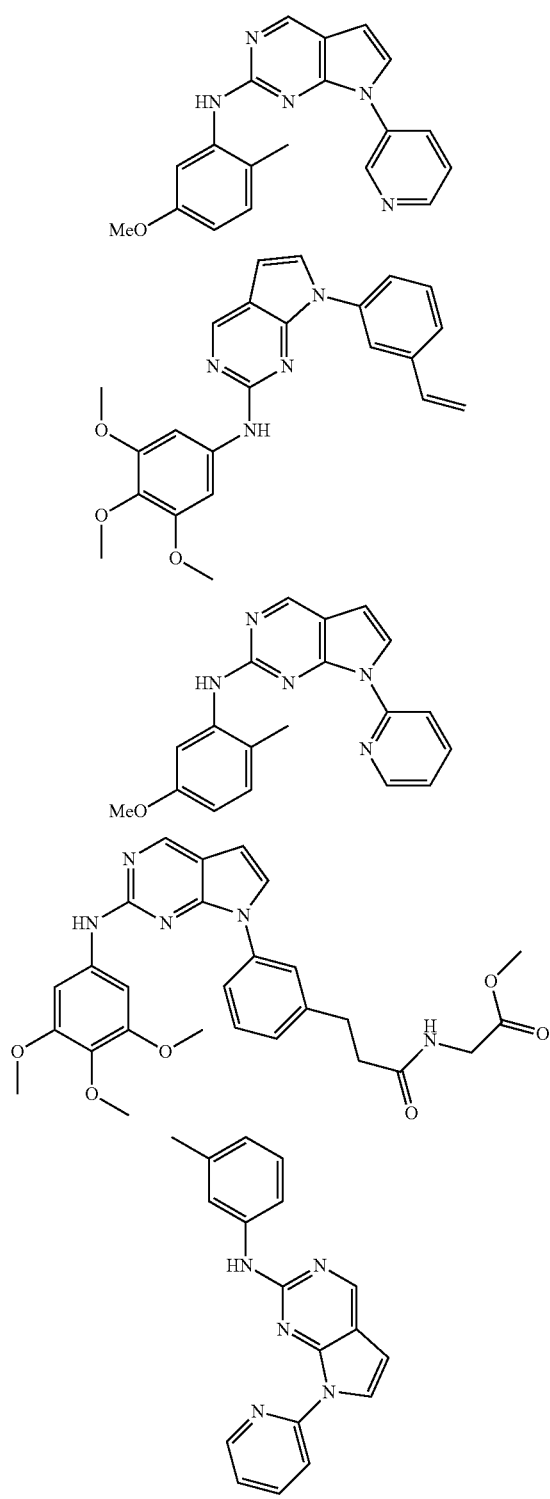
-continued
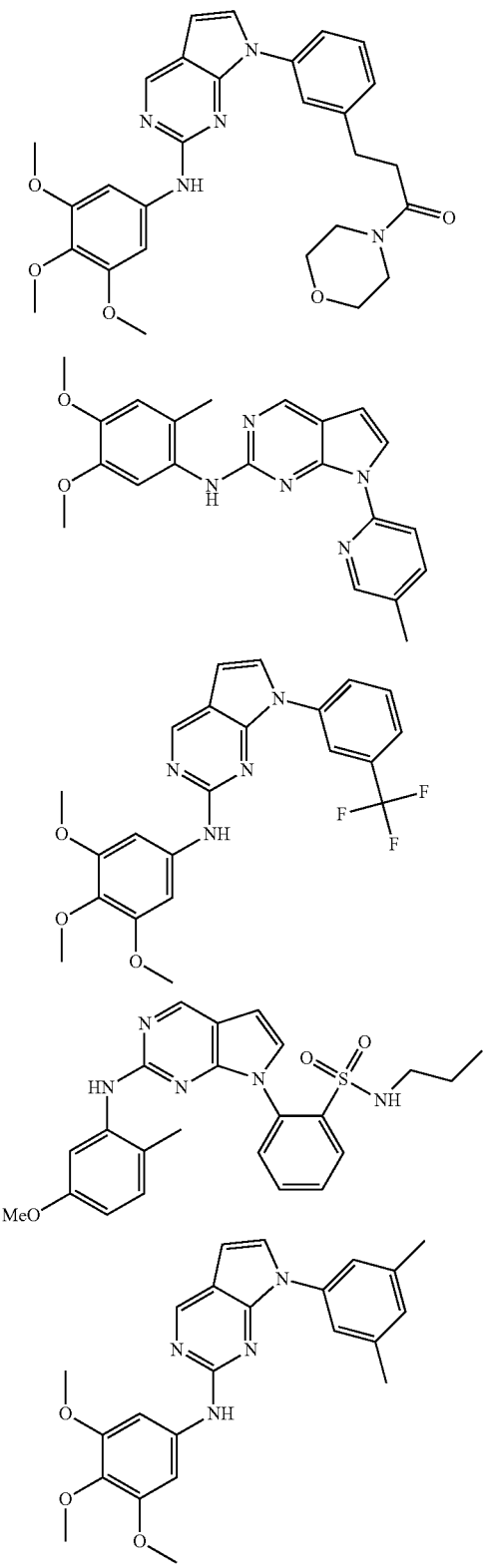

135
-continued
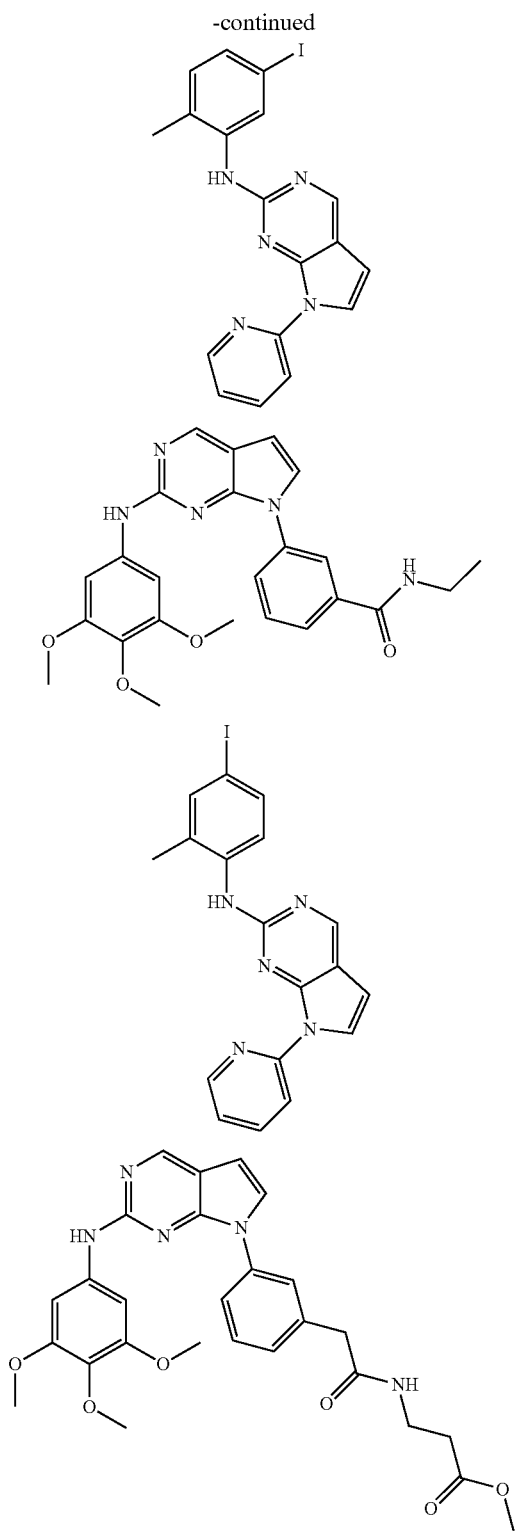
136
-continued
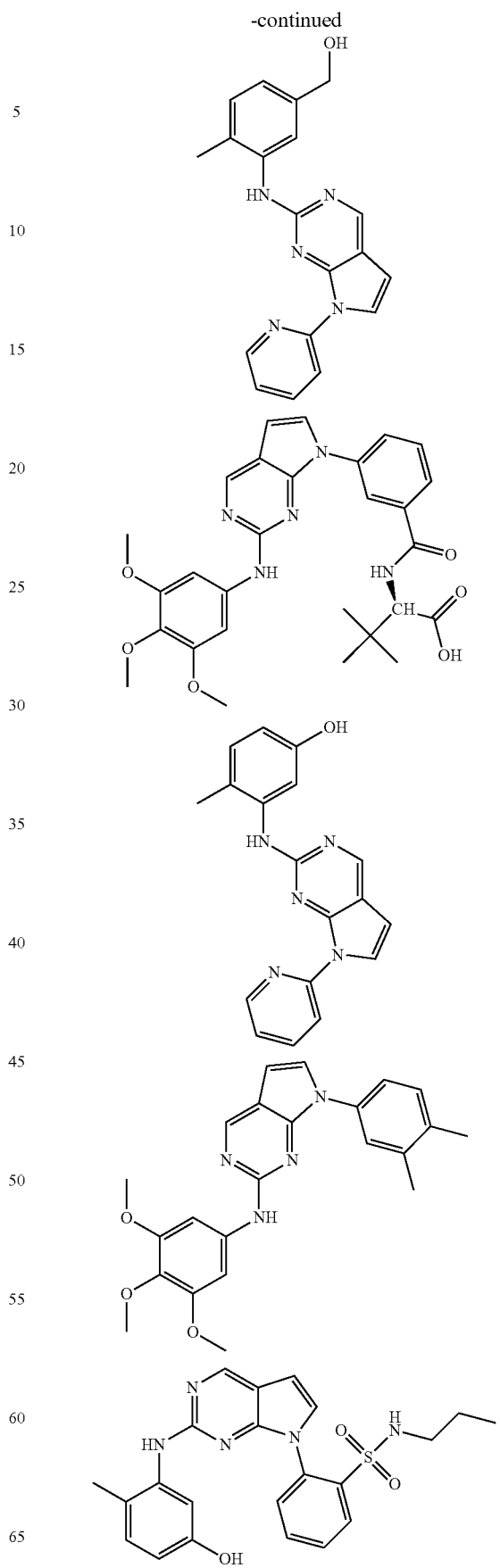

137
-continued
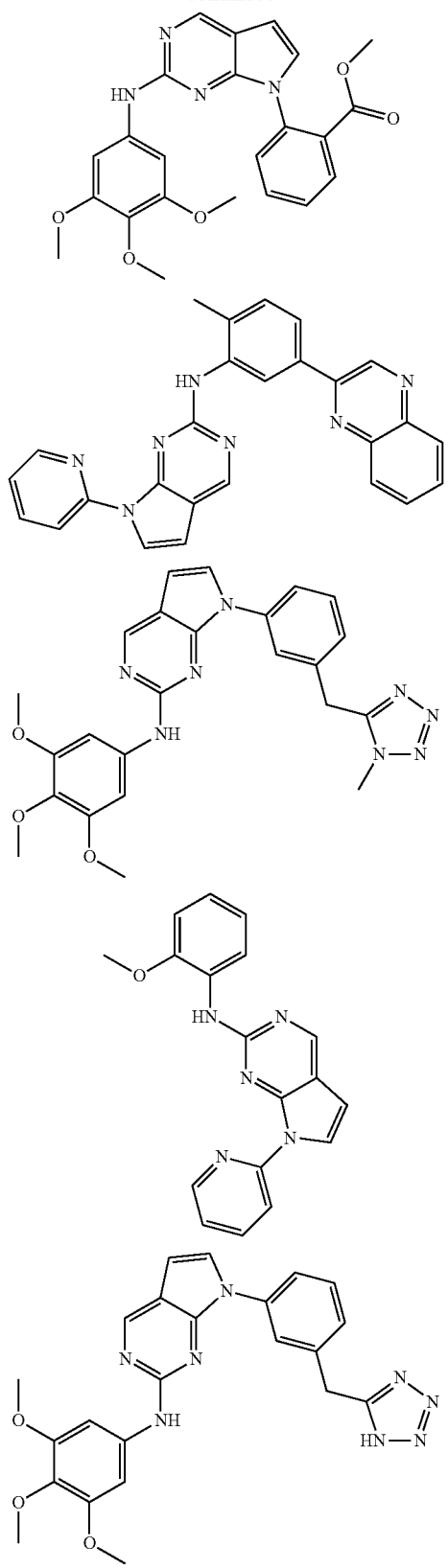
138
-continued
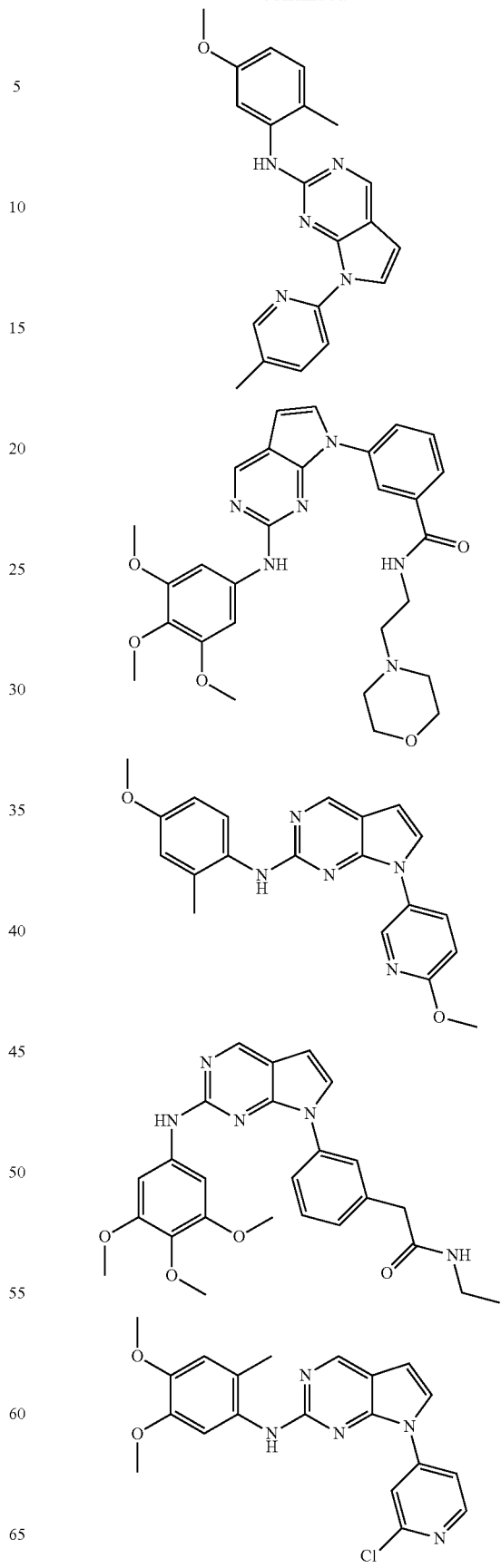

139 -continued
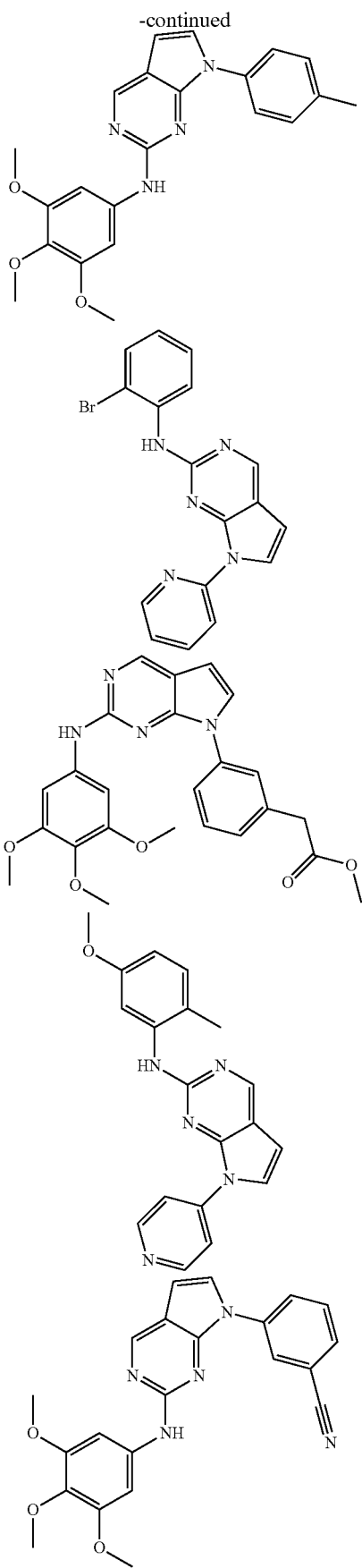
140 -continued
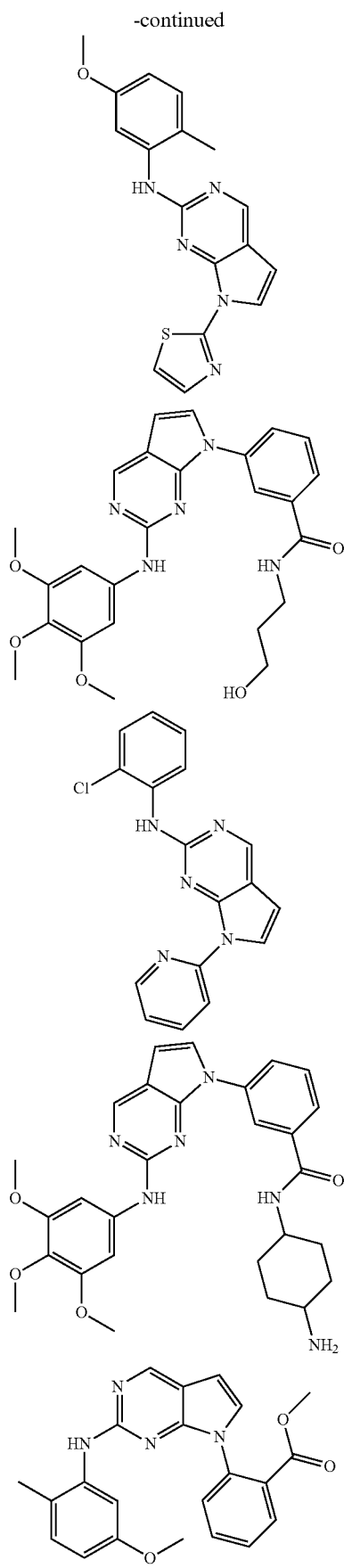

141
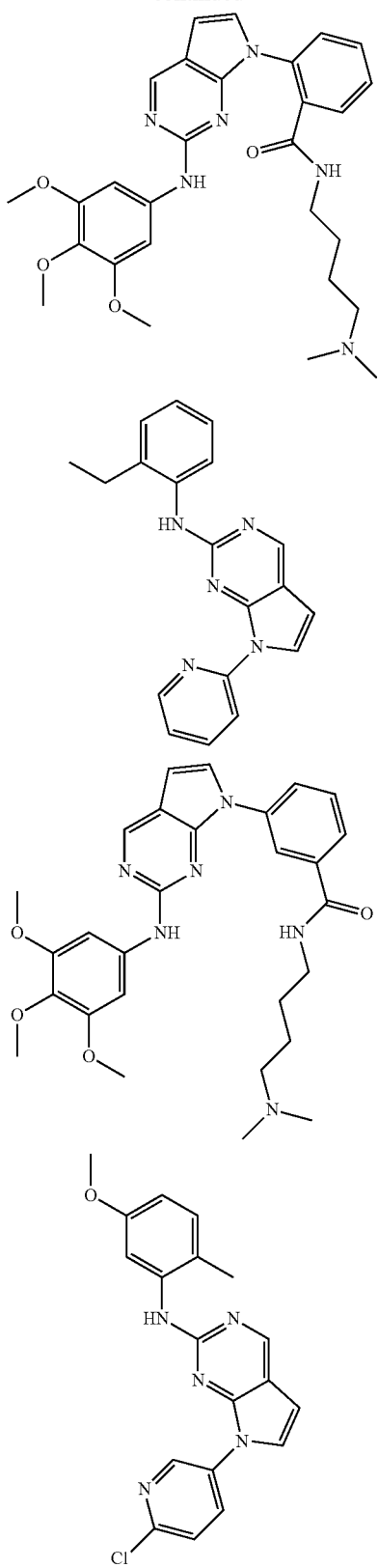
142
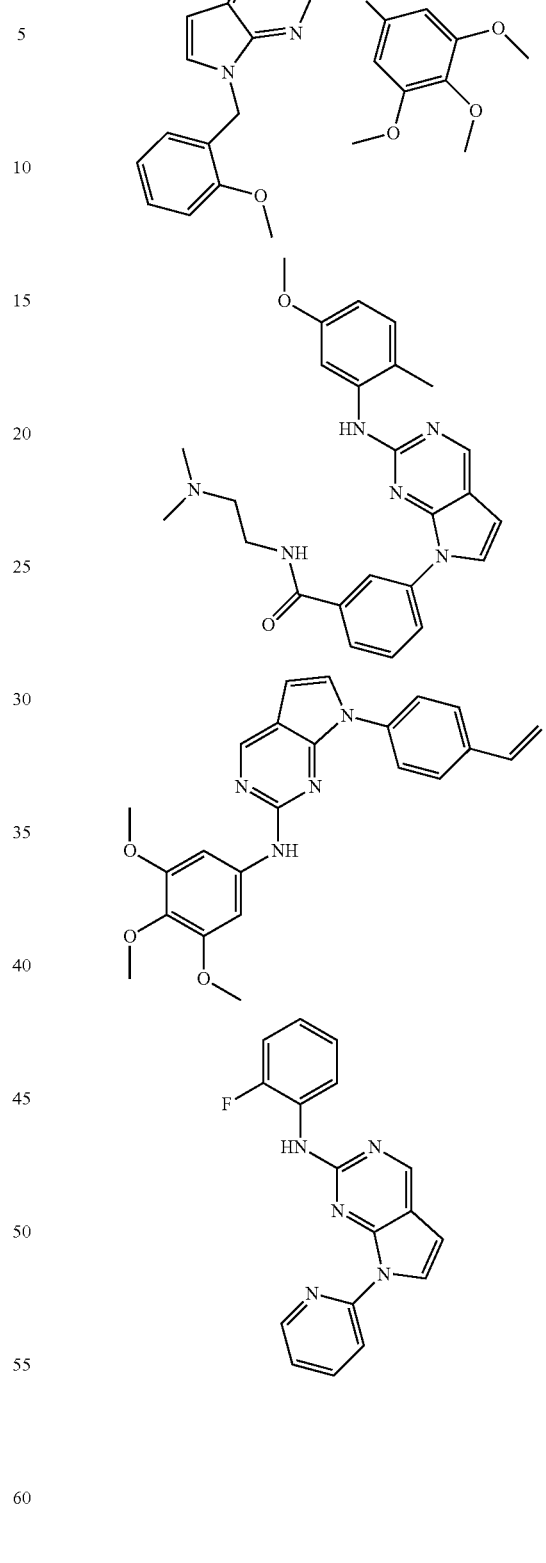

143
-continued
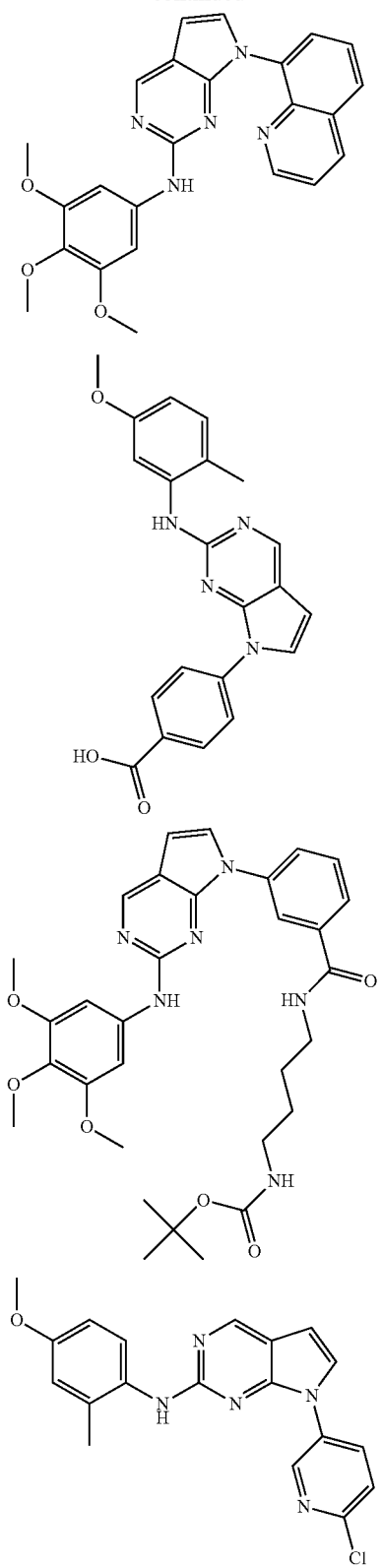
144
-continued
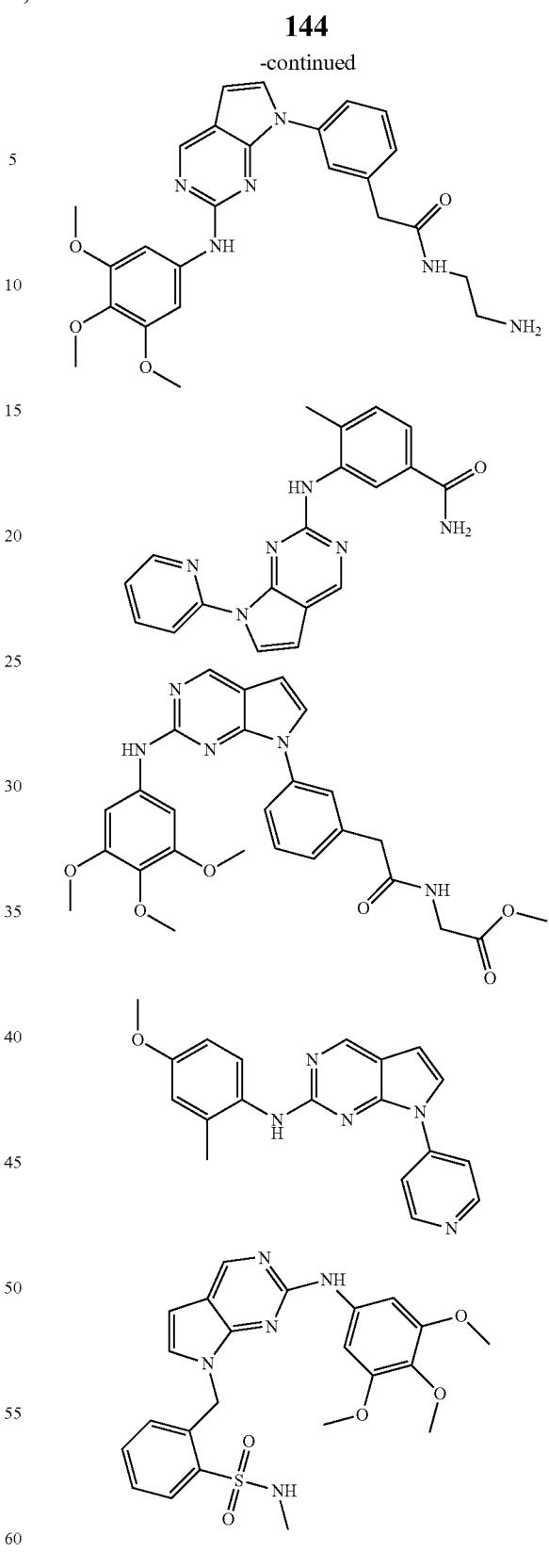

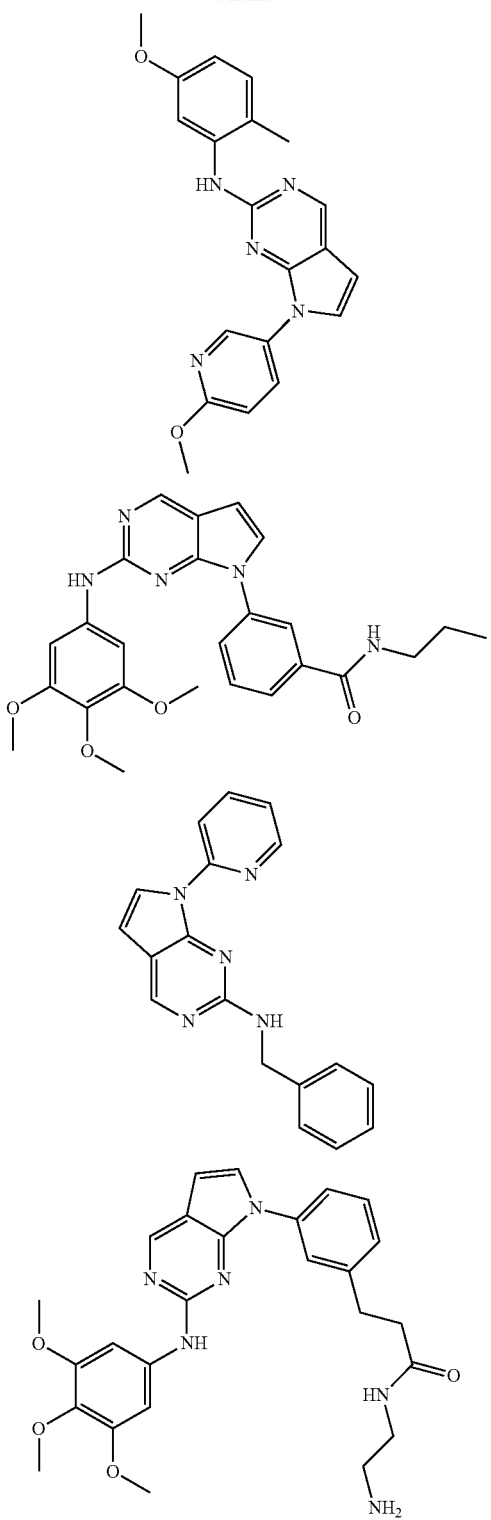
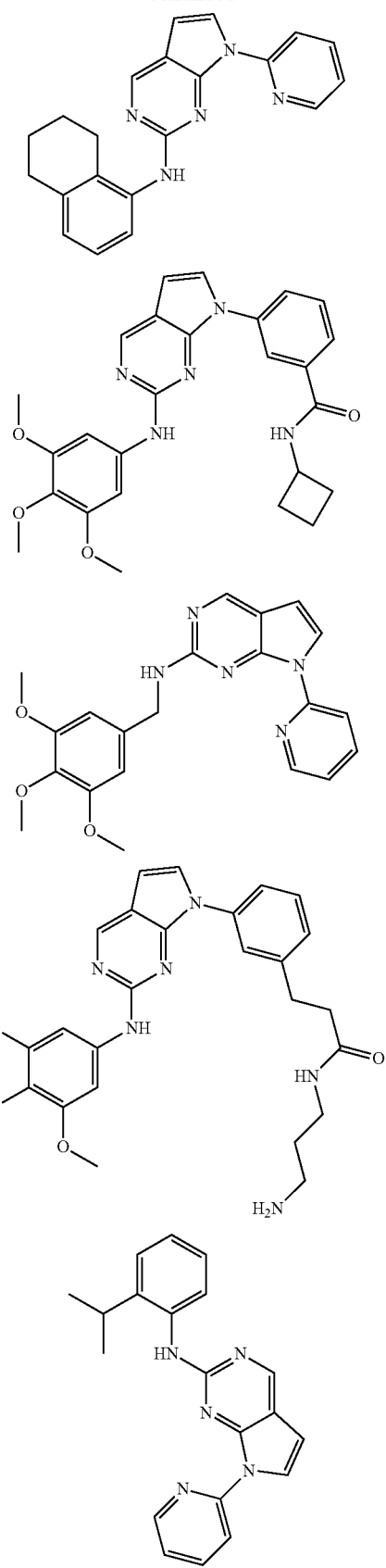

147
-continued
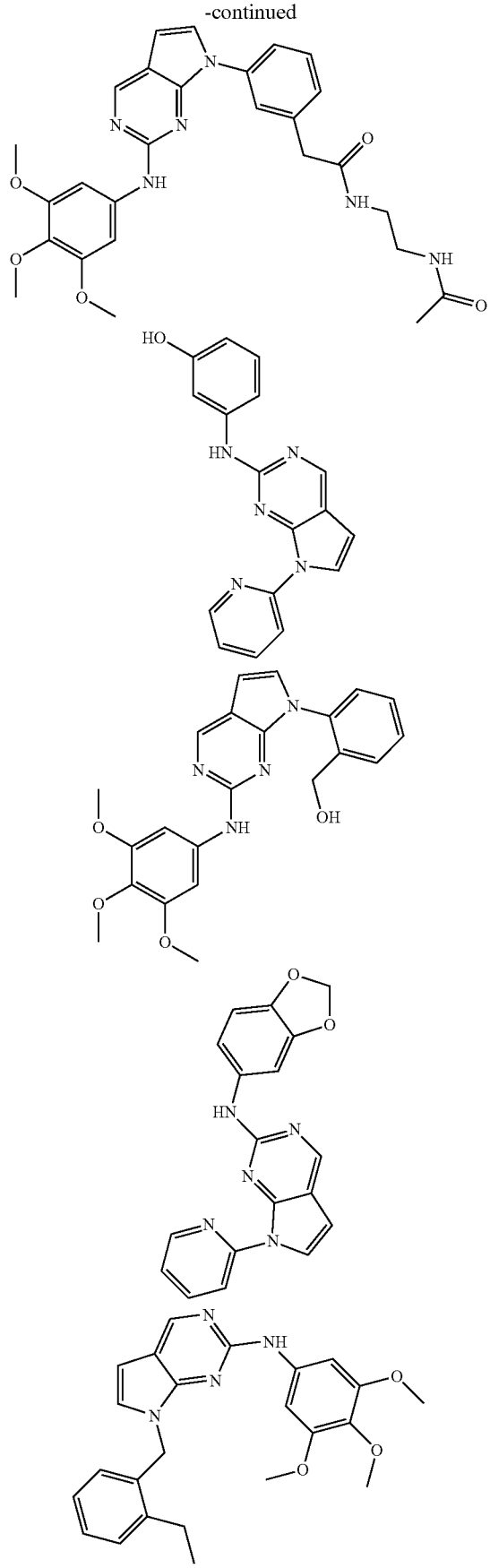
148
-continued
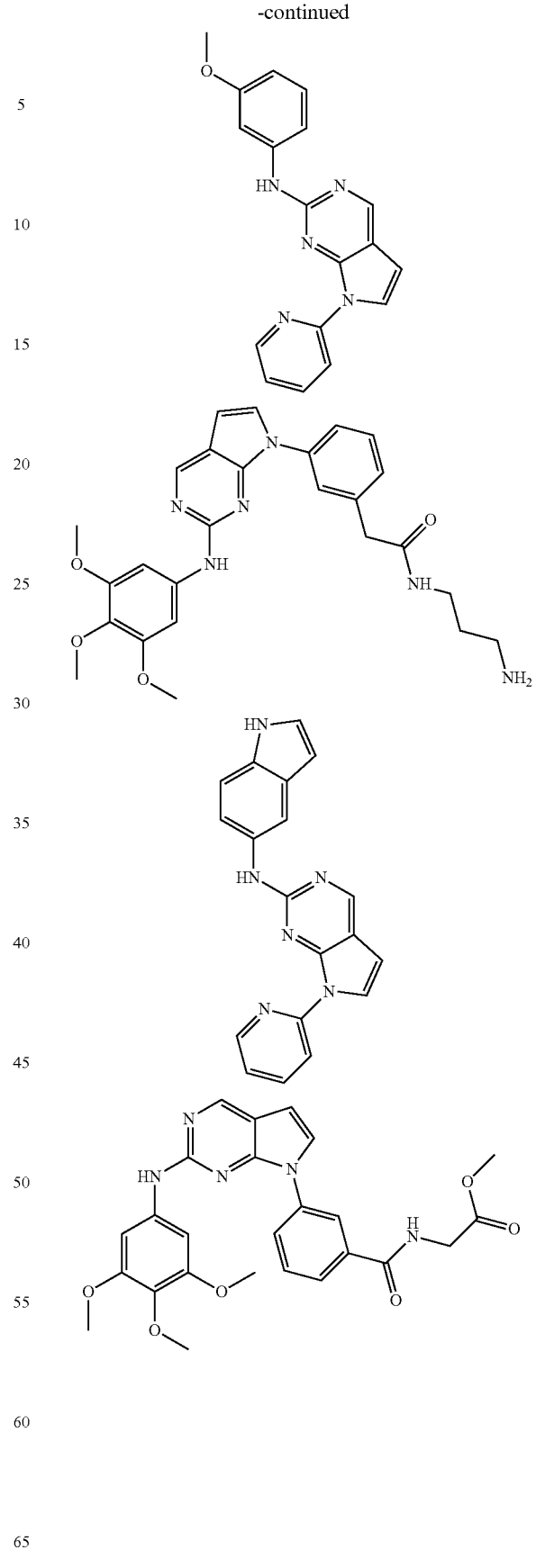

149
-continued
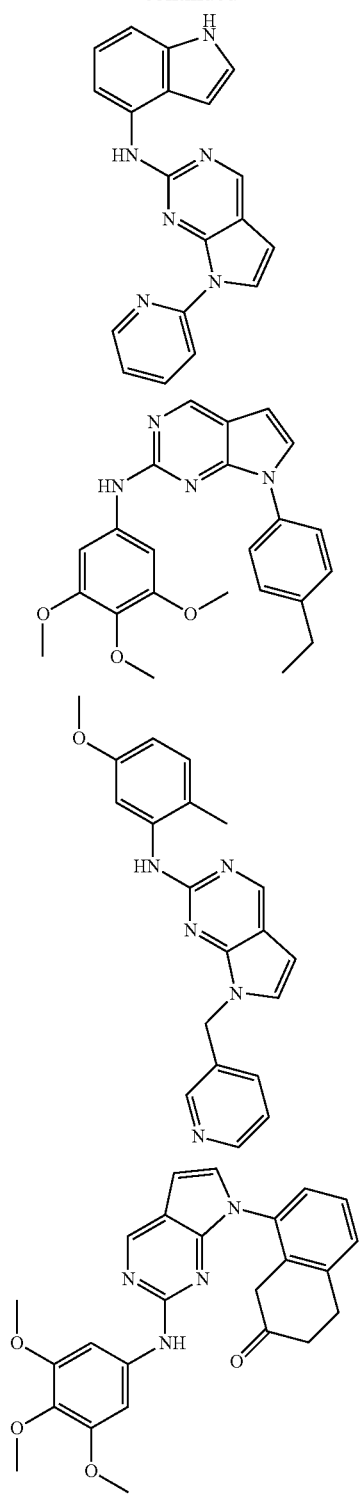
150
-continued
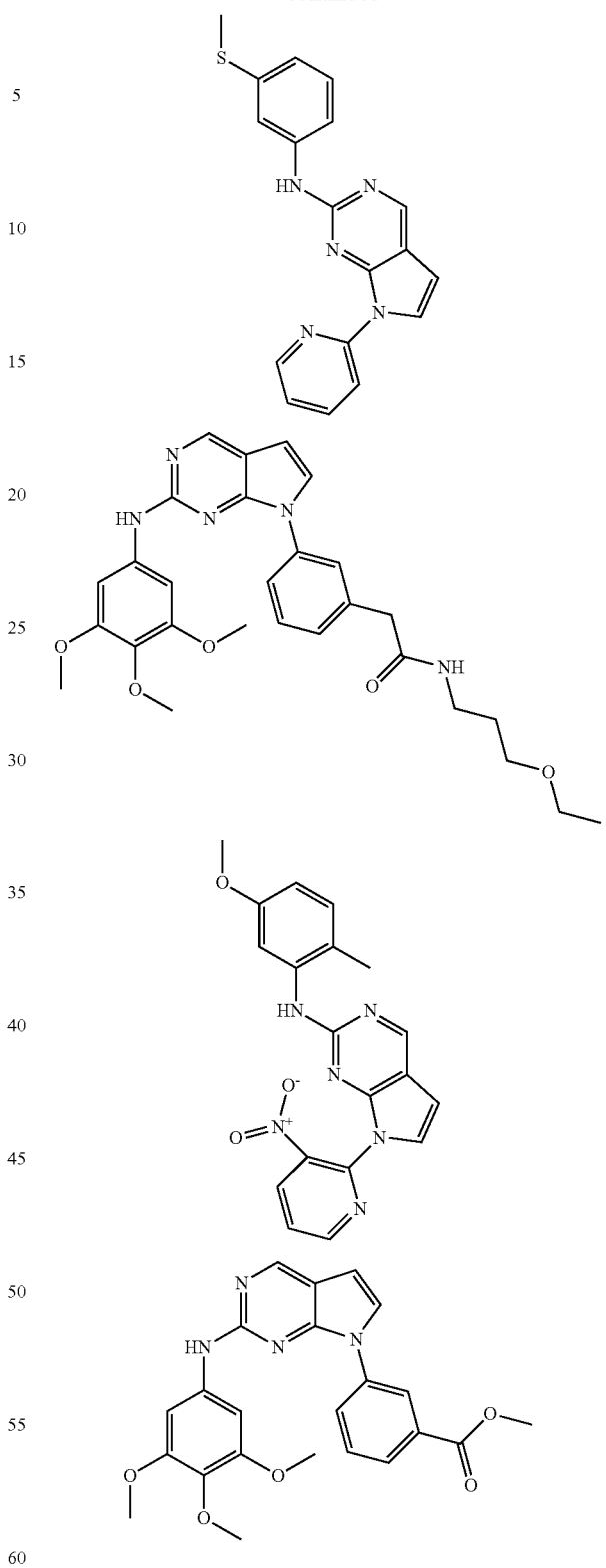

151
-continued
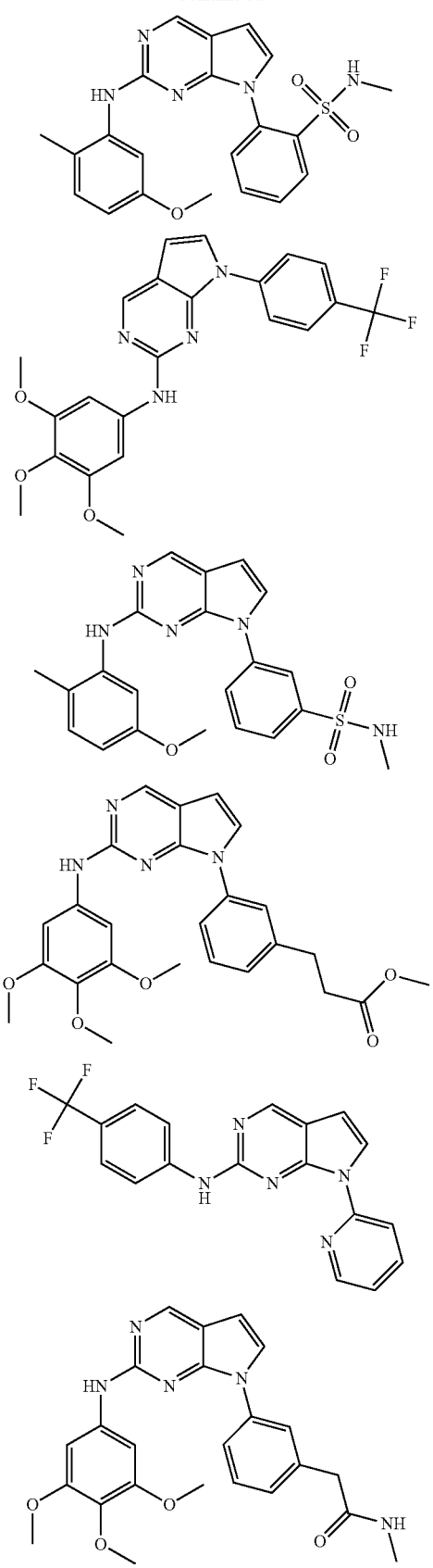
152
-continued
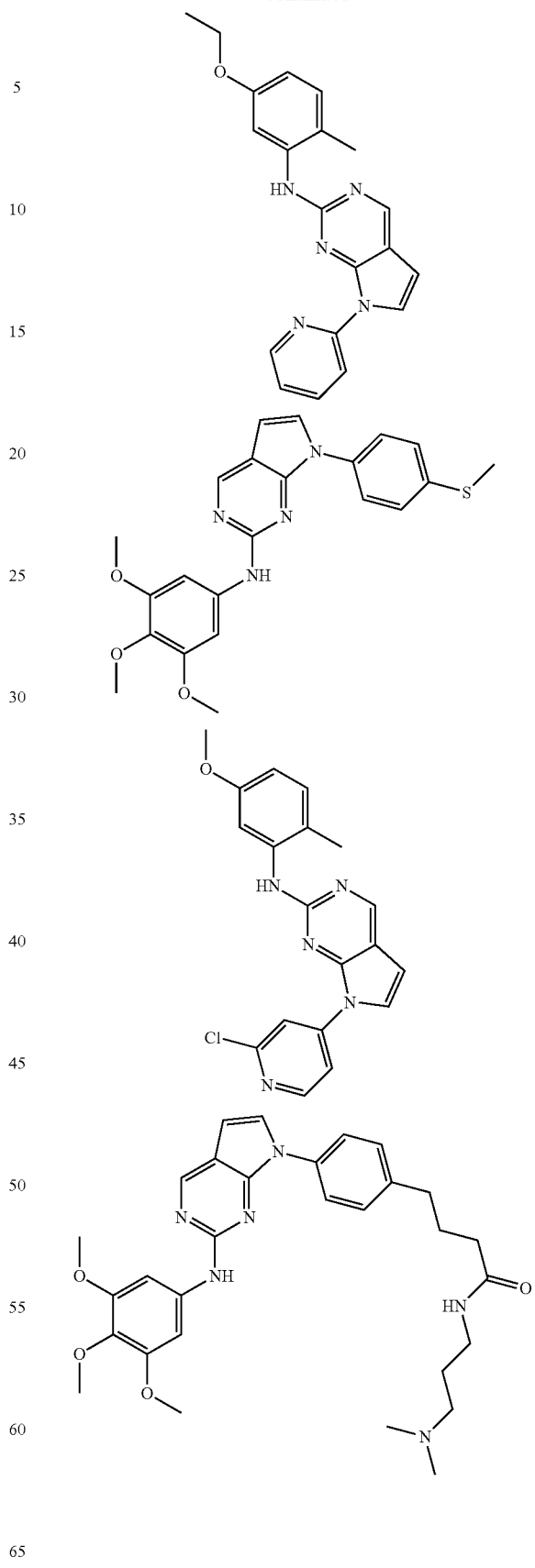

153
-continued
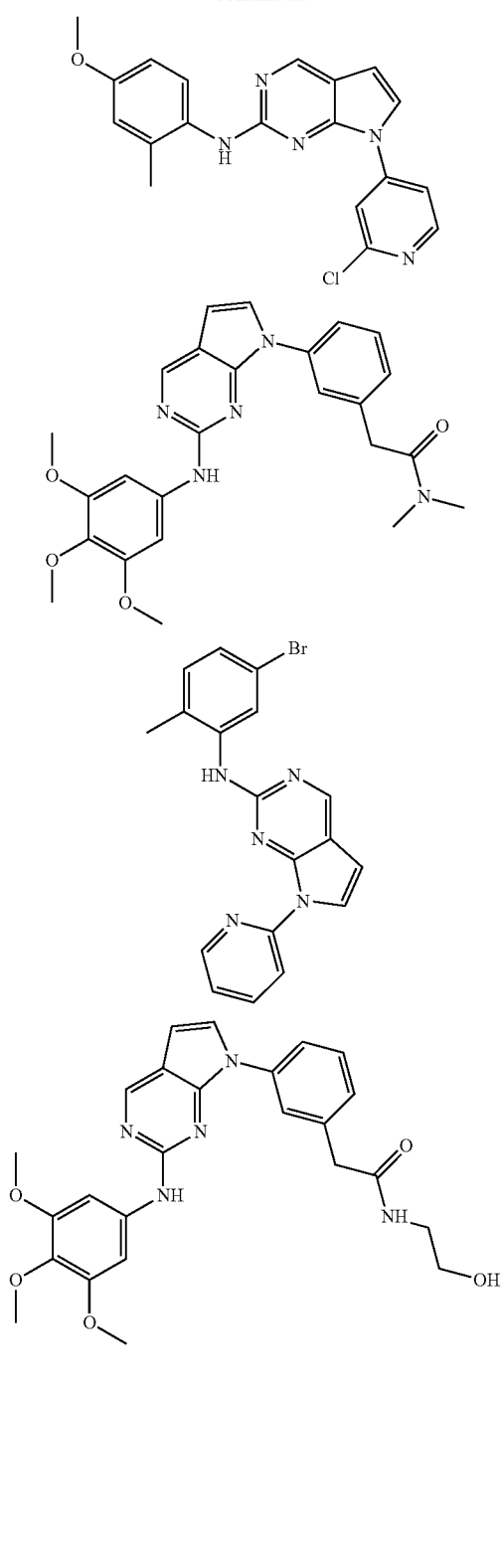
154
-continued
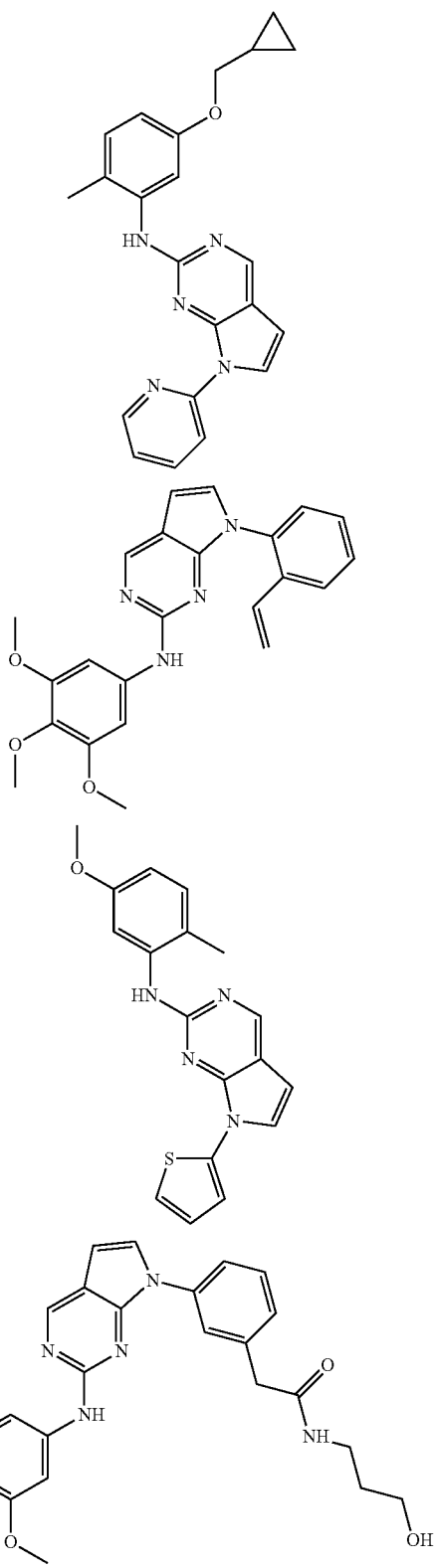

155
-continued
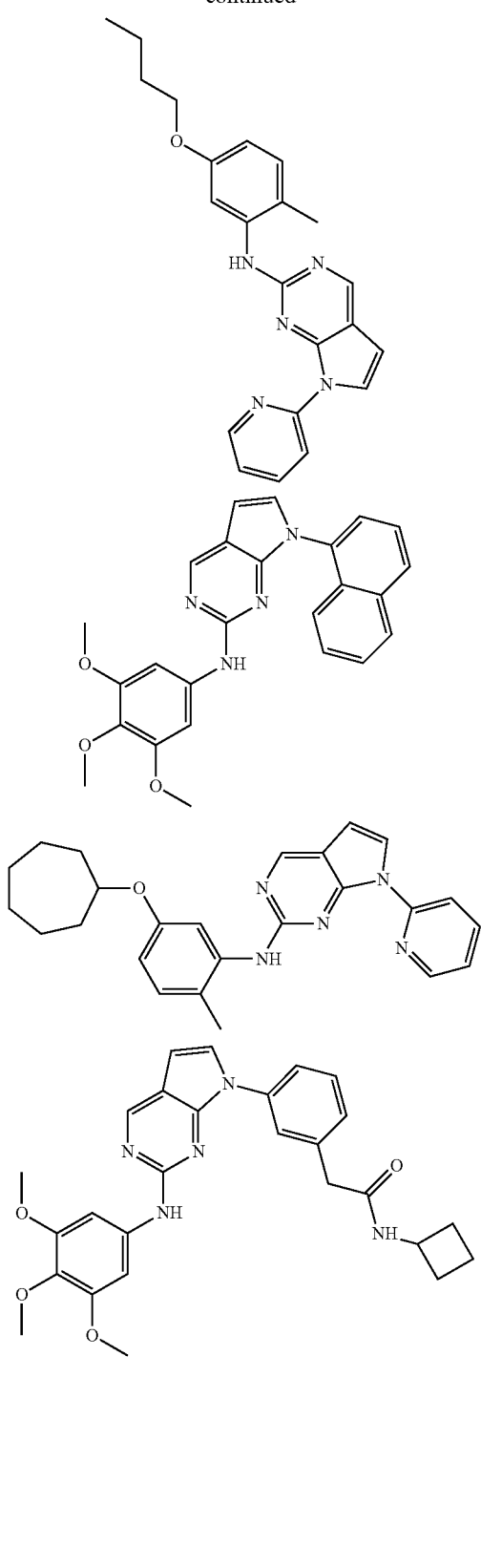
156
-continued
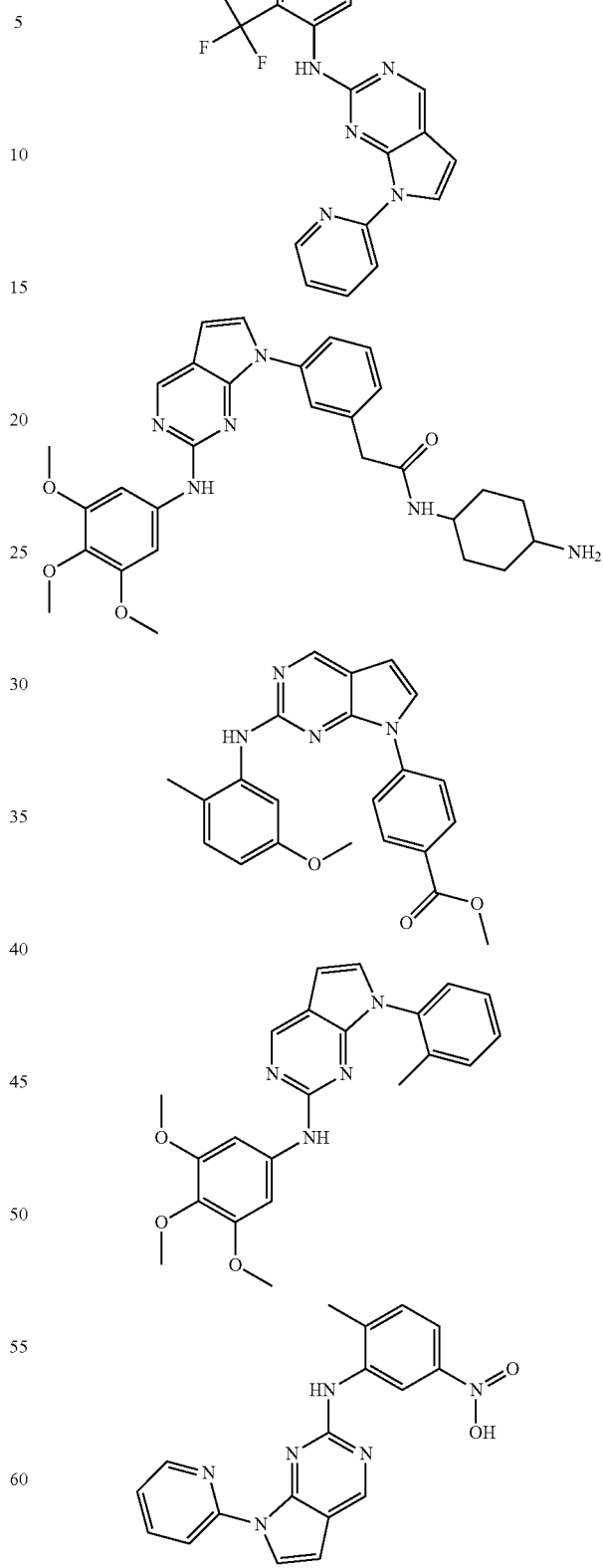

157
-continued
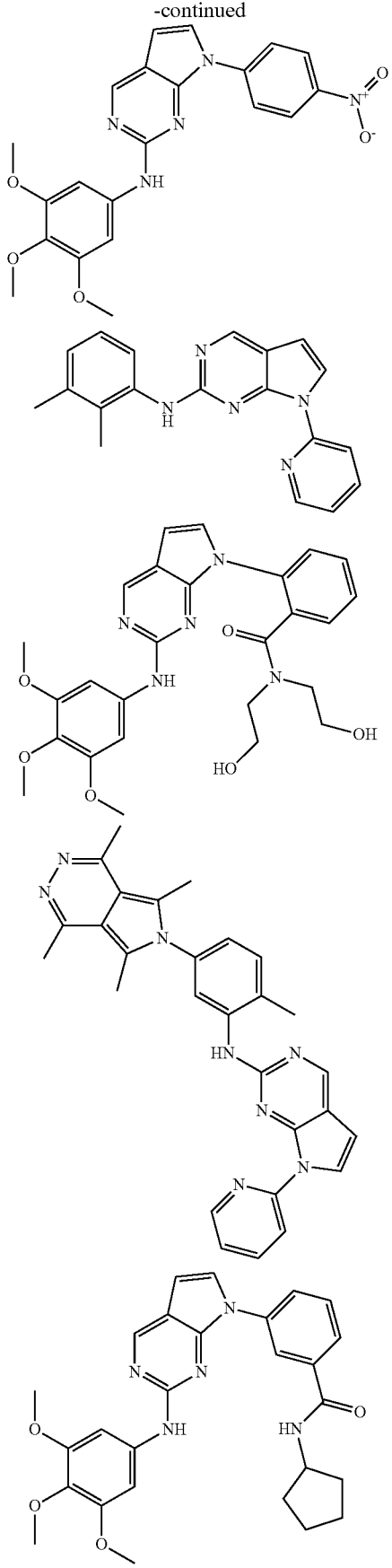
158
-continued
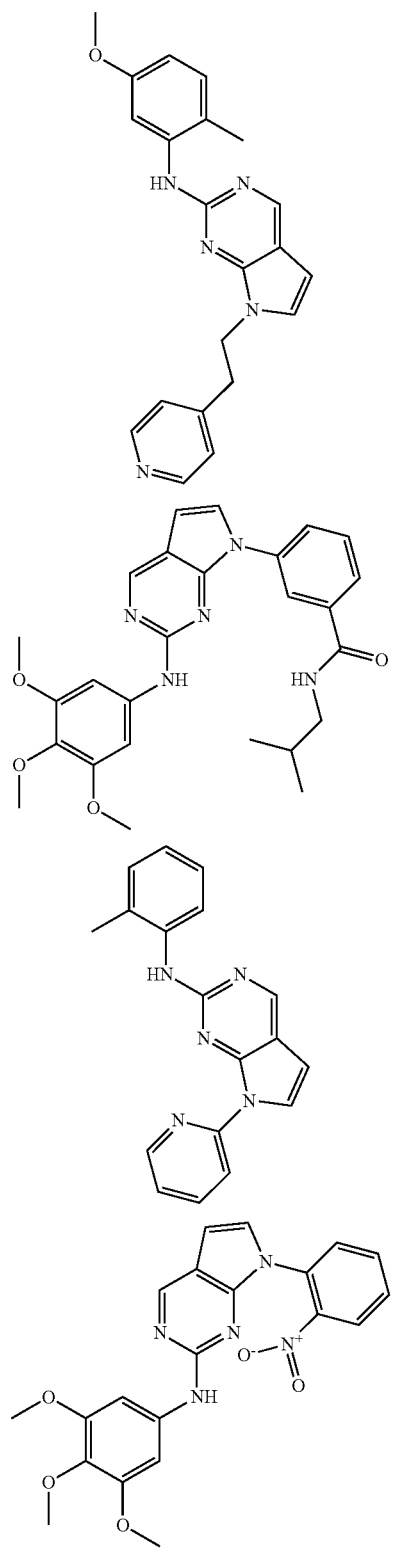

159
-continued
160
-continued
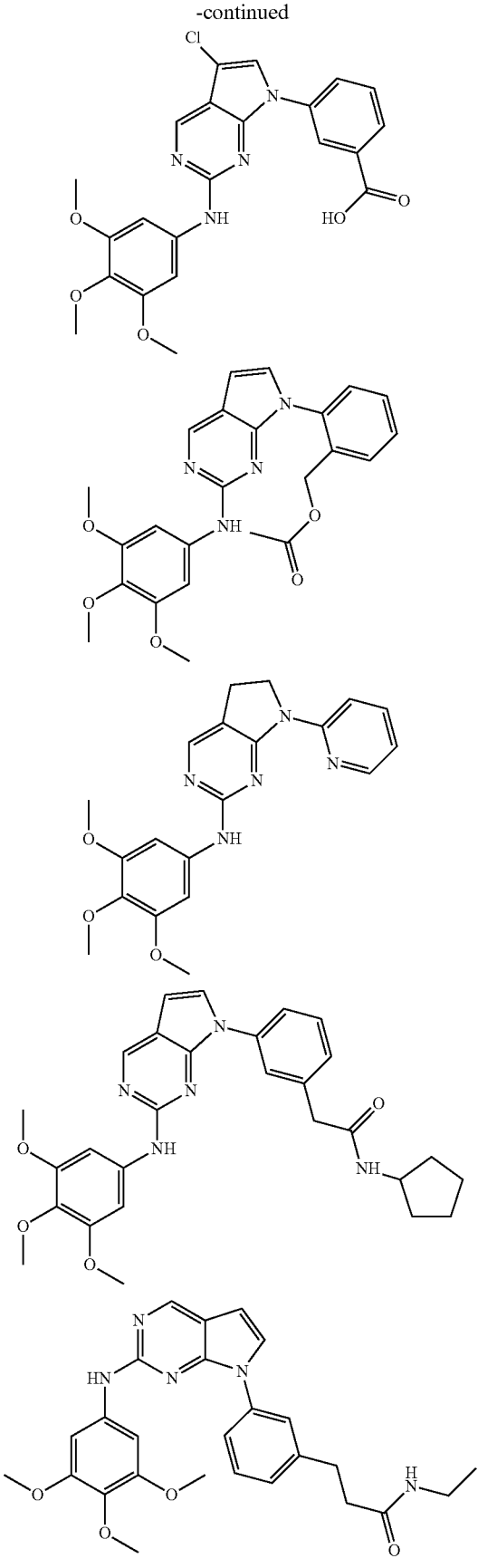
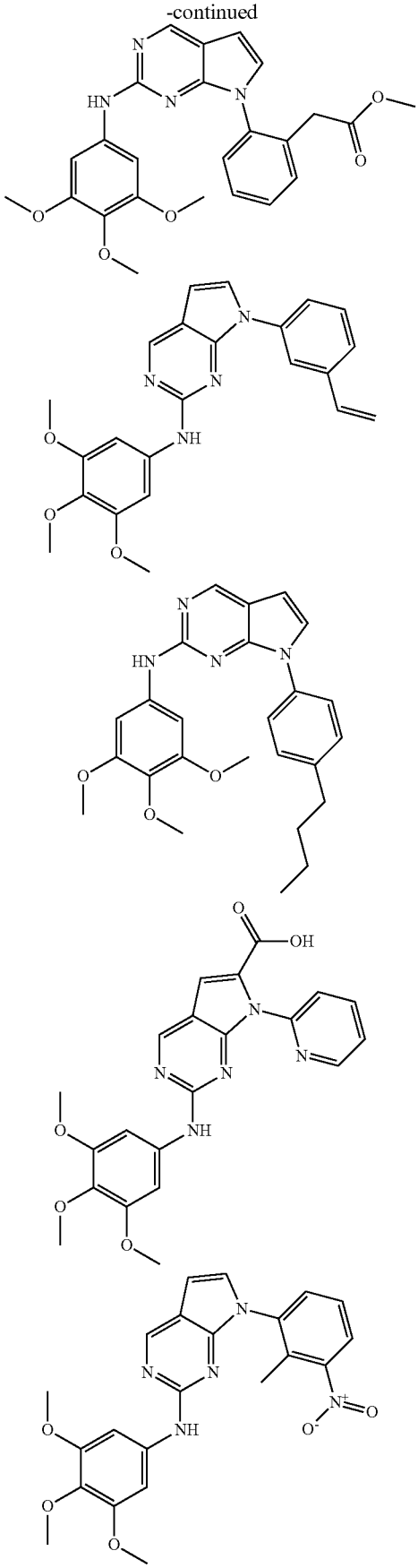

161
-continued
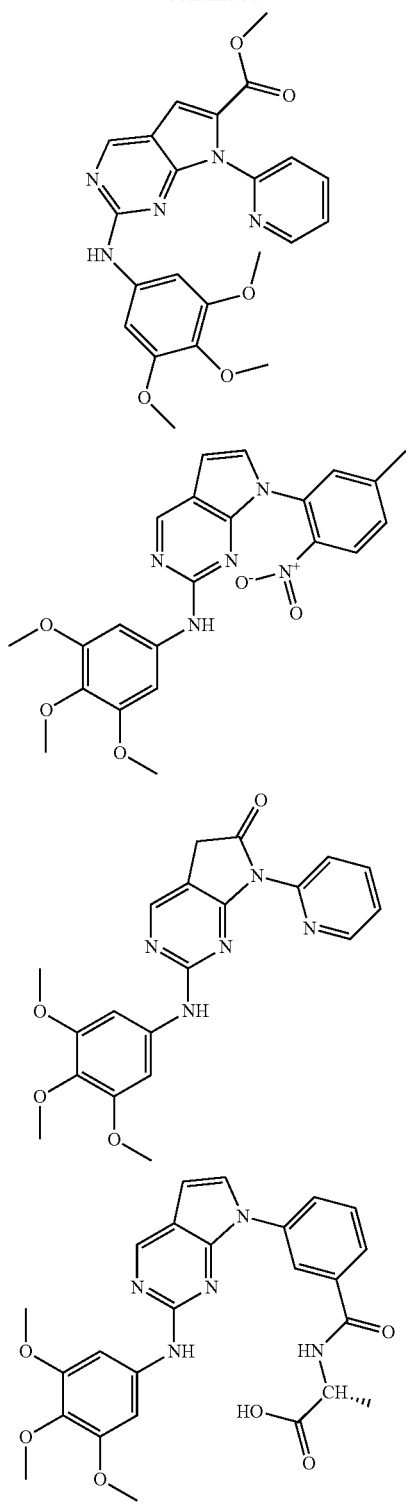
162
-continued
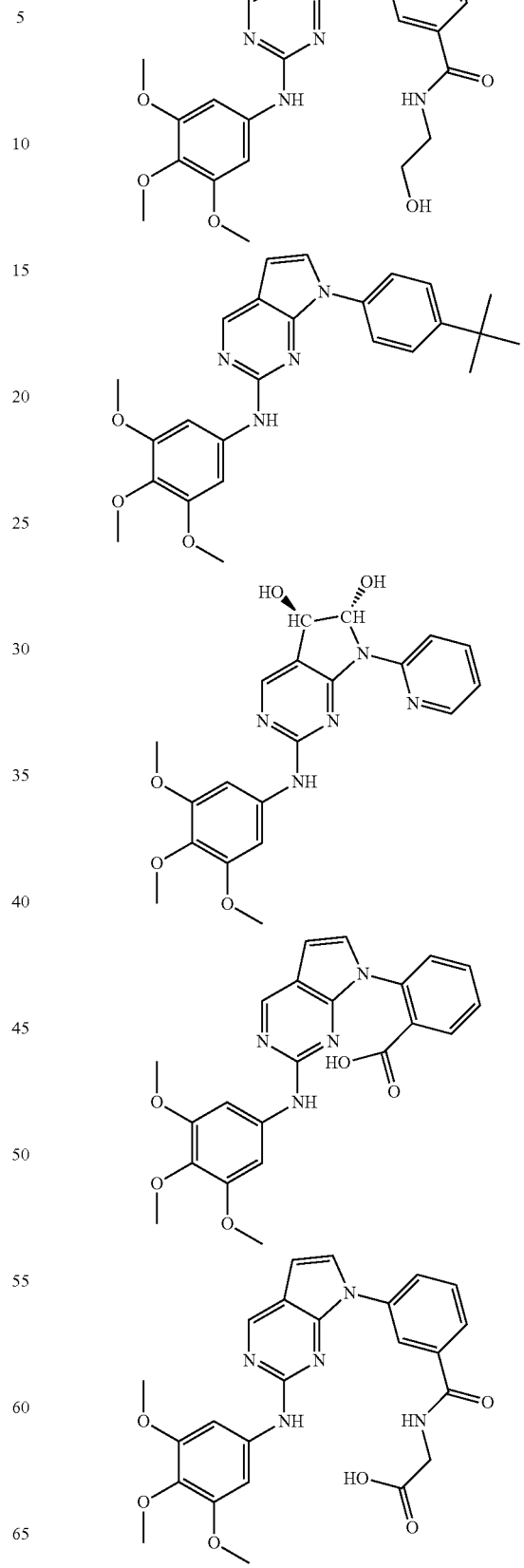

163
-continued
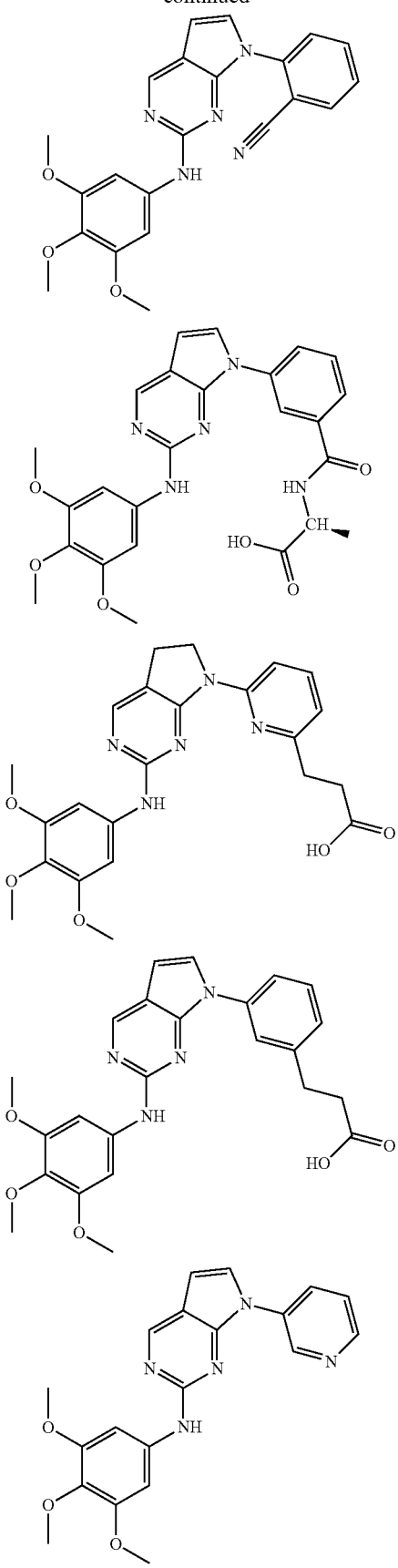
164
-continued
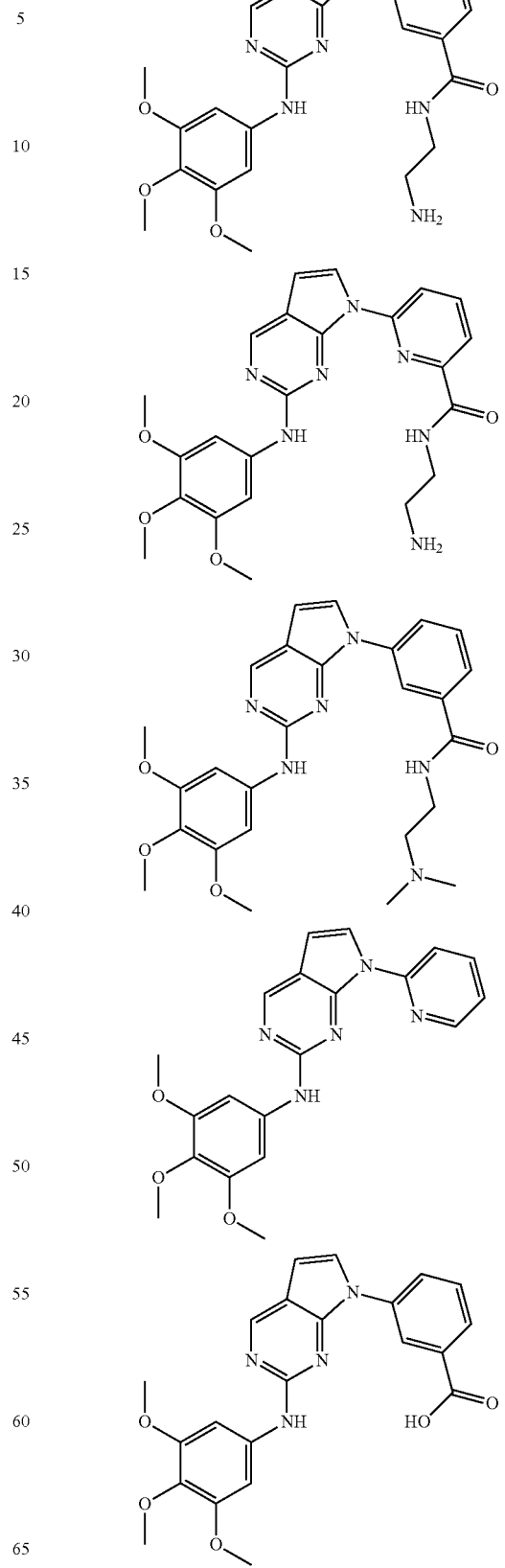

165
-continued
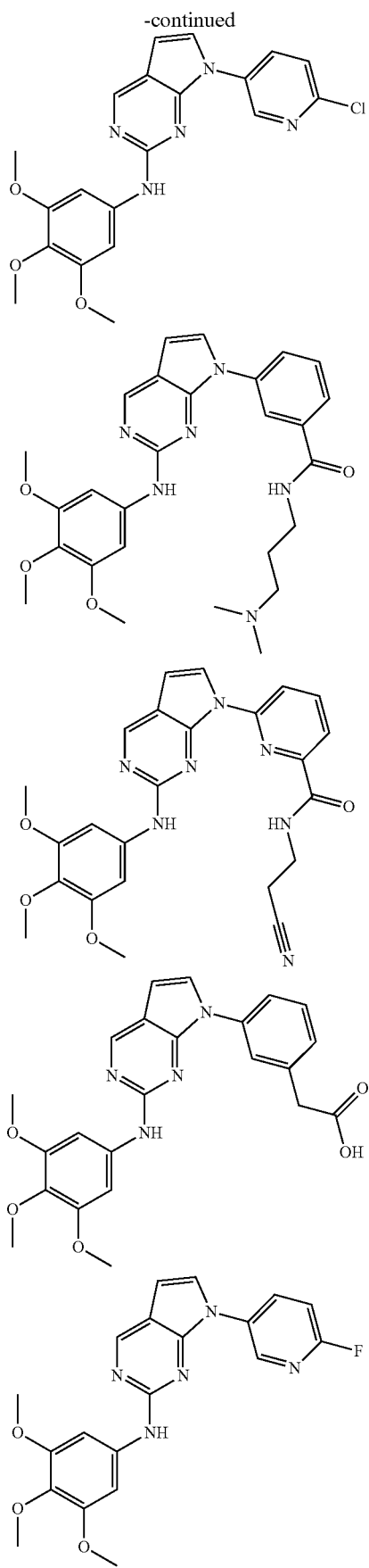
166
-continued
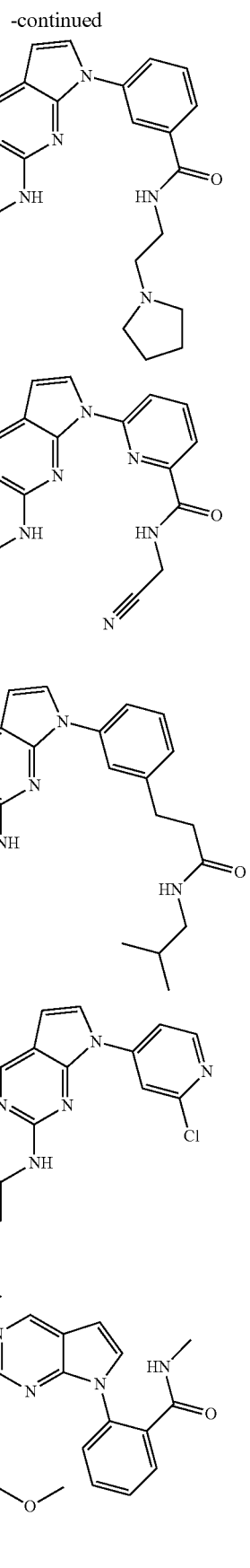

167
-continued
168
-continued
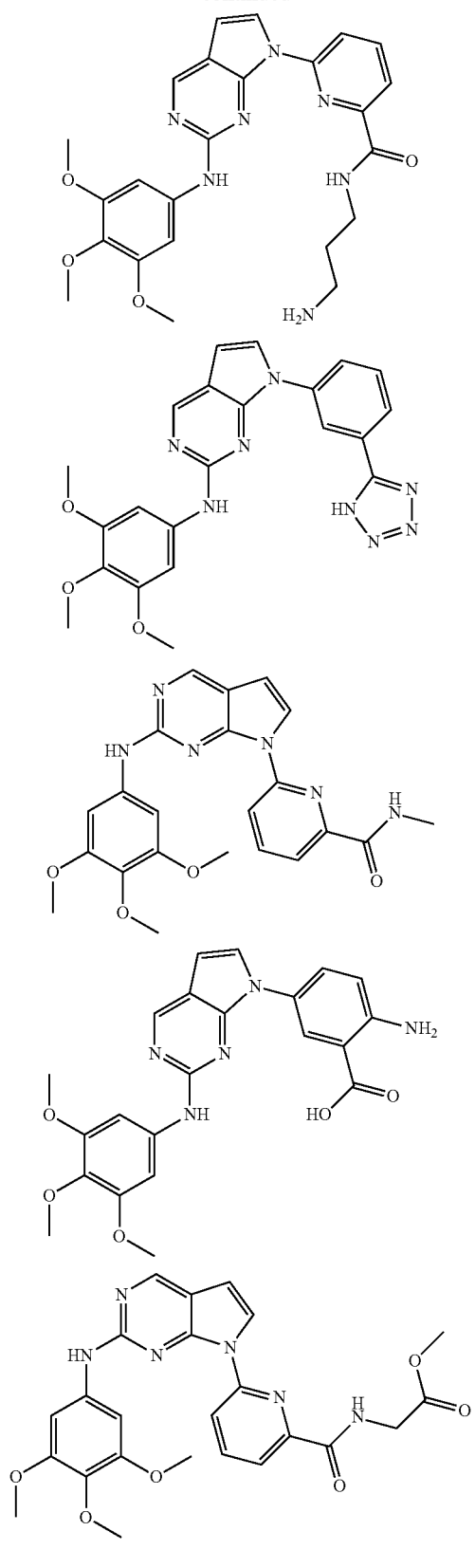
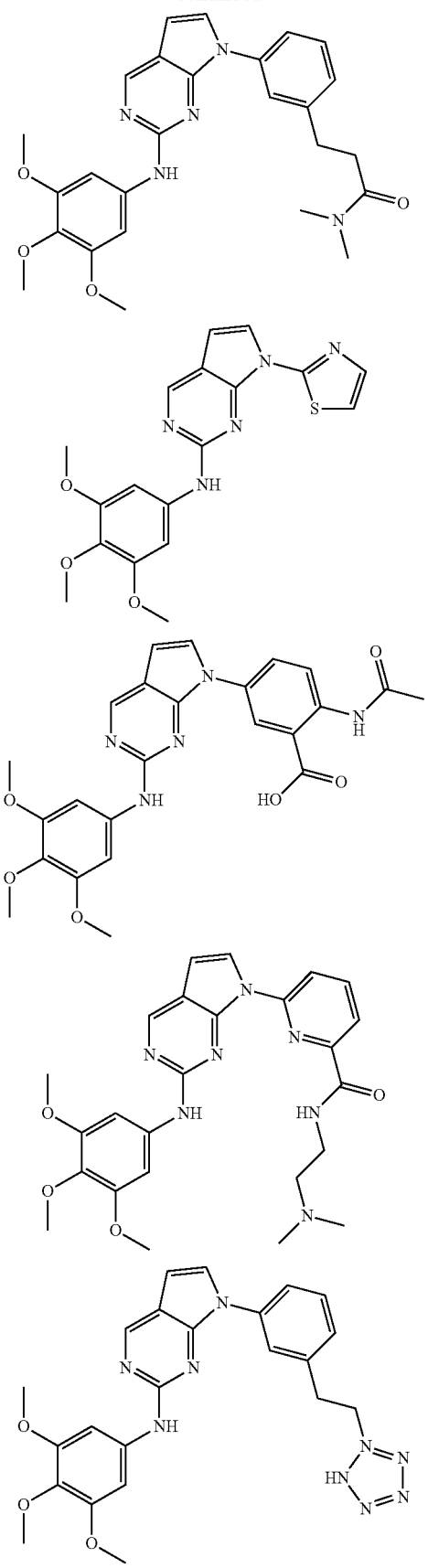

169
-continued
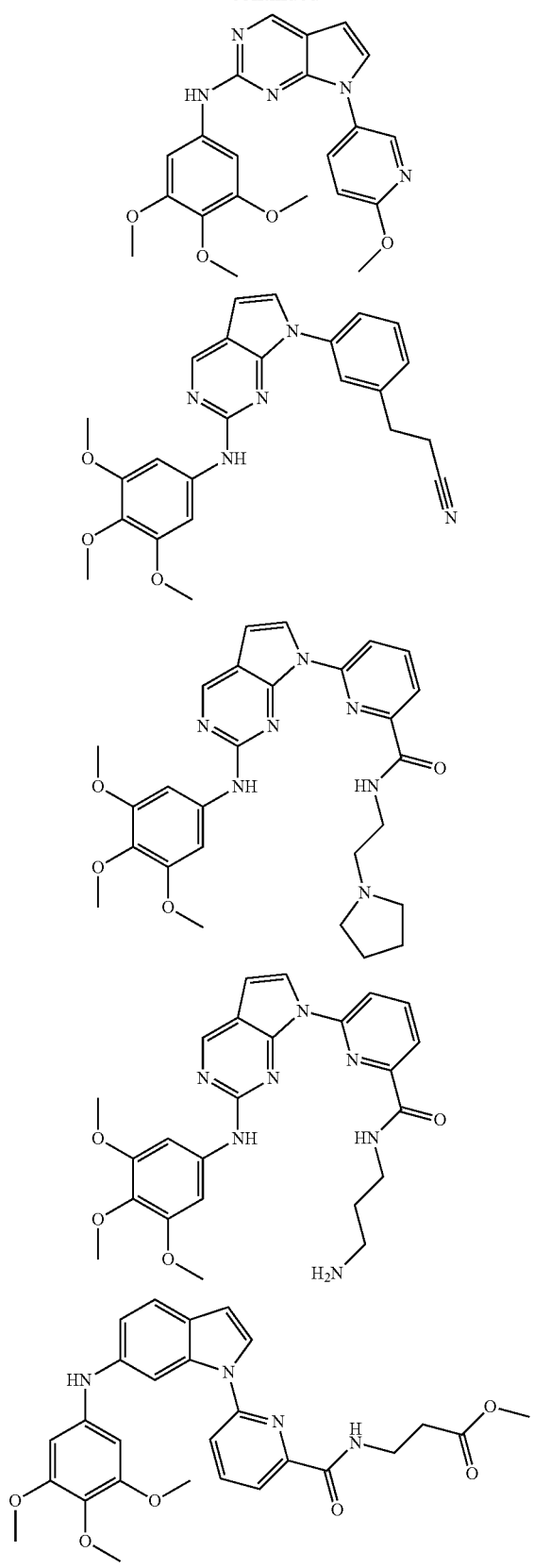
170
-continued
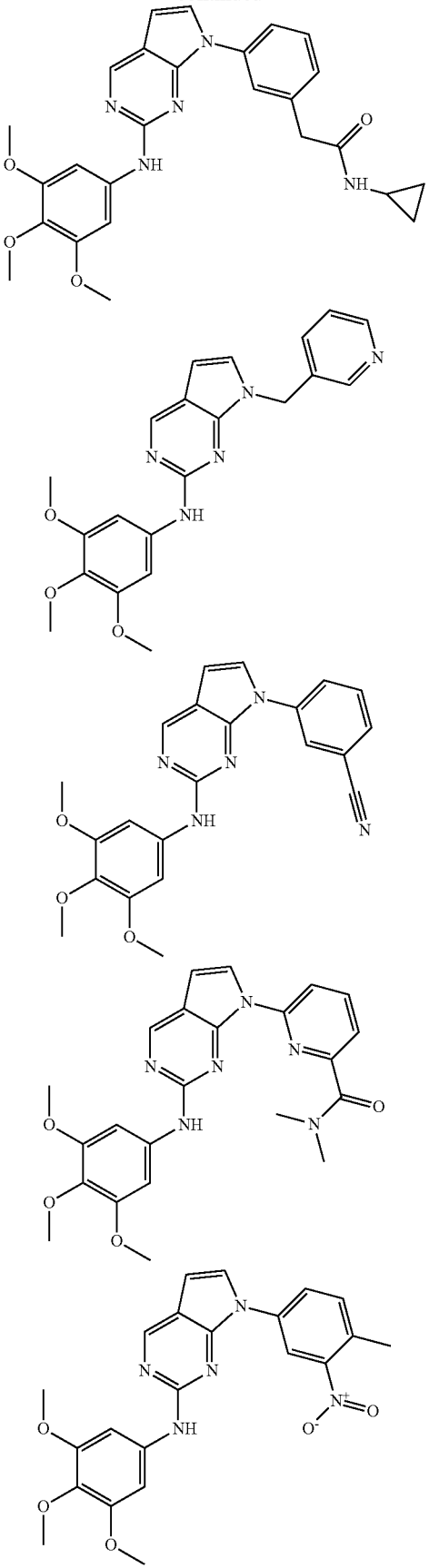

171
-continued
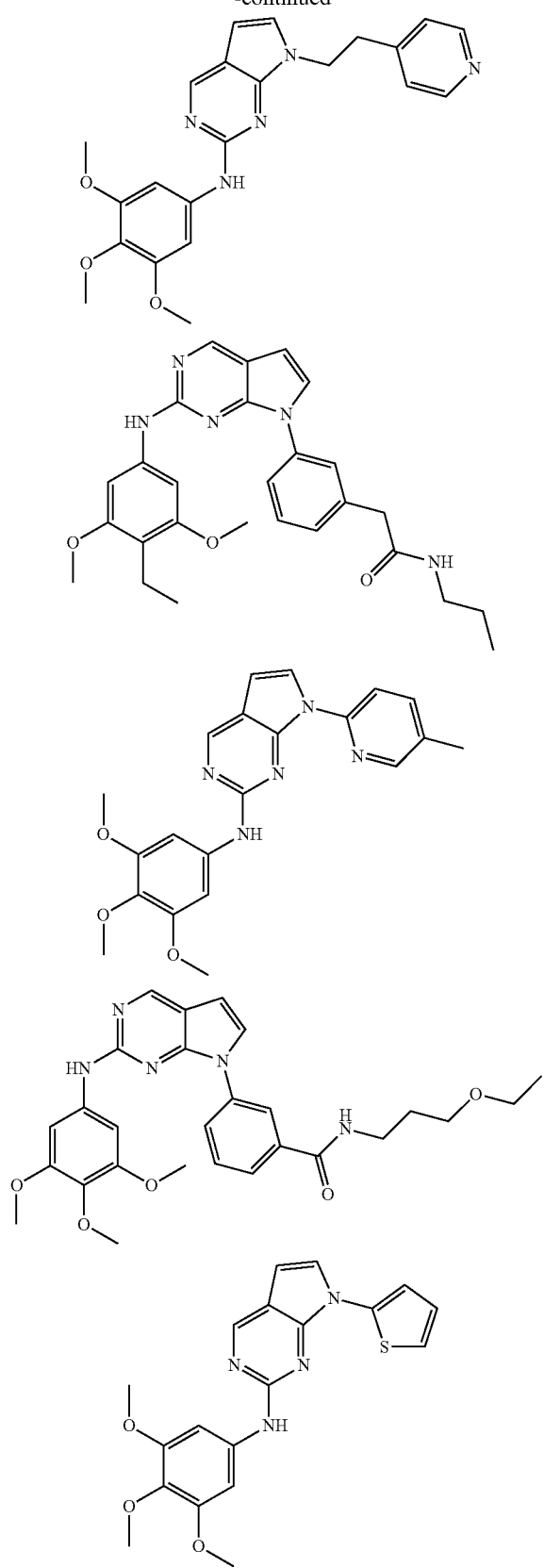
172
-continued
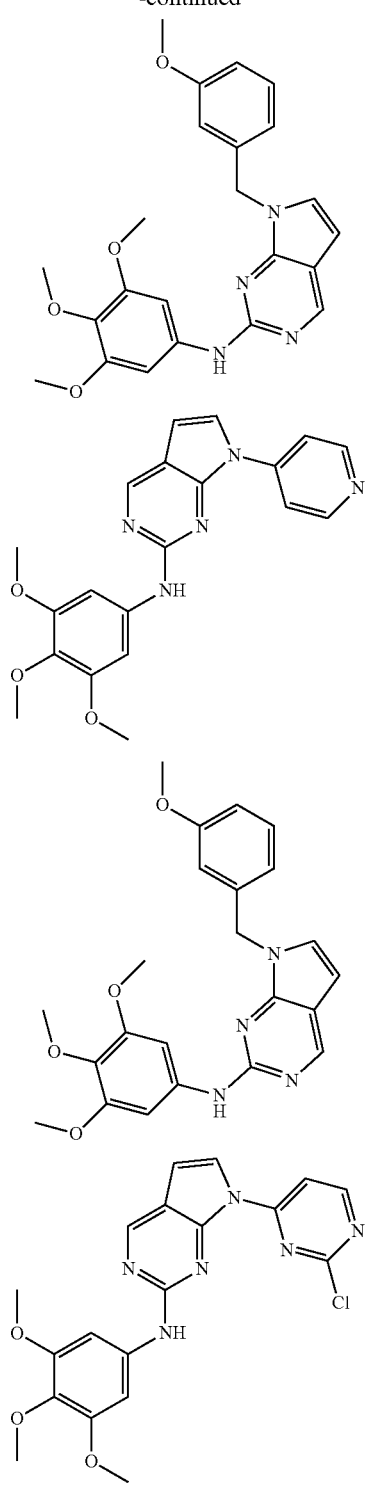

-continued
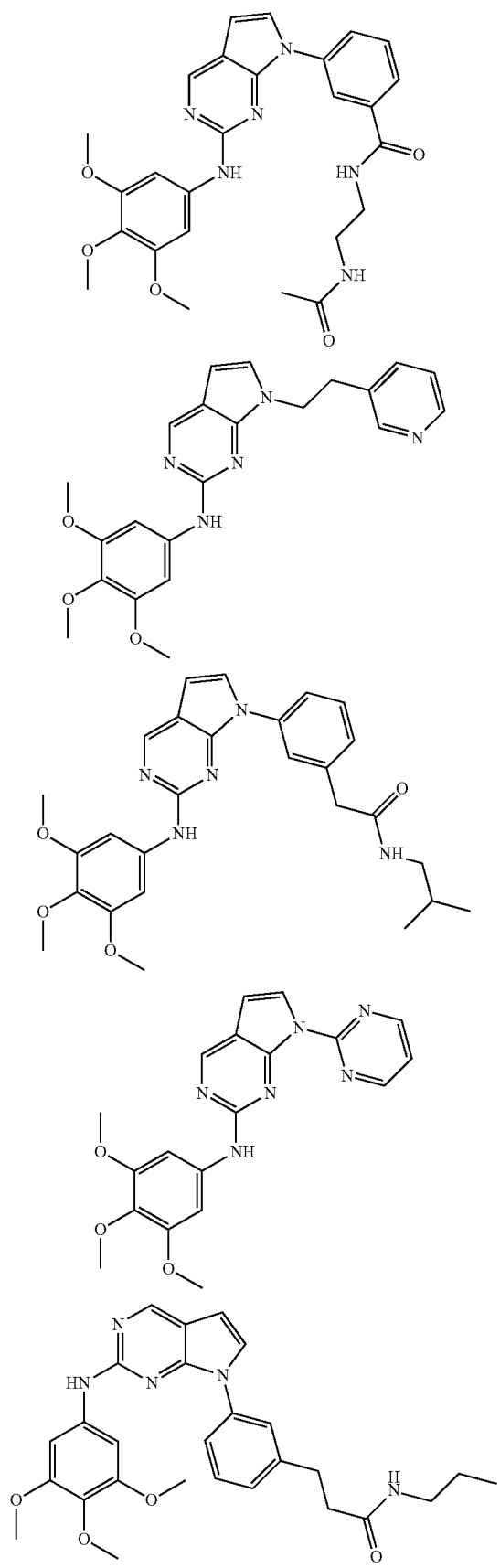
-continued
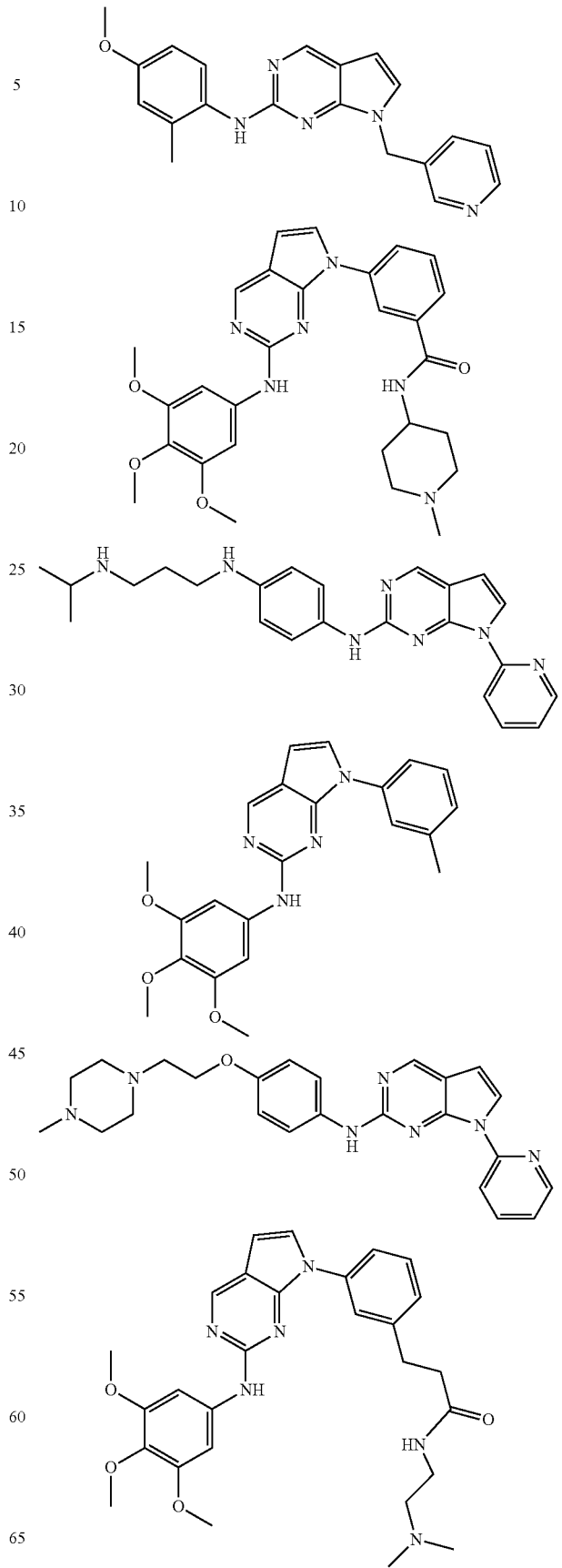

175
-continued
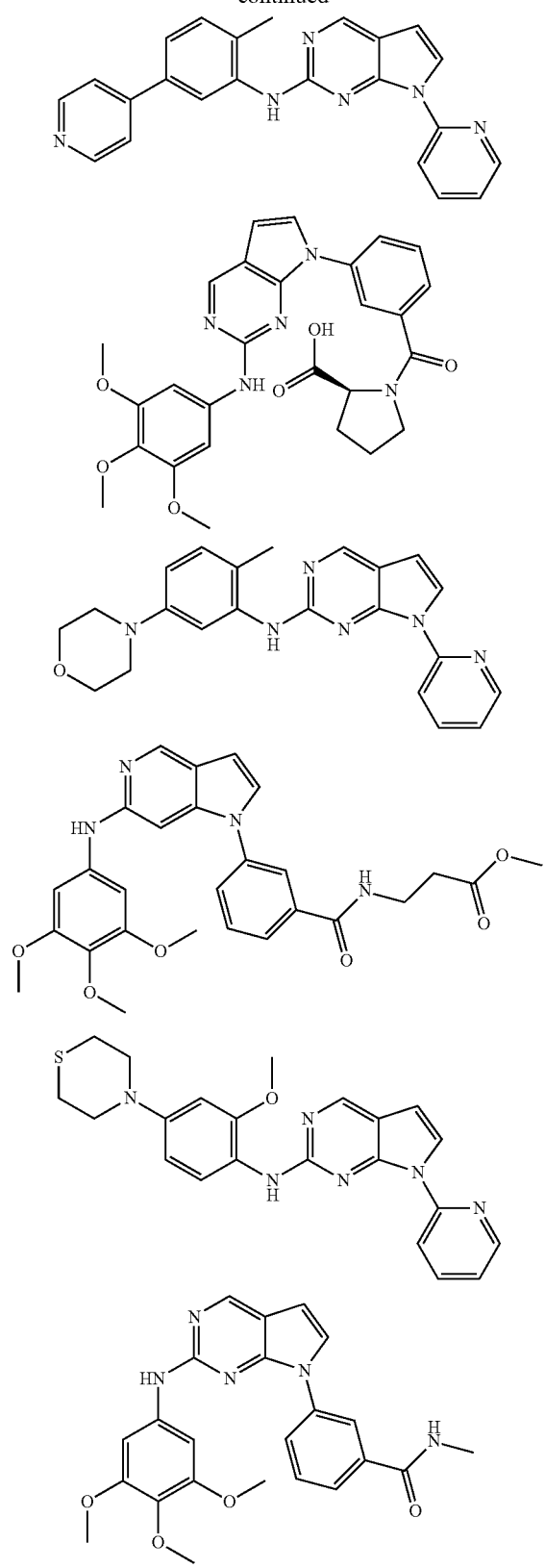
176
-continued
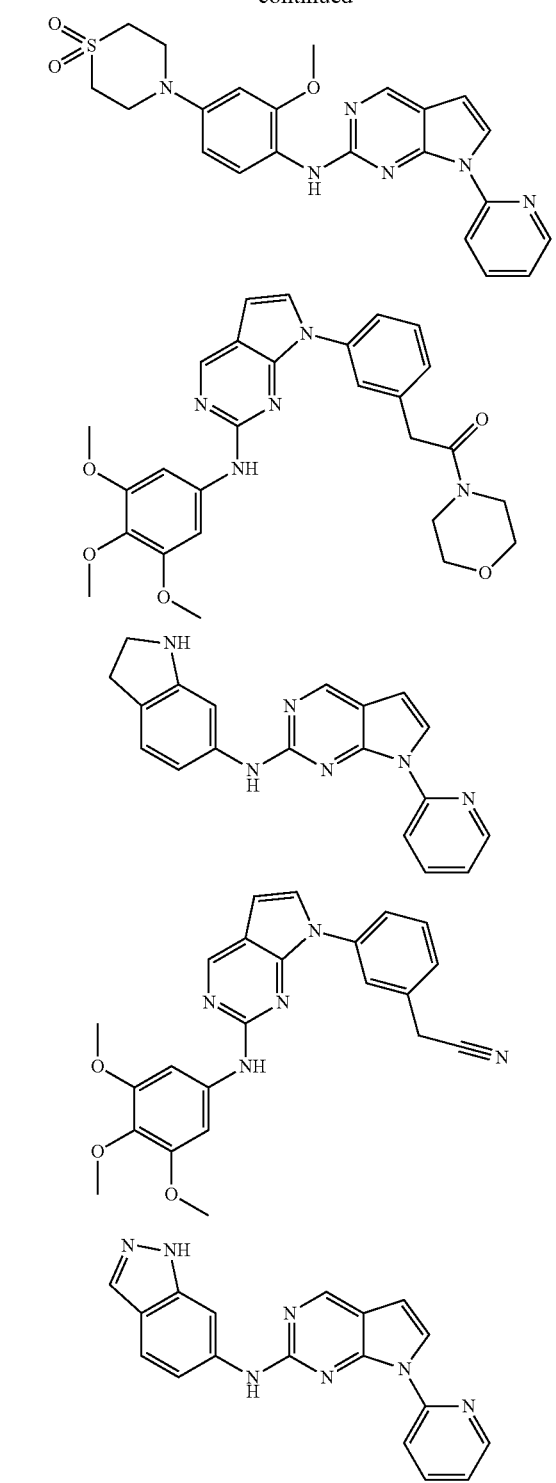

177
-continued
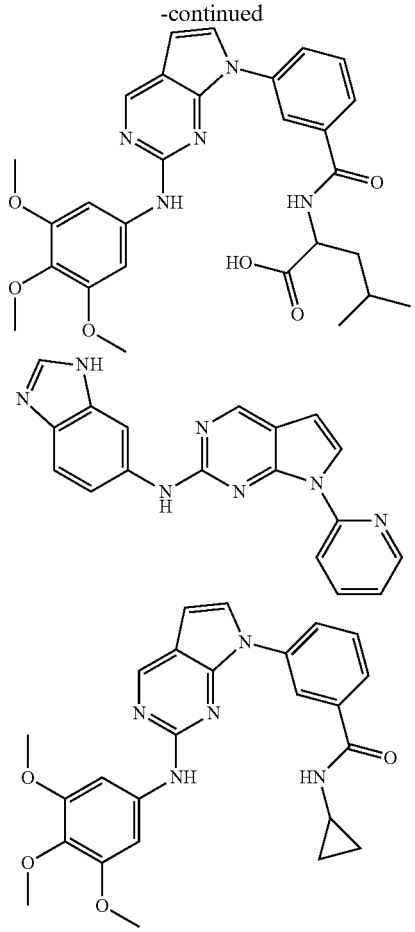
178
-continued
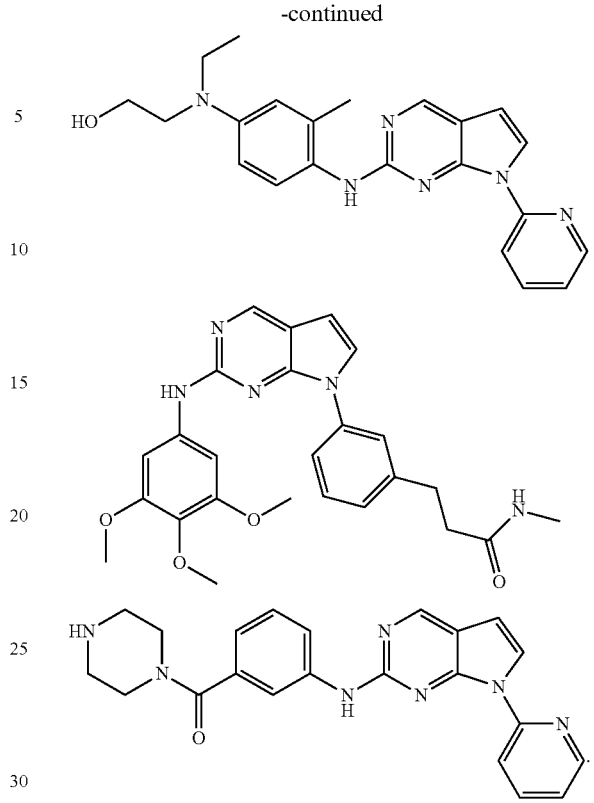
* * * * *